(12) United States Patent
Doshi

(10) Patent No.: US 12,060,432 B2
(45) Date of Patent: *Aug. 13, 2024

(54) COMBINATION THERAPIES WITH ANTI-CD38 ANTIBODIES

(71) Applicant: Janssen Biotech, Inc., Horsham, PA (US)

(72) Inventor: Parul Doshi, Chester Springs, PA (US)

(73) Assignee: JANSSEN BIOTECH, INC., Horsham, PA (US)

( * ) Notice: Subject to any disclaimer, the term of this patent is extended or adjusted under 35 U.S.C. 154(b) by 462 days.

This patent is subject to a terminal disclaimer.

(21) Appl. No.: 17/015,017

(22) Filed: Sep. 8, 2020

(65) Prior Publication Data

US 2021/0061920 A1 Mar. 4, 2021

Related U.S. Application Data

(63) Continuation of application No. 15/445,225, filed on Feb. 28, 2017, now Pat. No. 10,800,851, which is a continuation of application No. 14/629,941, filed on Feb. 24, 2015, now Pat. No. 9,603,927.

(60) Provisional application No. 62/006,386, filed on Jun. 2, 2014, provisional application No. 61/946,002, filed on Feb. 28, 2014.

(51) Int. Cl.
| | |
|---|---|
| A61K 39/00 | (2006.01) |
| A61K 31/00 | (2006.01) |
| A61K 31/4745 | (2006.01) |
| A61K 31/475 | (2006.01) |
| A61K 31/573 | (2006.01) |
| A61K 31/65 | (2006.01) |
| A61K 31/675 | (2006.01) |
| A61K 31/704 | (2006.01) |
| A61K 39/395 | (2006.01) |
| C07K 16/28 | (2006.01) |

(52) U.S. Cl.
CPC .......... *C07K 16/2896* (2013.01); *A61K 31/00* (2013.01); *A61K 31/4745* (2013.01); *A61K 31/475* (2013.01); *A61K 31/573* (2013.01); *A61K 31/65* (2013.01); *A61K 31/675* (2013.01); *A61K 31/704* (2013.01); *A61K 39/00* (2013.01); *A61K 39/39558* (2013.01); *C07K 16/2887* (2013.01); *A61K 39/001126* (2018.08); *A61K 2039/507* (2013.01); *C07K 2317/21* (2013.01); *C07K 2317/34* (2013.01); *C07K 2317/41* (2013.01); *C07K 2317/51* (2013.01); *C07K 2317/515* (2013.01); *C07K 2317/52* (2013.01); *C07K 2317/56* (2013.01); *C07K 2317/565* (2013.01); *C07K 2317/73* (2013.01); *C07K 2317/732* (2013.01); *C07K 2317/734* (2013.01)

(58) Field of Classification Search
CPC ...... A61K 39/39558; A61K 39/001126; C07K 2317/732; C07K 2317/734; A61P 35/00; A61P 35/02
See application file for complete search history.

(56) References Cited

U.S. PATENT DOCUMENTS

| | | |
|---|---|---|
| 6,737,056 B1 | 5/2004 | Presta |
| 7,183,387 B1 | 2/2007 | Presta |
| 7,223,397 B1 | 5/2007 | Rosenblum et al. |
| 7,829,673 B2 | 11/2010 | DeWeers |
| 7,829,693 B2 | 11/2010 | Kreutzer et al. |
| 8,008,449 B2 | 8/2011 | Korman et al. |
| 8,088,896 B2 | 1/2012 | Tesar et al. |
| 8,153,765 B2 | 4/2012 | Park et al. |
| 8,318,154 B2 | 11/2012 | Frost et al. |
| 8,354,509 B2 | 1/2013 | Carven et al. |
| 8,431,380 B2 | 4/2013 | Bookbinder et al. |
| 9,040,050 B2 | 5/2015 | Van De Winkel |
| 9,603,927 B2 | 3/2017 | Doshi |
| 9,732,154 B2 | 8/2017 | Doshi |
| 10,385,135 B2 | 8/2019 | Janssen et al. |
| 10,556,961 B2 | 2/2020 | Doshi |
| 10,604,580 B2 | 3/2020 | Lokhorst |
| 10,668,149 B2 | 6/2020 | Doshi et al. |
| 10,766,965 B2 | 9/2020 | Chaulagain |
| 10,781,261 B2 | 9/2020 | Janssen et al. |
| 10,793,630 B2 | 10/2020 | Doshi et al. |
| 10,800,851 B2 | 10/2020 | Doshi |
| 11,021,543 B2 | 6/2021 | Ahmadi et al. |
| 11,566,079 B2 | 1/2023 | Jansson et al. |
| 11,618,787 B2 | 4/2023 | Ahmadi et al. |
| 11,634,499 B2 | 4/2023 | Larmore |
| 11,708,419 B2 | 7/2023 | Jansson et al. |
| 11,708,420 B2 | 7/2023 | Jansson |
| 11,713,355 B2 | 8/2023 | Doshi et al. |
| 11,732,051 B2 | 8/2023 | Jansson et al. |
| 2004/0141982 A1 | 7/2004 | Lust et al. |
| 2004/0268425 A1 | 12/2004 | Bookbinder et al. |

(Continued)

FOREIGN PATENT DOCUMENTS

| | | |
|---|---|---|
| AU | 2013203186 A1 | 5/2013 |
| CL | 2013001944 A1 | 9/2014 |

(Continued)

OTHER PUBLICATIONS

Pui et al Nature Reviews vol. 6 p. 149 (2007), (Year: 2007).*

(Continued)

*Primary Examiner* — Sheela J. Huff
(74) *Attorney, Agent, or Firm* — HAMILTON, BROOK, SMITH & REYNOLDS, P.C.

(57) ABSTRACT

The present invention relates to combination therapies with anti-CD38 antibodies.

20 Claims, 6 Drawing Sheets

Specification includes a Sequence Listing.

(56) References Cited

U.S. PATENT DOCUMENTS

| | | |
|---|---|---|
| 2006/0257397 A1 | 11/2006 | Throsby |
| 2007/0148178 A1 | 6/2007 | Fyfe et al. |
| 2008/0063642 A1 | 3/2008 | Adelman et al. |
| 2008/0166344 A1 | 7/2008 | Nakahara et al. |
| 2009/0076249 A1 | 3/2009 | Deweers et al. |
| 2009/0148449 A1 | 6/2009 | DeWeers |
| 2009/0304687 A1 | 12/2009 | Drachman |
| 2009/0304710 A1 | 12/2009 | Park et al. |
| 2010/0068136 A1 | 3/2010 | Hansen |
| 2010/0074885 A1 | 3/2010 | Schiff et al. |
| 2010/0092489 A1 | 4/2010 | van de Winkel et al. |
| 2010/0285004 A1 | 11/2010 | Tesar et al. |
| 2011/0044997 A1 | 2/2011 | Adler et al. |
| 2011/0053247 A1 | 3/2011 | Baker |
| 2011/0066111 A1 | 3/2011 | Teschner et al. |
| 2011/0076273 A1 | 3/2011 | Adler et al. |
| 2011/0099647 A1 | 4/2011 | De Weers et al. |
| 2011/0293606 A1 | 12/2011 | Lejeune |
| 2011/0300157 A1 | 12/2011 | Devy et al. |
| 2012/0171153 A1 | 7/2012 | Frost et al. |
| 2012/0201827 A1 | 8/2012 | Elias |
| 2012/0219551 A1 | 8/2012 | Johnson et al. |
| 2012/0231008 A1 | 9/2012 | Guo et al. |
| 2012/0244110 A1 | 9/2012 | Chen et al. |
| 2012/0258081 A1 | 10/2012 | Corringham et al. |
| 2012/0259095 A1 | 10/2012 | Beliard et al. |
| 2012/0295864 A1 | 11/2012 | Taube et al. |
| 2013/0022588 A1 | 1/2013 | Yang et al. |
| 2013/0109593 A1 | 5/2013 | Hartmann et al. |
| 2013/0137134 A1 | 5/2013 | Mordechai et al. |
| 2013/0209355 A1 | 8/2013 | De Weers et al. |
| 2013/0302400 A1 | 11/2013 | Maneval et al. |
| 2013/0309250 A1 | 11/2013 | Cogswell et al. |
| 2013/0323247 A1 | 12/2013 | Zugmaier et al. |
| 2014/0051662 A1 | 2/2014 | Moussy et al. |
| 2014/0099254 A1 | 4/2014 | Chang et al. |
| 2014/0155584 A1 | 6/2014 | Elias et al. |
| 2014/0248238 A1 | 9/2014 | Wilson et al. |
| 2014/0271644 A1 | 9/2014 | Elias et al. |
| 2014/0309183 A1 | 10/2014 | Kerr |
| 2014/0314800 A1 | 10/2014 | Mathieu et al. |
| 2014/0356318 A1 | 12/2014 | Barken |
| 2015/0118251 A1 | 4/2015 | Deslandes |
| 2015/0125447 A1 | 5/2015 | Heider |
| 2015/0231235 A1 | 8/2015 | Van De Winkel |
| 2015/0246123 A1 | 9/2015 | Doshi |
| 2015/0246975 A1 | 9/2015 | Doshi |
| 2015/0376276 A1 | 12/2015 | Lewis et al. |
| 2016/0009683 A1 | 1/2016 | Hansen et al. |
| 2016/0067205 A1 | 3/2016 | Lokhorst |
| 2016/0222106 A1 | 8/2016 | Doshi et al. |
| 2016/0367663 A1 | 12/2016 | Doshi et al. |
| 2016/0376373 A1 | 12/2016 | Ahmadi |
| 2017/0008966 A1 | 1/2017 | Chaulagain |
| 2017/0044265 A1 | 2/2017 | Ahmadi |
| 2017/0107295 A1 | 4/2017 | Lokhorst |
| 2017/0121414 A1 | 5/2017 | Jansson et al. |
| 2017/0121417 A1 | 5/2017 | Jansson et al. |
| 2017/0174780 A1 | 6/2017 | Doshi |
| 2017/0320961 A1 | 11/2017 | Doshi |
| 2018/0117150 A1 | 5/2018 | O'Dwyer |
| 2019/0127479 A1 | 5/2019 | Ahmadi et al. |
| 2019/0144557 A1 | 5/2019 | Ahmadi et al. |
| 2019/0233533 A1 | 8/2019 | Otten |
| 2019/0330363 A1 | 10/2019 | Janssen et al. |
| 2019/0352421 A1 | 11/2019 | Adams et al. |
| 2020/0002433 A1 | 1/2020 | Janssen et al. |
| 2020/0121588 A1 | 4/2020 | Campbell et al. |
| 2020/0148782 A1 | 5/2020 | Jansson et al. |
| 2020/0223936 A1 | 7/2020 | Doshi et al. |
| 2020/0231697 A1 | 7/2020 | Jansson et al. |
| 2020/0268847 A1 | 8/2020 | Qi |
| 2020/0308284 A1 | 10/2020 | Bandekar et al. |
| 2020/0308296 A1 | 10/2020 | Bandekar et al. |
| 2020/0316197 A1 | 10/2020 | Bandekar et al. |
| 2020/0330593 A1 | 10/2020 | Bandekar et al. |
| 2020/0339701 A1 | 10/2020 | Jansson et al. |
| 2020/0392242 A1 | 12/2020 | Liu |
| 2020/0397896 A1 | 12/2020 | Liu |
| 2020/0405854 A1 | 12/2020 | Liu |
| 2020/0407459 A1 | 12/2020 | Chaulagain et al. |
| 2021/0047401 A1 | 2/2021 | Doshi et al. |
| 2021/0095042 A1 | 4/2021 | Jansson |
| 2021/0107991 A1 | 4/2021 | Jansson et al. |
| 2021/0403592 A1 | 12/2021 | Ahmadi et al. |
| 2022/0041745 A1 | 2/2022 | Bandekar et al. |
| 2022/0062415 A1 | 3/2022 | Xie et al. |
| 2022/0204638 A1 | 6/2022 | Liu et al. |
| 2022/0275090 A1 | 9/2022 | Alvarez Arias |
| 2022/0275101 A1 | 9/2022 | Schecter |
| 2022/0401465 A1 | 12/2022 | Fan et al. |
| 2023/0340145 A1 | 10/2023 | Ahmadi et al. |
| 2023/0391884 A1 | 12/2023 | Otten |

FOREIGN PATENT DOCUMENTS

| | | |
|---|---|---|
| CL | 2016002158 A1 | 7/2017 |
| EA | 009383 B1 | 12/2007 |
| EA | 015584 B1 | 10/2011 |
| EA | 201390993 | 12/2013 |
| EP | 2561868 A1 | 2/2013 |
| EP | 2567976 A2 | 3/2013 |
| EP | 2 459 167 B1 | 5/2013 |
| EP | 2 477 603 B1 | 3/2016 |
| JP | 2008-533977 A | 8/2008 |
| JP | 2009-511033 A | 3/2009 |
| JP | 2010-504363 A | 2/2010 |
| JP | 2010-506582 A | 3/2010 |
| JP | 2014-509837 A | 4/2014 |
| NZ | 576122 | 9/2012 |
| WO | WO 89/08114 A1 | 9/1989 |
| WO | WO 92/01049 A2 | 1/1992 |
| WO | WO 94/17184 A1 | 8/1994 |
| WO | WO 96/16990 A1 | 6/1996 |
| WO | WO 98/16245 A1 | 4/1998 |
| WO | WO 98/16254 A1 | 4/1998 |
| WO | WO 98/50435 A1 | 11/1998 |
| WO | WO 99/62526 A2 | 12/1999 |
| WO | WO 00/06194 A2 | 2/2000 |
| WO | WO 00/40265 A1 | 7/2000 |
| WO | WO 2001/060803 A1 | 8/2001 |
| WO | WO 01/97844 A1 | 12/2001 |
| WO | WO 02/06347 A1 | 1/2002 |
| WO | WO 02/32288 A2 | 4/2002 |
| WO | 2002-534396 A | 10/2002 |
| WO | WO 2003/106498 A2 | 12/2003 |
| WO | WO 2004/058288 A1 | 7/2004 |
| WO | WO 2004/078140 A2 | 9/2004 |
| WO | WO 2004/092160 A1 | 10/2004 |
| WO | WO 2005/042019 A1 | 5/2005 |
| WO | WO 2005/044855 A2 | 5/2005 |
| WO | WO 2005/063819 A2 | 7/2005 |
| WO | WO 2005/103083 A2 | 11/2005 |
| WO | WO 2006/088951 A2 | 8/2006 |
| WO | WO 2006/099875 A1 | 9/2006 |
| WO | WO 2006/125640 A2 | 11/2006 |
| WO | WO 2007/042309 A2 | 4/2007 |
| WO | WO 2008/037257 A2 | 4/2008 |
| WO | WO 2008/047242 A2 | 4/2008 |
| WO | WO 2008/073160 A2 | 6/2008 |
| WO | WO 2008/116103 A2 | 9/2008 |
| WO | WO 2008/121615 A2 | 10/2008 |
| WO | WO 2008/150530 A2 | 12/2008 |
| WO | WO 2009/062054 A1 | 5/2009 |
| WO | WO 2009/118142 A1 | 10/2009 |
| WO | WO 2009/128917 | 10/2009 |
| WO | WO 2010/052014 | 5/2010 |
| WO | WO 2010/061357 A1 | 6/2010 |
| WO | WO 2010/061358 A1 | 6/2010 |
| WO | WO 2010/061359 A1 | 6/2010 |
| WO | WO 2010/061360 A1 | 6/2010 |
| WO | WO 2011/012637 A2 | 2/2011 |
| WO | WO 2011/029892 A2 | 3/2011 |
| WO | WO 2011/109365 A2 | 9/2011 |

(56) References Cited

FOREIGN PATENT DOCUMENTS

| | | |
|---|---|---|
| WO | WO 2011/154456 A1 | 12/2011 |
| WO | WO 2012/041800 A1 | 4/2012 |
| WO | WO 2012/076663 A1 | 6/2012 |
| WO | WO 2012/092612 A1 | 7/2012 |
| WO | WO 2012/092616 A1 | 7/2012 |
| WO | WO 2013/059885 A2 | 5/2013 |
| WO | WO 2013/102144 A2 | 7/2013 |
| WO | WO 2013/164837 A1 | 11/2013 |
| WO | WO 2014/048921 A1 | 4/2014 |
| WO | WO 2014/068114 A1 | 5/2014 |
| WO | WO 2014/089416 A1 | 6/2014 |
| WO | WO 2014/142220 A1 | 9/2014 |
| WO | WO 2014/178820 A1 | 11/2014 |
| WO | WO 2015/009726 A2 | 1/2015 |
| WO | WO 2015/006450 A1 | 7/2015 |
| WO | WO 2015/121454 A1 | 8/2015 |
| WO | WO 2015/130728 A1 | 9/2015 |
| WO | WO 2015/130732 A2 | 9/2015 |
| WO | WO 2015/195555 A1 | 12/2015 |
| WO | WO 2015/195556 A1 | 12/2015 |
| WO | WO 2016/040294 A2 | 3/2016 |
| WO | WO 2016/089960 A1 | 6/2016 |
| WO | WO 2016/133903 A2 | 8/2016 |
| WO | WO 2016/187546 A1 | 11/2016 |
| WO | WO 2016/209921 A1 | 12/2016 |
| WO | WO 2016/210223 A1 | 12/2016 |
| WO | WO 2017/004266 A1 | 1/2017 |
| WO | WO 2017/079150 A1 | 5/2017 |
| WO | WO 2018/002181 A1 | 1/2018 |
| WO | WO 2018/213732 A1 | 11/2018 |
| WO | WO 2019/089832 A1 | 5/2019 |
| WO | WO 2019/186273 A1 | 10/2019 |
| WO | WO 2020/243911 A1 | 12/2020 |

OTHER PUBLICATIONS

Thomas et al Cancer vol. 106 p. 1569 (2006) (Year: 2006).*
Laurini et al Blood, vol. 120 p. 4795 (2012) (Year: 2012).*
"A Prospective Phase II of Daratumumab in Previously Treated Systemic Light Chain (AL) Amyloidosis", published online at //cms.cws.net/content/beta.myelomasociety.org/files/2017ash/Roussel,%20Murielle-ASH2017.pdf (2017).
Aarhust, et al., "ADP-ribosyl Cyclase and CD38 Catalyze the Synthesis of a Calcium mobilizing Metabolite from NADP+," The Journal of Biological Chemistry, 270(51): 30327-30333 (1995).
Abdi, J. et al., "Drug resistance in multiple myeloma: latest findings and new concepts on molecular mechanisms," Oncotarget, vol. 4; No. 12; 2186-2207 (2013).
Adriouch et al., "Extracellular NAD+: a danger signal hindering regulatory T cells," Microbes and Infection, 14:1284-1292 (2012).
Agheli, A. et al., "A Rare Case of Primary Amyloidosis, Presenting with Severe Pulmonary Hypertension and Bilateral Pleural Effusion," Blood, vol. 106: p. 5100 (2005).
Almagro, J.C. and Fransson, J., "Humanization of antibodies," Frontiers in Bioscience, vol. 13; 1619-1633 (2008).
Arican, et al., "Philadelphia Chromosome (+) T-Cell Acute Lymphoblastic Leukemia After Renal Transplantation," Transplantation Proceedings, vol. 31; 3242-3243 (1999).
Armitage et al., "Long-Term Remission Durability and Functional Status of Patients Treated for Diffuse Histiocytic Lymphoma with the CHOP Regimen," J. Clin. Oncol. 2:898-902, (1984).
Arthur, "Innovations in subcutaneous infusions," J. Infus. Nurs. 38(3); 179-87; May/Jun. 2015.
Bachireddy, et al., "Haematologic Malignancies: at the Forefront of Immunotherapeutic Innovation," Nature Reviews Cancer, vol. 15, No. 4, pp. 201-215, Apr. 1, 2015 (Apr. 1, 2015).
Bahlis, N.J. et al., "Daratumumab, lenalidomide, and dexamethasone (DRd) vs lenalidomide and dexamethasone (Rd) in relapsed or refractory multiple myeloma (RRMM): Efficacy and safety updated (POLLUX)," Journal of Clinical Oncology, vol. 35; No. 15; 8025; Abstract (2017).

Berglund, L. et al., "The epitope space of the human proteome," Protein Science, vol. 17; 606-613 (2008).
Blankestijn, et al., "Could daratumumab be used to treat severe allergy?," Journal of Allergy and Clinical Immunology, Elsevier, Amsterdam, NL, vol. 139, No. 5, p. 1677-1678, Jan. 19, 2017.
Bose, P. et al., "Treatment of Relapsed/Refractory Acute Myeloid Leukemia," Curr. Treat. Options in Oncol., vol. 18; No. 17; 30 pages (2017).
Brand, F-X. et al., "Prospect for Anti-HER2 Receptor Therapy in Breast Cancer," AntiCancer Research, vol. 26; 463-470 (2006).
Brown, et al., "Tolerance of single, but not multiple, amino acid replacements in antibody VH CDR 2: a means of minimizing B cell wastage from somatic hypermutation?" The Journal of Immunology, 156: 3285-3291 (1996).
Carter et al., "Identification and validation of cell surface antigens for antibody targeting in oncology," Endocrine-Related Cancer, vol. 11, pp. 659-687, (2004).
Chari et al., "Subcutaneous Delivery of Daratumumab in Patients with Relapsed or Refractory Multiple Myeloma (RRMM): PAVO, an Open-label, Multicenter, Dose Escalation Phase 1b Study," American Society of Hematology, Clinical Trials.gov Identifier NCT02519452, Dec. 2017.
Chari A. et al., "Subcutaneous delivery of daratumumab in patients (pts) with relapsed or refractory multiple myeloma (RRMM): PAVO, an openlabel, multicenter, dose escalation phase 1b study," 2017 ASH Annual Meeting *ANZMAP Multiple Myeloma Highlights*, 2017.
Chaulagain, C.P., et al., "How we Treat Systemic Light-Chain Amyloidosis," Clinical Advances in Hematology & Oncology, vol. 13; No. 5; 315-324 (2015).
Chaulagain, C.P. and Comenzo, R.L., "New Insights and Modern Treatment of AL Amyloidosis," Curr Hematol Malig Rep, vol. 8; 291-298 (2013).
Chen, et al., "Selection and Analysis of an Optimized Anti-VEGF Antibody: Crystal Structure of an Affinity-matured Fab in Complex with Antigen," Journal of Molecular Biology, 293: 865-881 (1999).
Cheson et al., "Revised Response Criteria for Malignant Lymphoma," Journal of Clinical Oncology, vol. 25, No. 5, 579-586 (Feb. 10, 2007).
Chiarugi, A. et al., "The NAD metabolome—a key determinant of cancel cell biology," Nature Reviews, vol. 12; 741-752 (2012).
Chillemi, A. et al., "Anti-CD38 Antibody Therapy: Windows of Opportunity Yielded by the Functional Characteristics of the Target Molecule," Molecular Medicine, vol. 19; 99-108 (2013).
Chou, et al., "Drug Combination Studies and their Synergy Quantification Using the Chou-Talalay Method," Cancer Research, 70(2): 440-446 (2010).
Clinicaltrials.gov, "Daratumumab in Combination with ATRA (DARA/ATRA)," Identifier: NCT02751255; First posted: Apr. 26, 2016 (11 pages).
ClinicalTrials.gov "Study of YM155 in Refractory Diffuse Large B-cell Lymphoma (DLBCL) Subjects," Interventional Studies, U.S. National Library of Medicine, //clinicaltrials.gov/ct2/show/record/NCT00498914, First posted Jul. 11, 2007 [retrieved on Sep. 10, 2018] (14 pages).
Clinicaltrials.gov, "A Study of Daratumumab with the Addition of Recombinant Human Hyaluronidase (rHuPH20) for the Treatment of Participants with Relapsed or Refractory Multiple Myeloma," Identifier: NCT02519452; First Posted: Aug. 11, 2015 (13 pages).
Clinicaltrials.gov, "A Study to Evaluate Subcutaneous Daratumumab in Combination with Standard Multiple Myeloma Treatment Regimens," Identifier: NCT03412565, First Posted: Jan. 26, 2018 (16 pages).
Clinicaltrials.gov, "A Phase 1 Study to Assess the Safety, Tolerability, and Pharmacokinetics of TAK-079 in Healthy Participants," Identifier: NCT02219256, 13 pages; Latest version posted: Mar. 22, 2017. (13 pages).
Colman, "Effects of amino acid sequence changes on antibody-antigen interactions," A Structural View of Immune Recognition by Antibodies, Biomolecular Research Institute, 33-36, (1994).
Comenzo, R.L. et al., "Consensus guidelines for the conduct and reporting of clinical trials in systemic light-chain amyloidosis," Leukemia, vol. 26; 2317-2325 (2012).

(56) References Cited

OTHER PUBLICATIONS

Cotner, et al., "Human T Cell Proteins Recognized by Rabbit Heteroantisera and Monoclonal Antibodies," International Journal of Immunopharmaceuticals, 3(3): 255-268 (1981).
Data show daratumumab achieved a pronounced overall response rate as a single-agent with tolerable safety profile in heavily pre-treated multiple myeloma patients, Johnson & Johnson Press release[online](retrived on Jul. 27, 2020), May 30, 2015, retrieved from the Internet<URL:https://www.jnj.com/media-center/press-releases/Data-show-daratumumab-achieved-a-pronounced-overall-response-rate-as-a-single-agent-with-tolerable-safety-profile-in-heavily-pre-treated-multiple-myeloma-patients>; 4 pages.
Davies, et al., "Affinity improvement of single antibody VH domains: residues in all three hypervariable regions affect antigen binding," Immunotechnology, 2: 169-179 (1996).
Davis, et al., "Transgenic mice as a source of fully human antibodies for the treatment of cancer," Cancer and Metastasis Reviews, 18: 421-425 (1999).
Deckert, et al., "SAR650984, A Novel Humanized CD38-Targeting Antibody, Demonstrates Potent Antitumor Activity in Models of Multiple Myeloma and Other CD38β Hematologic Malignancies," Clinical Cancer Research. vol. 20, No. 17, pp. 4574-4583 (2014).
Dennis, "Off by a Whisker," Nature, 442 (17): 749-741 (2006).
DePascalis, et al., "Grafting of 'Abbreviated' Complementarity-Determining Regions Containing Specificity-Determining Residues Essential for Ligand Contact to Engineer a Less Immunogenic Humanized Monoclonal Antibody," The Journal of Immunology, 169: 3076-3084 (2002).
Dewolf, S. and Tallman, M., "How I Treat Relapsed or Refractory AML," Blood, downloaded from: https://ashpublications.org/blood/article-abstract/doi/10.1182/blood.2019001982/460740/How-I-Treat-Relapsed-or-Refractory-AML?redirectedFrom=PDF; 32 pages (2020).
De Haart, S.J. et al., "Accessory Cells of the Microenvironment Protect Multiple Myeloma from T-Cell Cytotoxicity through Cell Adhesion-Mediated Immune Resistance," Clinical Cancer Research, vol. 19; No. 20; 5591-5601 (2013).
De Weers, et al., "Daratumumab, a Novel Therapeutic Human CD38 Monoclonal Antibody, Induces Killing of Multiple Myeloma and Other Hematological Tumors," The Journal of Immunology, 186: 1840-1848 (Pre-published online Dec. 27, 2010).
De Weers, M. et al., "Humax-CD38, a New Human CD38 Monoclonal Antibody, Effectively Mediates Killing of Multiple Myeloma and Plasma Cell Leukemia Cells," abstract, Submitted for the 16$^{th}$ European Congress of Immunology—ECI2006, Paris, France, [Sep. 6-9, 2006].
De Weers et al., "HuMax-CD38, a new human CD38 monoclonal antibody, effectively mediates killing of multiple myeloma and plasma cell leukemia cells," The 23$^{rd}$ International Conference on 'Advances in the Application of Monoclonal Antibodies in Clinical Oncology, (Jun. 26-28, 2006), Royal Myconian Resort & Thalasso Spa Center, Mykonos, Greece (Abstract).
Dimopoulos, M.A. et al., "Daratumumab, Lenalidomide, and Dexamethasone for Multiple Myeloma," The New England Journal of Medicine, vol. 375; No. 14; 1319-1331 (2016).
Dimopoulos, M.A. et al., "Daratumumab plus lenalidomide and dexamethasone versus lenalidomide and dexamethasone in relapsed or refractory multiple myeloma: updated analysis of POLLUX," Haematologica, vol. 103; No. 12; 2088-2096 (2018).
Dispenzieri, A. et al., "Treatment of Immunoglobulin Light Chain Amyloidosis: Mayo Stratification of Myeloma and Risk-Adapted Therapy (mSMART) Consensus Statement," Mayo Clin Proc., vol. 90; No. 8; 1054-1081 (2015).
DMC recommends termination of study into daratumumab with atezolizumab to treat NSCLC, European Pharmaceutic Manufacturer[online](retrieved on Jul. 26, 2020), May 30, 2018, retrieved from the Internet<URL:https://www.epmmagazine.com/news/dmc-recommends-termination-of-study-into-daratumumab/>; 3 pages.

Dos Santos, et al., Anti-Leukemic Activity of Daratumumab in Acute Myeloid Leukemia Cells and Patient-Derived Xenografts, Blood, vol. 124, Abstract 2312, (2014).
Doshi, et al., "Daratumumab Treatment in Combination with Chop or R-Chop Results in the Inhibition or Regression of Tumors in Preclinical Models of Non-Hodgkins Lymphoma," Haematologica, The Hematology Journal, 99(1): 138 (2014).
Eldfors, et al., "Landscape of Mutations in Relapsed Acute Myeloid Leukemia," vol. 124: No. 21, p. 2367; (2014).
Ellis, et al., "Engineered Anti-CD38 Monoclonal Antibodies for Immunotherapy of Multiple Myeloma," The Journal of Immunology, 155: 925-937 (1995).
Engert, et al., "A Phase-I Study of an Anti-CD25 Ricin A-Chain Immunotoxin (RFT5-SMPT-dgA) in Patients with Refractory Hodgkin's Lymphoma," Blood, 89(2): 403-410 (1997).
Ettinger, R. et al., "Pathogenic mechanisms of IgE-mediated inflammation in self-destructive autoimmune responses," Autoimmunity, vol. 50; No. 1; 25-36 (2017).
Ferrero, et al., Characterization and phylogenetic epitope mapping of CD38 ADPR cyclase in the cynomolgus macaque, BMC Immunology, 5(21): 1-13 (2004).
Field-Smith, "Bortezomid (Velcade™) in the treatment of multiple myeloma," Therapeutic and Clinical Risk Management, 2(3): 271-279 (2006).
Flavell, et al., "Therapy of human T-cell acute lymphoblastic leukaemia with a combination of anti-CD7 and anti-CD38-SAPORIN immunotoxins is significantly better than therapy with each individual immunotoxin," Br. J. Cancer, vol. 84, No. 4, pp. 571-578, (2001).
Franco, et al., "The transmembrane glycoprotein CD38 is a catalytically active transporter responsible for generation and influx of the second messenger cyclic ADP-ribose across membranes," FASEB Journal, 12: 1507-1520 (1998).
Fujimori, et al., "A Modeling Analysis of Monoclonal Antibody Percolation Though Tumors: A Binding-Site Barrier," Journal of Nucleic Medicine, 31: 1191-1198 (1990).
Fujioka, Y. and Kurokawa, M., "Follicular lymphoma presenting with massive splenomegaly," International J Hematol, vol. 95; 3-4 (2012).
Funaro et al., "CD38 Functions Are Regulated Through an Internalization Step," Journal of Immunology, 160: 2238-2247 (1998).
Funaro, et al., "Human CD38: a versatile leukocyte molecule with emerging clinical prospectives," Fundamental and Clinical Immunology, 3(3): 101-113 (1995).
Funaro, et al., "Identification and characterization of an active soluble form of human CD38 in normal and pathological fluids," International Immunology, 8(11): 1643-1650 (1996).
Funaro, et al., "Involvement of the Multilineage CD38 Molecule in a Unique Pathway of Cell Activation and Proliferation," The Journal of Immunology, 145: 2390-2396 (1990).
Gallo, et al., "The human immunoglobulin loci introduced into mice: V(D) and J gene segment usage similar to that of adult humans," European Journal of Immunology, 30: 534-540 (2000).
Genmab "Humanx-CD38 Effective in Preclinical Studies," Genmab A/S, Stock Exchange Release 57/2005.
Genmab "Daratumumab Receives Breakthrough Therapy Designation from US Food and Drug Administration", Copenhagen, Denmark; May 1, 2013—Genmab A/S (OMX: GEN) disponible en: http://files.shareholder.com/downloads/AMDA-KPIBN/0x0x659093/64b187b8-830c-4252-acd6-8019b4199069/18%20Daratumumab%20breakthrough%20status_010513_uk.pdf, (May 1, 2013).
Genmab Announces Daratumumab and Ofatumumab Data to Be Presented at American Society of Hematology Annual Meeting (ASH), American Society of Hematology Annual Meeting and Exposition, San Francisco, California, Media Release 06; pp. 1-3 (Nov. 2014).
George, et al., "Differential Effects of Anti-β2-Glycoprotein I Antibodies on Endothelial Cells and on the Manifestations of Experimental Antiphospholipid Syndrome," Circulation, 97: 900-906 (1998).
Goldmacher, et al., "Anti-CD38-Blocked Ricin: An immunotoxin for the Treatment of Multiple Myeloma," The American Society of Hematology, 84(9): 3017-3025 (1994).

(56) References Cited

OTHER PUBLICATIONS

Goodwin, "Subcutaneous Daratumumab Potential Game Changer for Multiple Myeloma," Oncology Times, 2017 American Society of Hematology Annual Meeting, p. 49, (2017).
Gopalakrishnan, et al. "Daratumumab improves the anti-myeloma effect of newly emerging multidrug therapies," Blood and Lymphatic Cancer: Targets and Therapy, 3: 19-24 (2013).
Graeff, et al., "Enzymatic Synthesis and Characterizations of Cyclic GDp-ribose," The Journal of Biological Chemistry, 269(48): 30260-30267 (1994).
Green, "Antibody engineering via genetic engineering of the mouse: XenoMouse strains are a vehicle for the facile generation of therapeutic human monoclonal antibodies," Journal of Immunological Methods, 231: 11-23 (1999).
Green, et al., "Antigen-specific human monoclonal antibodies from mice engineered with hyman Ig heavy and light chain YACs," Nature Genetics, 7: 13-21 (1994).
Gupta, R. et al., "The Economic Impact of Childhood Food Allergy in the United States," JAMA Pediatrics, vol. 167; No. 11; 1026-1031 (2013).
Guse et al., "Regulation of calcium signaling in T lymphocytes by the second messenger cyclic ADP-ribose," Nature 398:70-73, (1999).
Haart, et al., "Sepantronium bromide (YM155) improves daratumumab-mediated cellular lysis of multiple myeloma cells by abrogation of bone marrow stromal cell-induced resistance," Haematologica, Letters to the Editor, vol. 101, No. 8, pp. e339-e343, (2016).
Hara-Yokoyama, "Alteration of enzymatic properties of cell-surface antigen CD38 by agonistic anti-CD38 antibodies that prolong B cell survival and induce activation," International Immunopharmacology, 8: 59-70 (2008).
Hartmann, Radioimmunotherapy of Nude Mice Bearing a Human Interleukin 2 Receptor α-expressing Lymphoma Utilizing the α-emitting Radionuclide-conjugated Monoclonal Antibody 212Bi-anti-Tac, Cancer Research, 54: 4362-4370 (1994).
Henry, et al., "the use of basiliximab in solid organ transplantation," Expert Opinion Pharmacotherapy, 3(10): 1657-1663 (2002).
Holgate, S.T., "New strategies with anti-IgE in allergic diseases," World Allergy Organization Journal, vol. 7; No. 17; 6 pages (2014).
Holm, et al., "Functional mapping and single chain construction of the anti-cytokeratin 8 monoclonal antibody TS1," Molecular Immunology, 44: 1075-1084 (2017).
Hoshino, et al., "Mapping of the Catalylic and Epitopic Sites of Human CD38/NAD+ Glycohydrolase to a Functional Domain in the Carboxyl Terminus1," The Journal of Immunology, 158: 741-747 (1997).
Howard, et al., "Formation and Hydrolysis of Cyclic ADP-Ribose Catalyzed by lymphocyte Antigen CD38," Science, 262(5136): 1056-1059 (1993).
Hu, Y., et al., "Immunophenotypic analysis of abnormal plasma cell clones in bone marrow of primary systemic light chain amyloidosis patients," Chin Med J., vol. 127; No. 15; 2765-2770; Abstract only (2014).
Hu, Y. et al., "The Significance of Abnormal Plasma Cell Clone in Bone Marrow of Primary Systemic Light Chain Amyloidosis Patients," Blood, vol. 122; p. 5342 (2013).
Ikehata, et al., "Autoantibodies against CD38 (ADP-ribosyl Cyclase/Cyclic ADP-ribose Hydrolase) that Impair Glucose-induced Insulin Secretion in Noninsulin-dependent Diabetes Patients," Journal of Clinical Investigations, 102(2): 395-401 (1998).
Inaba, H. et al., "Acute lymphoblastic leukaemia," Lancet, vol. 381; 27 pages (2013).
Jackisch, et al., "Subcutaneous versus intravenous formulation of trastuzumab for HER2-positive early breast cancer: updated results from the phase III HannaH study," Annals of Oncology, vol. 26, pp. 320-325, (2015).
Jackson, et al., "Isolation of a cDNA Encoding The Human CD38 (T10) molecule, A Cell Surface Glycoprotein With An Unusual Discontinuous Pattern of Expression During Lymphocyte Differentiation," The Journal of Immunology, 144(7): 2811-2815 (1990).

Jagannath, et al. Treatment (tx) journeys in newly diagnosed multiple myeloma (NDMM) patients (pts): Results from the Connect MM Registry. Multiple Myeloma Update from the American Society of Clinical Oncology. (ASCO) $41^{st}$ Annual meeting, (Jun. 4, 2018).
Jakob, et al., "Stage-dependent Expression of CD7, CD45RO, CD45RA and CD25 on CD4-positive Peripheral Blood T-lymphocytes in Cutaneous T-cell Lymphoma," Acta Derm Venerology, 76: 34-36 (1996).
Jakobovits, "the long-awaited magic bullets: therapeutic human monoclonal antibodies from transgenic mice", Expert Opinion on Investigational Drugs, 7(4): 607-614 (1998).
Jang, et al., "The structural basis for DNA binding by an anti-DNA autoantibody," Molecular Immunology, 35: 1207-1217 (1998).
Johnson, et al., "Primary plasma cell leukemia: morphologic, immunophenotypic, and cytogenetic features of 4 cases treated with chemotherapy and stem cell transplantation," Annals of Diagnostic Pathology, 10: 263-268 (2006).
Johnson & Johnson, Janssen to Demonstrate Breadth of Oncology Portfolio with 42 Clinical Data Presentation at the 2014 American Society of Hematology (ASH) Annual Meeting, San Francisco, California (Nov. 2014).
Jones, et al., "Depletion of CD25+ regulatory calls results in suppression of melanoma growth and induction of autoreactivity in mice," Cancer Immunity, 2: 1 (2002). Abstract.
Jones, et al., "Replacing the complementarity-determining regions in a human antibody with those from a mouse," Nature, 321: 522-525 (1986).
Kaufman, G.P. et al., "Daratumumab yields rapid and deep hematologic responses in patients with heavily pretreated AL amyloidosis," Blood, vol. 130; No. 7; 900-902 (2017).
Kita et al., "Antitumor effects of YM155, a novel suppressant, against human aggressive non-Hodgkin Lymphoma," Leukemia Research, vol. 35, pp. 787-792, (2011).
Kita, A., et al., "Sepantronium Bromide (YM155) Enhances Response of Human B-Cell Non-Hodgkin Lymphoma to Rituximab," The Journal of Pharmacology and Experimental Therapeutics, vol. 343; No. 1; 178-183 (2012).
Konapleva, et al., "Ligation of Cell Surface CD38 Protein with Agonistic Monoclonal Antibody Induced a Cell Growth Signal in Myeloid Leukemia Cells," The Journal of Immunology, 161: 4702-4708 (1998).
Kong, S.Y., et al., "Daratumumab Directly Induces Human Multiple Myeloma Cell Death and Acts Synergistically with Conventional and Novel Anti-Myeloma Drugs," Blood, vol. 116; Abstract 3013 (2010).
Konopleva, et al., "CD38 in Hematopoietic Malignancies," Chemical Immunol. Basel Karger, 75: 189-206 (2000).
Kreitman, et al., Phase I Trial of Recombinant Immunotoxin Anti-Tac (Fv)-PE38 (LMB-2) in Patients with Hematologic Malignancies, Journal of Clinical Oncology, 18: 1622-1636 (2000).
Krejcik, J. et al., "Daratumumab depletes CD38+ immune regulatory cells, promotes T-cell expansion, and skews T-cell repertoire in multiple myeloma," Blood, vol. 128; No. 3; 384-394 (2016).
Krejcik, J. et al., Immunomodulatory Effects and Adaptive Immune Response to Daratumumab in Multiple Myeloma,: Blood, vol. 126; 3037; 7 pages (2015).
Kreuger, et al., "Successful in vivo blockade of CD25 (high-affinity interleukin 2 receptor) on T cells by administration of humanized anti-Tac antibody to patients with psoriasis," Journal of American Academy of Dermatology, 41(3): 448-458 (2000).
Kropff, et al., "Bortezomib in combination with dexamethoasone for relapsed multiple myeloma," Leukemia Research, 29: 587-590 (2005).
Kumar, S. et al., "Expression of CD52 on plasma cells in plasma cell proliferative disorders," Blood, vol. 102; No. 3; 1075-1077 (2003).
Kupiec-Weglinski, "CD25-Targeted Therapy Revisited," Transplantation, 69(3): 328-330 (2000).
Lakshman, A. et al., "Efficacy of daratumumab-based therapies in patients with relapsed, refractory multiple myeloma treated outside of clinical trials," Am J. Hematol., vol. 92; 1146-1155 (2017).

(56) References Cited

OTHER PUBLICATIONS

Lande, et al., "CD38 ligation plays a direct role in the induction of IL-1β, I-6, and IL-10 secretion in resting human monocytes," Cellular Immunology, 220: 30-38 (2002).
Laubach, J.P., "Daratumumab granted breakthrough drug status," Expert Opinion Investig. Drugs, vol. 23; No. 4; 445-452 (2014).
Laurie, et al., "The role of CD4+CD25+ immunoregulatory T cells in the induction of autoimmune gastritis," Immunology and Cell Biology, 80: 567-573 (2002).
Lazar, et al., "Transforming Growth Factor α: Mutation of Aspartic Acid 47 and Leucine 48 Results in Different Biological Activities," Molecular and Cellular Biology, 8(3): 1247-1252 (1988).
Leonard, et al., "Molecular cloning and expression of cDNAs for the human interleukin-2 receptor," Nature 311(18): 626-631 (1984).
Lepenies, B. and Jacobs, T., "The Role of Negative Costimulators During Parasitic Infections," Endocrine, Metabolic & Immune Disorders—Drug Targets, vol. 8; 279-288 (2008).
Leveque "Subcutaneous Administration of Anticancer Agents" Anticancer Research, Departments of Pharmacy, University Hospital, Strasbourg, France, vol. 34, pp. 1579-1586 (2014).
Li, et al., "Creation of Patient Derived AML Xenografts Displaying Distinct Phenotypes and Geneotypes," Blood, vol. 122: No. 21, p. 5018 (2013).
Lin, et al., "Structure-Function Relationships in Glucagon: Properties of Highly Purified Des-His1-, Monoiodi-, and [Des-Asn28, Thr29](homoserine lactone27)-glucagon," Biochemistry, 14(9): 1559-1563 (1975).
Lippincott-Schwartz, "Antibodies as cell Biological Tools," Current Protocols in Cell Biology, 16.0.1-16.0.2, (2002).
Liu et al., "Induction of Chemoresistance by All-Trans Retinoic Acid via a Noncanonical Signaling in Multiple Myeloma Cells," PLOS One, vol. 9, No. 1, page Article No. e85571, Jan. 2014.
Lonberg, et al., "Antigen-specific human antibodies from mice comprising four distinct genetic modifications," Nature: 308: 856-859 (1994).
Lu et al., "Issues Related to Targeted Delivery of Proteins & Peptides," The AAPS Journal, vol. 8, No. 3, Article 55, pp. E466-E478, Jul. 21, 2006.
MacCallum, et al., "Antibody-antigen Interactions: Contact Analysis and Binding Site Topography," Journal of Molecular Biology, 262, 732-745 (1998).
Machida, H. et al., "Aggressive plasma cell leukemia with cleaved, multilobated and monocytoid nuclei," International Journal of Hematol., vol. 73; Suppl 1; 158; Abstract No. 411 (2001).
Mai, E. et al., "Phase III trial of bortezomib, cyclophosphamide and dexamethasone (VCD) versus bortezomib, doxorubicin and dexamethasone (Pad) in newly diagnosed myeloma," Leukemia, vol. 29; 1721-1729 (2015).
Malavasi, et al., "Human CD38: a glycoprotein in search of a function," Immunology Today, 15(3): 95-97 (1994).
Maloney, et al., "Antibody Therapy for Treatment of Multiple Myeloma," Semin Hematol. 36 (Suppl. 3): 30-33 (1999).
Manier, S. et al., "Bone Marrow Microenvironment in Multiple Myeloma Progession," Journal of Biomedicine and Biotechnology, vol. 2012; 5 pages (2012).
Matas-Cespedes, A. et al., "The human CD38 monoclonal antibody daratumumab shows anti-tumor activity and hampers leukemia-microenvironment interactions in chronic lympocytic leukemia," Clinical Cancer Research, vol. 23; No. 6; 1493-1505 (2017).
Mauri, C. and Menon, M., "The expanding family of regulatory B cells," International Immunology, vol. 27; No. 10; 479-486 (2015).
McCarthy, P.L., "Strategies for induction, autologous hematopoietic stem cell transplantation, consolidation, and maintenance for transplantation-eligible multiple myeloma patients", Hematology, vol. 2013, NI. 1, pp. 496-503 (Dec. 2013).
McKelvey, et al., "Hydroxyldaunomycian (Adriamycin) Combination Chemotherapy in Malignant Lymphoma," Cancer, vol. 38, No. 4, pp. 1485-1493 (Oct. 1976).

Merlini, G. and Bellotti, V., "Molecular Mechanisms of Amyloidosis," The New England Journal of Medicine, vol. 349; No. 6; 583-596 (2003).
Mills, et al., Characterization of Monoclonal Antibodies that Inhibit CD38 Adp-ribosyl Cyclase Activity, LSSURP HLB Program, Department of Pharmacology, University of Minnesota, 2007.
Mills, E.N.C. et al., "The prevalence, cost and basis of food allergy across Europe," Allergy, vol. 62; 717-722 (2007).
Mikhael et al., "Cyclophosphamide-Bortezomib-Dexamethasone (CYBORD) Produces Rapid and Complete Hematological Response in Patients with AL Amyloidosis," Blood 119:4391-94 (Year: 2012).
Mohammad et al., "The Addition of Bryostatin 1 to Cyclophosphamide, Doxorubicin, Vincristine, and Prednisone (CHOP) Chemotherapy Improves Response in a CHOP-resistant Human Diffuse Large Cell Lymphoma Xenograft Model," Clinical Cancer Research, vol. 6, 4950-4956 (Dec. 2000).
Morrison, et al., "Chimeric human antibody molecules: Mouse antigen-binding domains with human constant region domains," Proceedings of the National Academy of Science USA, vol. 81; 6851-6855 (1984).
Mrowietz, "Treatment of Severe Psoriasis with Anti-CD25 Monoclonal Antibodies," Arch. Dermatology, 136: 675-676 (2000).
Mukherjee, et al., "Production and Characterization of Protective Human Antibodies against Shiga Toxin 1," Infection and Immunity, 70(10): 5896-5899 (2012).
Muyldermans, "Single domain camel antibodies: current status," Reviews in molecular Biotechnology, 74: 277-302 (2001).
Muyldermans, et al., "Recognition of antigens by single-domain antibody fragments: the superfluous luxury of paired domains," Trends in Biochemical Sciences, 26(4): 230-235 (2001).
Najjar et al., "Abstract P227: Accumulation of MDSC Subsets in Renal Cell Carcinoma Correlates with Grade and Progression Free Survival, and is Associated with Intratumoral Expression of IL-1β, IL-8 and CXCL5," Journal for Immunotherapy of Cancer, Nov. 6, 2014, vol. 2, p. 110-112.
Nijhof, I.S. et al., Preclinical Evidence for the Therapeutic Potential of CD38-Targeted Immuno-Chemotherapy in Multiple Myeloma Patients Refractory to Lenalidomide and Bortezomib. Clin Cancer Res., vol. 21, No. 12, pp. 2802-2810 (2014).
Nijhof, et al.,"Modulation of CD 38 Expression Levels on Multiple Myeloma Tumor Cells By All-Trans Retinoic Acid Improves the Efficacy of the Anti-CD 38 Monoclonal Antibody Daratumumab," Blood, American Society of Hematology, US, vol. 124, No. 21, p. 2096, Dec. 6, 2014. (Abstract Only).
Nijhof, I.S. et al., Combination of the anti-CD38 monoclonal antibody daratumumab and all-trans retinoic acid (Abstract in Proceedings of the AACR Special Conference on Hematologic Malignancies: Translating Discoveries to Novel Therapies). Clin Cancer Res, Sep. 20, 2014, vol. 21, No. 17 Suppl, pages Abstract A12; Abstract.
Nijhof I.S. et al.: "Upregulation of CD38 expression on multiple myeloma cells by all-trans retinoic acid improves the efficacy of daratumumab", Leukemia, vol. 29, No. 10, ISSN 1476-5551, pp. 2039-2049 (2015).
Nikaido, et al., "Molecular cloning of cDNA encoding human interleukin-2 receptor," Nature, 311: 631-635 (1984).
Offidani et al., "An evidence-based review of ixazomib citrate and its potential in the treatment of newly diagnosed multiple myeloma," OncoTargets and Therapy, vol. 7, pp. 1793-1800, 2014.
Onizuka, et al., "Tumor Rejection by in Vivo Administration of Anti-CD25 (Interleukin-2 Receptor a Monoclonal Antibody," Cancer Research, 59: 3128-3133 (1999).
Orlowski, "The Ubiquitin Proteasome pathway from Bench to Bedside," American Society of Hematology, 220-225 (2005).
Ostberg, et al., "Human and humanized monoclonal antibodies: preclinical studies and clinical experience," Biochemical Society Transactions, 23: 1-6 (1995).
Padlan, et al., "Identification of specificity-determining resides in antibodies," FASEB Journal, 9: 135-139 (1995).
Palumbo, A. et al., "Daratumumab, Bortezomib, and Dexamethasone for Multiple Myeloma," The New England Journal of Medicine, vol. 375; No. 8; 754-766 (2016).

(56) References Cited

OTHER PUBLICATIONS

Palumbo, A. et al., "Daratumumab, Bortezomib, and Dexamethasone for Multiple Myeloma," The New England Journal of Medicine, vol. 375; No. 8; 754-766; Suppl. Material: the protocol; total pp. 119 (2016).
Park, S. et al., "Successful Treatment by Rituximab of an Ebv-Related Lymphoma after Autologous Transplantation for Angioimmunoblastic T-Cell Lymphoma," International Journal of Hematol., vol. 76; Suppl. 1; 118; Abstract No. P340 (2002).
Parren et al., "HuMax-CD38, a new human CD38 monoclonal antibody, effectively mediates killing of multiple myeloma and plasma cell leukemia cells," American Society of Hematology 47th annual meeting, Atlanta, Georgia, USA, Dec. 10-13, 2005 (Abstract).
Parren, et al., HuMax-CD38, Myconos, Jun. 26, 2006.
Parren, et al., HuMax-CD38, Torino, Jun. 8-10, 2006.
Pascual, et al., "Anti-interleukin-2 receptor antibodies: basiliximab and daclizumab," Nephrology Dial. Transplant, 16: 1756-1760 (2001).
Patel, J.P., "Prognostic Relevance of Integrated Genetic Profiling in Acute Myeloid Leukemia," The New England Journal of Medicine, vol. 366; No. 12; 1079-1089 (2012).
Patton, D.T. et al., "The P13K p110δ Regulates Expression of CD38 on Regulatory T Cells," PLOS one, vol. 6; No. 3; e17359; 8 pages (2011).
Paul, M.D., "Fundamental Immunology," Chapter 9, Raven Press, New York, 3rd ed., 292-295 (1993).
Peipp, et al., "Fully Human CD38 Antibodies Efficiently Trigger ADCC and CDC of Multiple Myeloma Cell Lines and Primary Tumor Cells (Poster)," Blood, vol. 106(11): 944A, 47th Annual Meeting of the American Society of Hematology, 2005; published (Nov. 16, 2005).
Peipp, et al., Fully Human CD38 Antibodies Efficiently Trigger ADCC and CDC of Multiple Myeloma and Plasma Cell Leukemia Cells (Poster 2) Conference proceedings, poster presentation at the 2005 Annual Meeting of the American Society of Hematology, (Dec. 12, 2005).
Peipp, et al., 47th Annual Meeting of the American Society of Hematology, Atlanta, GA, Dec. 10-13, 2005. (Meeting Abstract).
Peng, et al., "Oncolytic measles viruses displaying a single-chain antibody against CD38, a myeloma cell marker," Blood, 101, 2557-2562 (2003).
Phase ½ Dose Escalation and Efficacy Study of Anti-CD38 Monoclonal Antibody in Patients With Selected CD38+ Hematological Malignancies, First posted Mar. 10, 2010, ClinicalTrials.gov. identifier No. NCT01084252.
Prosniak, M. et al.: "Development of a Cocktail of Recombinant-Expressed Human Rabies Virus-Neutralizing Monoclonal Antibodies for Postexposure Prophylaxis of Rabies," The Journal of Infectious Diseases, vol. 187; 53-56 (2003).
Rai, S. et al., "Successful Allogeneic Hematopoietic Stem Cell Transplantation in a Young Patient with Richter Syndrome Presenting with Chronic Lymphocytic Leukemia and Diffuse Large B-Cell Lymphoma with Different Cell Origins," Intern Med, vol. 52; 273-276 (2013).
Richardson, et al., "Daratumumab," Drugs of the Future, 38(8): 545-554 (2013).
Rituxan Hycela Label, "Highlights of prescribing information. Rituxan Hycela™ (rituximab and hyaluronidase human) injection, for subcutaneous use," 32 pages (Jun. 2017).
Sachchithanantham, S. et al., "Use of Plasma Cell Immunophenotype as Prognostic Markers in Patients with Systemic AL Amyloidosis," Blood, vol. 122; p. 3120 (2013).
Sagaster, V. et al., "Bortezomib in relapsed multiple myeloma: response rates and duration of response are independent of a chromosome 13q-deletion," Leukemia, vol. 21; 164-168 (2007).
Saito, M. et al., "A Case of Retroperitoneal Extramedullary Plasmacytoma," Acta Urol. Jpn., vol. 49; 735-739 (2003).
Salar et al., "Comparison of Subcutaneous Versus Intravenous Administration of Rituximab As Maintenance Treatment for Follicular Lymphoma: Results From a Two-Stage, Phase IB Study," Journal of Clinical Oncology, vol. 32, No. 17, pp. 1782-1791, (Jul. 10, 2014).
Sanchez-Gonzalez et al., "Rituximab subcutaneous in B-Cell non-Hodgkin lymphoma: clinical experience in a single center," Leukemia & Lymphoma, vol. 59, No. 4, pp. 1019-1021 (2018).
San-Miguel, J. et al., "Efficacy by cytogenetic risk status for daratumumab in combination with lenalidomide and dexamethasone or bortezomib and dexamethasone in relapsed or refractory multiple myeloma," EHA22; EHA Learning Center; Abstract; 4 pages (2017).
San-Miguel, J., "New approaches to myeloma treatment in 2017," EHA Learning Center; Abstract; 4 pages (2017).
Schonland, S., et al., "Detection and Charaterization of Plasma Cell and B Cell Clones in Patients with Systemic Light Chain Amyloidosis Using Flow Cytometry," Blood, vol. 142, p. 2068 (2014).
Sher, T. et al., "First report of safety and efficacy of daratumumab in 2 cases of advanced immunoglobulin light chain amyloidosis," Blood, vol. 128; No. 15; 1987-1989 (2016).
Shields, et al., "High Resolution mapping of the binding site on human IgG1 for FcγRi, FcγRII, FcγRIII, and FcRn and design of IgG1 variants with improved binding to the FcγR," J. Biol. Chem., vol. 276, No. 9, pp. 6591-6604, (2001).
Shpilberg, et al., "Subcutaneous administration of rituximab (MabThera) and trastuzumab (Herceptin) using hyaluronidase," British Journal of Cancer, vol. 109, pp. 1556-1561, 2013.
Shubinsky, et al., "The CD38 Lymphocyte Differentiation Marker: New Insight into Its Ectoenzymatic Activity and Its Role as a Signal Transducer," Immunity, 7: 315-324 (1997).
Sicherer, S.H. and Sampson, H.A., "Food allergy: Epidemiology, pathogenesis, diagnosis, and treatment," J. Allergy Clin Inmmunol, vol. 133; 291-307 (2014).
Skeel, Handbook of Cancer Gliemotherapy, 3rd edition, Little, Brown & Co., pp. 330-350 (1991).
Smithson, G. et al., "TAK-079 is a high affinity monoclonal antibody that effectively mediates CD38+ cell depletion," Journal of Immunol., vol. 198; Suppl. 1; 224.20; Abstract (2017).
Sonneveld, P. and Annemiek Broijl, "Treatment of Relapsed and Refractory Multiple Myeloma," Review Article, Leaders in Hematology, review series, Haematologica, 101(4):396-406 (2016).
Spencer, A et al., "Daratumumab plus bortezomib and dexamethasone versus bortezomib and dexamethasone in relapsed or refractory multiple myeloma: updated analysis of CASTOR," Haematologica, vol. 103; No. 12; 2079-2087 (2018).
Strome, S.E. et al., "A Mechanistic Perspective of Monoclonal Antibodies in Cancer Therapy Beyond Target-Related Effects," The Oncologist, vol. 12; 1084-1095 (2007).
Swaika, A. et al., "Current state of anti-PD-L1 and anti-PD-1 agents in cancer therapy," Molecular Immunology, vol. 67; 4-17 (2015).
Tabernero, et al., "Adult precursor B-ALL with BCR/ABL gene rearrangements displays a unique 20mmunophenotyped based on the pattern of CD10, CD34, CD13, and CD38 expression," Leukemia, vol. 15, No. 3, pp. 406-414, (2001).
Talmadge, J.E. and Gabrilovich, D.I, "History of myeloid-derived suppressor cells," Nature Reviews, vol. 13; 739-752 (2013).
Terhorst, et al., "Biochemical Studies of the Human Thymocyte Cell-Surface Antigens T6, T9 and T10," Cell, 23: 771-780 (1981).
The Cancer Genome Atlas Research Network et al., "Genomic and Epigenomic Landscapes of Adult De Novo Acute Myeloid Leukemia," N. Engl. J. Med, vol. 368; No. 22; 2059-2074 (2013).
Topalian, S.L., et al., "Immune Checkpoint Blockade: A Common Denominator Approach to Cancer Therapy," Cancer Cell, vol. 27; 450-461 (2015).
Tzartos, S.J., et al., "Epitope Mapping by Antibody Competition," Methods in Molecular Biology, vol. 66; 55-66 (1996).
Usmani, et al., "Clinical efficacy of daratumumab monotherapy in patients with heavily pretreated relapsed or refractory multiple myeloma," Blood, vol. 128, No. 1, pp. 37-44, (May 23, 2016).
Usmani, S.Z. et al., "Efficacy of Daratumumab, Lenalidomide, and Dexamethasone Versus Lenalidomide and Dexamethasone in Relapsed or Refractory Multiple Myeloma Patients with 1 to 3 Prior Lines of Therapy: Updated Analysis of Pollux," Blood, vol. 128; No. 22; 1151; 10 pages (2016).

(56) References Cited

OTHER PUBLICATIONS

Usmani, S.Z. et al., "Open-Label, Multicenter, Dose Escalation Phase 1b Study to Assess the Subcutaneous Delivery of Daratumumab in Patients (pts) with Relapsed or Refractory Multiple Myeloma," Blood, vol. 128; No. 22; 1149 (2016).

Usmani, S.Z. et al., "Subcutaneous delivery of daratumumab in relapsed or refractory multiple myeloma," Blood, vol. 134; No. 8; 668-677 (2019).

Vadjos, et al., "Comprehensive Functional Maps of the Antigen-binding Site of an Anti-ErbB2 Antibody Obtained with Shotgun Scanning Mutagenesis," Journal of Molecular Biology, 320: 415-428 (2002).

Van Bueren, et al., "Direct In Vitro Comparison of Daratumumab With Surrogate Analogs of Anti-CD38 Antibodies," New Evidence Oncology Issue, Apr. 2015 [retrieved on Feb. 3, 2016] Retrieved from the Internet: URL: Http:///www.newevidence.com/oncology/direct-in-vitro-comparison-of-daratumumab-with-surrogate-analogs-of-anti-cd38-antibodies>.

Van de Donk et al., "Monoclonal antibodies targeting CD38 in hematological malignancies and beyond," Immunological Reviews, vol. 270, pp. 95-112, (2016).

Venner et al., "Cyclophosphamide, bortezomib, and dexamethasone therapy in AL amyloidosis is associated with high clonal response rates and prolonged progression-free survival," Blood, vol. 119, No. 9, pp. 4387-4390, (2012).

Vorre, et al., "Multiple Daratumumab Abstracts to be Presented at EHA," Array Diagnostica, Abstract Only (2014).

Wagner, V., et al., "Preclinical Efficacy of Sepantronium Bromide (YM155) in multiple myeloma is conferred by down regulation of Mcl-1," Oncotarget, 5(21): 10237-10250 (2014).

Wagner et al., Survivin in Multiple Myeloma: Prognostic and Therapeutic Implications, vol. 118, Article 137, 2011 (Abstract Only).

Wang, L. et al., "VISTA, a novel mouse Ig superfamily ligand that negatively regulates T cell responses," J. Exp. Med., vol. 208; No. 3; 577-592 (2011).

WCJ van de Donk, "A Phase 1 and Phase 2 Study of Daratumumab in Combination With All-Trans Retinoic Acid in Relapsed/Refractory Multiple Myeloma," Clinical Trials.gov Identification No. NCT02751255; (First posted Apr. 26, 2016).

Wei, W. et al., "Roles and mechanisms of the CD38/cyclic adenosine diphosphate ribose/Ca2+ signaling pathway," World Journal of Biological Chemistry, vol. 5; No. 1; 58-67 (2014).

Weisel, K.C. et al., "Efficacy of daratumumab in combination with lenalidomide plus dexamethasone (DRd) or bortezomib plus dexamethasone (RVd) in relapsed or refractory multiple myeloma (RRMM) based on cytogenetic risk status," Journal of Clinical Oncology, vol. 35; No. 15; 8006; Abstract (2017).

Williams, B.A. et al., "Antibody Therapies for Acute Myeloid Leukemia: Unconjugated, Toxin-Conjugated, Radio-Conjugated and Multivalent Formats," Journal of Clinical Medicine, vol. 8; No. 1261; 31 pages (2019).

Ye et al, "Abstract P240: Treg Increases HepG2 Cell Growth by RANK-RANKL pathway." Journal for Immunotherapy of Cancer, vol. 2; Suppl 3; P240 (Nov. 6, 2014).

International Preliminary Report on Patentability dated May 8, 2018 for International Application No. PCT/US2016/59893, entitled "Subcutaneous Formulations of ANTI-CD38 Antibodies and Their Uses".

International Search Report and Written Opinion dated Jan. 24, 2017 for International Application No. PCT/US2016/59893, entitled "Subcutaneous Formulations of ANTI-CD38 Antibodies and Their Uses".

International Preliminary Report on Patentability dated Dec. 26, 2017 for International Application No. PCT/US2016/038702, entitled "Combination Therapies for Heme Malignancies With ANTI-CD38 Antibodies and Sur Vivin Inhibitors".

International Search Report and Written Opinion dated Nov. 29, 2016 for International Application No. PCT/US2016/038702, entitled "Combination Therapies for Heme Malignancies With ANTI-CD38 Antibodies and Sur Vivin Inhibitors".

International Preliminary Report on Patentability dated Mar. 14, 2017 for International Application No. PCT/US2015/048899, entitled "Combination Therapies With ANTI-CD38 Antibodies".

International Search Report and Written Opinion dated Apr. 8, 2016 for International Application No. PCT/US2015/048899, entitled "Combination Therapies With ANTI-CD38 Antibodies".

International Preliminary Report on Patentability dated Nov. 21, 2017 for International Application No. PCT/US2016/033544, entitled "ANTI-CD38 Antibodies for Treatment of Light Chain Amyloidosis and Other CD38- Positive Hematological Malignancies".

International Search Report and Written Opinion dated Oct. 24, 2016 for International Application No. PCT/US2016/033544, entitled "ANTI-CD38 Antibodies for Treatment of Light Chain Amyloidosis and Other CD38- Positive Hematological Malignancies".

International Preliminary Report on Patentability dated Jun. 6, 2016 for International Application No. PCT/US2015/063371, entitled "ANTI-CD38 Antibodies for Treatment of Acute Myeloid Leukemia".

International Search Report and Written Opinion dated Feb. 19, 2016 for International Application No. PCT/US2015/063371, entitled "ANTI-CD38 Antibodies for Treatment of Acute Myeloid Leukemia".

International Preliminary Report on Patentability dated Dec. 26, 2017 for International Application No. PCT/US2016/039165, entitled "Immune Modulation and Treatment of Solid Tumors With Antibodies That Specifically Bind CD38".

International Search Report and Written Opinion dated Oct. 14, 2016 for International Application No. PCT/US2016/039165, entitled "Immune Modulation and Treatment of Solid Tumors With Antibodies That Specifically Bind CD38".

International Preliminary Report on Patentability dated Sep. 6, 2016 for International Application No. PCT/US2015/017425, entitled "ANTI-CD38 Antibodies for Treatment of Acute Lymphoblastic Leukemia".

International Search Report and Written Opinion dated Sep. 21, 2015 for International Application No. PCT/US2015/017425, entitled "ANTI-CD38 Antibodies for Treatment of Acute Lymphoblastic Leukemia".

International Preliminary Report on Patentability dated Jan. 10, 2019 for International Application No. PCT/EP2017/066063, entitled "Treatment Of IgE-MEDIATED Diseases With Antibodies That Specifically Bind CD38".

International Search Report and Written Opinion dated Sep. 25, 2017 for International Application No. PCT/EP2017/066063, entitled "Treatment Of IgE-Mediated Diseases With Antibodies That Specifically Bind CD38".

International Preliminary Report on Patentability dated May 14, 2020 for International Application No. PCT/US2018/058561, entitled "Methods of Treating High Risk Multiple Myeloma".

International Search Report and Written Opinion dated Feb. 12, 2019 for International Application No. PCT/US2018/058561, entitled "Methods of Treating High Risk Multiple Myeloma".

International Search Report and Written Opinion dated Apr. 24, 2020 for International Application No. PCT/US2019/056838, entitled "Method of Providing Subcutaneous Administration of Anti-CD38 Antibodies".

International Preliminary Report on Patentability dated Sep. 6, 2016 for International Application No. PCT/US2015/017420, entitled "Combination Therapies With ANTI-CD38 Antibodies".

International Search Report and Written Opinion dated Jul. 8, 2015 for International Application No. PCT/US2015/017420, entitled "Combination Therapies With ANTI-CD38 Antibodies".

Intellectual Property Office of Singapore Written Opinion dated Apr. 17, 2018 for Application No. 11201701867S, entitled "Combination Therapies with Anti-CD38 Antibodies".

Supplementary European Search Report dated Feb. 21, 2018 for European Application No. EP 15839752 , entitled "Combination Therapies with Anti-CD38 Antibodies".

Non Final Office Action for U.S. Appl. No. 15/340,290 dated Nov. 20, 2017.

Final Office Action for U.S. Appl. No. 15/340,290 dated May 16, 2018.

(56) References Cited

OTHER PUBLICATIONS

Non Final Office Action for U.S. Appl. No. 15/340,290 dated Oct. 10, 2018.
Non Final Office Action for U.S. Appl. No. 15/366,474 dated Nov. 20, 2017.
Final Office Action for U.S. Appl. No. 15/366,474 dated May 16, 2018.
Applicant Initiated Interview for U.S. Appl. No. 15/366,474 dated Sep. 17, 2018.
Non Final Office Action for U.S. Appl. No. 15/366,474 dated Oct. 11, 2018.
Non Final Office Action for U.S. Appl. No. 15/189,577 dated Oct. 31, 2017.
Final Office Action for U.S. Appl. No. 15/189,577 dated Apr. 13, 2018.
Non Final Office Action for U.S. Appl. No. 15/189,577 dated Sep. 28, 2018.
Non Final Office Action for U.S. Appl. No. 14/847,428 dated Sep. 23, 2016.
Non Final Office Action for U.S. Appl. No. 15/386,391 dated Jun. 18, 2018.
Non Final Office Action for U.S. Appl. No. 15/160,476 dated Sep. 15, 2017.
Non Final Office Action for U.S. Appl. No. 15/160,476 dated Nov. 5, 2018.
Final Office Action for U.S. Appl. No. 15/160,476 dated Apr. 23, 2018.
Non Final Office Action for U.S. Appl. No. 14/956,890 dated Nov. 25, 2016.
Final Office Action for U.S. Appl. No. 14/956,890 dated Jul. 24, 2018.
Non Final Office Action for U.S. Appl. No. 15/340,214 dated May 16, 2018.
Non Final Office Action for U.S. Appl. No. 14/629,965 dated Dec. 21, 2015.
Final Office Action for U.S. Appl. No. 14/629,965 dated Apr. 29, 2016.
Notice of Allowance for U.S. Appl. No. 14/629,965 dated Apr. 13, 2017.
Non Final Office Action for U.S. Appl. No. 15/445,225 dated Jun. 29, 2018.
Final Office Action for U.S. Appl. No. 15/445,225 dated Dec. 17, 2018.
Non Final Office Action for U.S. Appl. No. 15/651,333 dated Sep. 27, 2018.
Final Office Action for U.S. Appl. No. 15/386,391 dated Dec. 28, 2018.
Final Office Action for U.S. Appl. No. 14/956,890 dated Jan. 14, 2019.
Notice of Allowance for U.S. Appl. No. 15/651,333 dated Feb. 21, 2019.
Notice of Allowance for U.S. Appl. No. 15/189,577 dated Mar. 5, 2019.
Final Office Action for U.S. Appl. No. 15/340,290 dated Mar. 11, 2019.
Notice of Allowance for U.S. Appl. No. 15/386,391 dated Mar. 29, 2019.
Notice of Allowance for U.S. Appl. No. 15/340,290 dated May 22, 2019.
Notice of Allowance for U.S. Appl. No. 15/651,333 dated May 31, 2019.
Final Office Action for U.S. Appl. No. 15/160,476 dated Jun. 14, 2019.
Notice of Allowance for U.S. Appl. No. 15/386,391 dated Jul. 30, 2019.
Non-Final Office Action for U.S. Appl. No. 14/956,890 dated Jul. 30, 2019.
Notice of Allowance for U.S. Appl. No. 15/189,577 dated Sep. 12, 2019.
Notice of Allowance for U.S. Appl. No. 15/651,333 dated Oct. 9, 2019.
Notice of Allowance for U.S. Appl. No. 15/386,391 dated Nov. 18, 2019.
Notice of Allowance for U.S. Appl. No. 15/189,577 dated Dec. 19, 2019.
Non Final Office Action for U.S. Appl. No. 15/160,476 dated Dec. 20, 2019.
Final Office Action for U.S. Appl. No. 14/956,890 dated Jan. 7, 2020.
Non-Final Office Action for U.S. Appl. No. 15/798,670 dated Jan. 22, 2020.
English translation of Office Action for JP Application No. 2016-554350, dated Nov. 27, 2018.
Notice of Allowance for U.S. Appl. No. 15/189,577 dated Mar. 31, 2020.
Notice of Allowance for U.S. Appl. No. 15/160,476 dated May 4, 2020.
Notice of Allowance for U.S. Appl. No. 16/380,994 dated May 12, 2020.
Notice of Allowance for U.S. Appl. No. 16/460,754 dated May 18, 2020.
Notice of Allowance for U.S. Appl. No. 14/956,890 dated Jul. 29, 2020.
Non-Final Office Action for U.S. Appl. No. 15/798,670 dated Aug. 7, 2020.
Notice of Allowance for U.S. Appl. No. 16/380,994 dated Aug. 12, 2020.
Non-Final Office Action for U.S. Appl. No. 16/162,355 dated Aug. 13, 2020.
Non-Final Office Action for U.S. Appl. No. 16/177,239 dated Aug. 24, 2020.
Notice of Allowance for U.S. Appl. No. 16/460,754 dated Sep. 10, 2020.
ASH Clinical News, "Is Daratumumab Plus Lenalidomide-Dexamethasone a New Standard for Transplant-Ineligible Myeloma," Dated Jan. 1, 2019, Retrieved from Internet URL: https://www.ashclinicalnews.org/on-location/ash-annual-meeting/daratumumab-plus-lenalidomid; Retrieved Oct. 28, 2022 (2 pages).
Avet-Loiseau, H. et al., "Evaluation of Minimal Residual Disease (MRD) in Relapsed/Refractory Multiple Myeloma (RRMM) Patients Treated with Daratumumab in Combination with Lenalidomide Plus Dexamethasone or Bortezomib Plus Dexamethasone," Blood, vol. 128; No. 22; 246; 7 pages (2016).
Bauer, Fromming, Fuhrer, "Lehrbuch der Pharmazeutischen Technologie"8th Edition, Wissenschaftliche Verlagsgesellschaft Stuttgart, Chapter 9; 238-243 (2006). concise explanation met by submission of the enclosed Opponent's submission filed by Dr. Markus Breuer cited as Other Document 134).
Bittner, B. et al., "Development of a Subcutaneous Formulation for Trastuzumab—Nonclinical and Clinical Bridging Approach to the Approved Intravenous Dosing Regimen," Arzneimittelforschung, vol. 62; 401-409 (2012).
Bittner, B. et al., "Non-Clinical Pharmacokinetic /Pharmacodynamic and Early Clinical Studies Supporting Development of a Novel Subcutaneous Formulation for the Monoclonal Antibody Rituximab," Drug Res., vol. 64; 569-575 (2014).
Bittner, B. et al., "Subcutaneous Administration of Biotherapeutics: An Overview of Current Challenges and Opportunities," BioDrugs, vol. 32; 425-440 (2018).
Bookbinder, L.H. et al., "A recombinant human enzyme for enhanced interstitial transport of therapeutics," Journal of Controlled Release, vol. 114; 230-241 (2006).
CAS Registry Results, dated Oct. 9, 2020, Registry No. 757971-58-7, "36-482-Hyaluronoglucosaminidase PH20 (human)," 6 pages.
Chari, A., et al., "Subcutaneous Daratumumab (DARA) in Patients (Pts) With Relapsed or Refractory Multiple Myeloma (RRMM): Part 2 Update of the Open-label, Multicenter, Dose-escalation Phase 1b Study (PAVO)", Poster Presented at the Annual Meeting of the American Society of Clinical Oncology (ASCO); June Jan. 5, 2018; Chicago, Illinois.
Chaulagain, C.P. et al., "Pre-clinical translational studies of daratumumab in patients with myeloma or AL amyloidosis undergoing autologous

(56) References Cited

OTHER PUBLICATIONS hematopoietic stem cell transplantation (SCT)," Journal of Clinical Oncology, May 20, 2015, vol. 33, No. 15 suppl., pp. 8587-8587.
CHMP Assessment Report for Herceptin (trastuzumab), 70 pages (2013).
CHMP Assessment Report for Mabthera (rituximab), 103 pages (2014).
Chung, C.H., "Managing Premedications and the Risk for Reactions to Infusional Monoclonal Antibody Therapy," The Oncologist, vol. 13; 725-732 (2008).
ClinicalTrials.gov, "Daratumumab (HuMax-CD38) Safety Study in Multiple Myeloma," Identifier: NCT00574288; Latest version posted: Apr. 27, 2018 (10 pages).
Clinicaltrials.gov, "An Investigational Immuno-Therapy Study to Determine the Safety and Effectiveness of Nivolumab and Daratumumab in Patients with Multiple Myeloma," Identifier: NCT01592370; Latest version posted: Jun. 18, 2021 (10 pages).
Clinicaltrials.gov, "History of Changes for Study: NCT02252172: Study Comparing Daratumumab, Lenalidomide, and Dexamethasone With Lenalidomide and Dexamethasone in Participants With Previously Untreated Multiple Myeloma," U.S. National Library of Medicine, ClinicalTrials.gov Archive, Oct. 17, 2017 (24 pages).
Clinicaltrials.gov, "History of Changes for Study: NCT02519452: A Study of Daratumumab With the Addition of Recombinant Human Hyaluronidase (rHuPH20) for the Treatment of Participants with Relapsed or Refractory Multiple Myeloma," U.S. National Library of Medicine, ClinicalTrials.gov Archive, Dec. 3, 2020 (12 pages).
Clinicaltrials.gov, "A Study of Daratumumab with the Addition of Recombinant Human Hyaluronidasc (rHuPH20) for the Treatment of Participants with Relapsed or Refractory Multiple Myeloma," Identifier: NCT02519452; First Received: Aug. 6, 2015 (5 pages).
Colson, K., "Treatment-related symptom management in patients with multiple myeloma: a review," Support Care Cancer, vol. 23; 1431-1445 (2015).
Common Terminology Criteria for Adverse Events (CTCAE), Version 4.03, U.S. Department of Health and Human Services, 4 pages (2010).
Complete Specification for Indian Application No. 4718/CHENP/2007; published on Jan. 11, 2008 (225 Pages).
Consolidated list of references from Opposition in parent patent EP No. 3370770, 4 pages; Feb. 24, 2022.
Darzalex, Highlights and Prescribing Information, FDA Label, 24 pages (2015).
Darzalex, Highlights and Prescribing Information, FDA Label, 32 pages (2018).
Davies, A. et al., "Pharmacokinetics and safety of subcutaneous rituximab in follicular lymphoma (SABRINA): stage 1 analysis of a randomised phase 3 study," The Lancet, vol. 15; 343-352 (2014).
Dimopoulos, M.A. et al., "Daratumumab, Lenalidomide, and Dexamethasone for Multiple Myeloma," The New England Journal of Medicine, vol. 375; No. 14; 1319-1331 (2016); Suppl. Material: the protocol; total pp. 111 (2016).
Dimopoulos, M.A. et al., "Daratumumab plus pomalidomide and dexamethasone versus pomalidomide and dexamethasone alone in previously treated multiple myeloma (APOLLO): an open-label, randomised, phase 3 trial," Lancet Oncol, vol. 22; 801-812 (2021).
Doessegger, L. and Banholzer, M.L., "Clinical development methodology for infusion-related reactions with monoclonal antibodies," Clinical & Translational Immunology, vol. 4; e39; 9 pages (2015).
Drach, J. et al., "Retinoic Acid-induced Expression of CD38 Antigen in Myeloid Cells is Mediated through Retinoic Acid Receptor-$\alpha^1$," Cancer Research, vol. 54; 1746-1752 (1994).
Durie, B.G.M. et al., "International Uniform Response Criteria for Multiple Myeloma," Leukemia, vol. 20; 1467-1473 (2006).
European Medicines Agency, Summary of Product Characteristics for Rituximab; 153 pages; Oct. 30, 2009, https://www.ema.europa.eu/en/documents/product-information/mabthera-epar-product-information_en.pdf.
European Union Clinical Trials Register Clinical Trials Register, EudraCT No. 2014-002272-88; Title: "A Phase 3, Randomized, Controlled, Open-label Study of VELCADE (Bortezomlb) Melphalan-Prednisone (VMP) Compared to Daratumumab In Combination with VMP (D-VMP), In Subjects with Previously Untreated Multiple Mycloma who are Incllgible for High-dosc Therapy," 6 pages (2015).
European Union Clinical Trials Register Clinical Trials Register, EudraCT No. 2014-002273-11; Title: "A Phase 3 Study Comparing Daratumumab, Lenalidomide, and Dexamethasone (DRd) vs Lenalidomide and Dexamethasone (Rd) In Subjects with Previously Untreated Multiple Myeloma who are Ineligible for High Dose Therapy," 7 pages (2015).
European Union Clinical Trials Register Clinical Trials Register, EudraCT No. 2013-005525-23; Title: "Phase 3 Study Comparing Daratumumab, Lenalidomide, and Dexamethasone (DRd) vs Lenalidomide and Dexamethasone (Rd) in Subjects with Relapsed or Refractory Multiple Myeloma," 7 pages (2014).
European Union Clinical Trials Register Clinical Trials Register, EudraCT No. 2014-000255-85; Title: "Phase 3 Study Comparing Daratumumab, Bortezomlb and Dexamethasone (DVd) vs Bortezomib and Dexamethasone (Vd) In Subjects With Relapsed or Refractory Multiple Mycloma," 6 pages (2014).
Facon, T. et al., "Phase 3 Randomized Study of Daratumumab Plus Lenalidomide and Dexamethasone (D-Rd) Versus Lenalidomide and Dexamethasone (Rd) in Patients with Newly Diagnosed Multiple Myeloma (NDMM) Ineligible for Transplant (MAIA)," Blood, vol. 132 (Suppl 1); 8 Pages (2018).
Faiman, B. et al., "Steroid-Associated Side Effects in Patents with Multiple Myeloma: Consensus Statement of the IMF Nurse Leadership Board," Clinical Journal of Oncology Nursing, vol. 12; No. 3; 53-63 (2008).
Frost, G.I., "Recombinant human hyaluronidase (rHuPH20): an enabling platform for subcutaneous drug and fluid administration," Expert Opinion Drug Deliv., vol. 4; No. 4; 427-440 (2007).
Gay, F. and Palumbo, A., "Management of Older Patients with Multiple Myeloma," Blood Reviews, vol. 25; 65-73 (2011).
Goel, M. et al., "Plasticity within the Antigen-Combining Site May Manifest as Molecular Mimicry in the Humoral Immune Response," The Journal of Immunology, vol. 173; 7358-7367 (2004).
Haller, M.F., "Converting Intravenous Dosing to Subcutaneous Dosing," Pharmaceutical Technology, 118-132 (2007).
Halozyme, "Halozyme Therapeutics Reports Selection of First Product Candidate Under Janssen Collaboration," Press Release, 4 pages (2015).
Hamizi, S. et al., "Subcutaneous trastuzumab: development of a new formulation for treatment of HER2-positive early breast cancer," OncoTargets and Therapy, vol. 6; 89-94 (2013).
Herceptin, Highlights and Prescribing Information, FDA Label, 33 pages (1998).
Highlights of Prescribing Information, Rituxan, 53 pages (1997).
Highlights of Prescribing Information, Rituxan (rituximab) injection, 44 pages (1997).
Hydase, Highlights and Prescribing Information, FDA Label, 6 pages (2005).
Hylenex, Highlights and Prescribing Information, FDA Label, 9 pages (2005).
Jaccard, A. et al., "Efficacy of bortezomib, cyclophosphamide and dexamethasone in treatment-naïve patients with high-risk cardiac AL amyloidosis (Mayo Clinic stage III)," Haematologica, vol. 99; No. 9; 1479-1485 (2014).
Jackisch, C. et al., "Subcutaneous Administration of Monoclonal Antibodies in Oncology," Geburtsh Frauenhelk, vol. 74; 343-349 (2014).
Janssen Initiates Rolling Submission of Biologic License Application (BLA) for daratumumab with U.S. FDA for the Treatment of Multiple Myeloma, News Release, 3 pages (2015).
Janssen to Demonstrate Breadth of Oncology Portfolio with 41 Clinical Data Presentations at the 2014 American Society of Hematology (ASH) Annual Meeting [online], Nov. 6, 2014, Internet:<URL: https://www.jnj.com/media-center/press-releases/janssen-to-demonstrate-breadth-of-oncology-portfolio-with-41-clinical-data-presentations-at-the-2014-american-society-of-hematology-ash-annual-mccting>; 8 pages.

(56) References Cited

OTHER PUBLICATIONS

Janssen Submits Marketing Authorisation Application for Daratumumab for European Patients with Heavily Pre-treated Multiple Myeloma, Janssen-Cilag International NV; 7 pages (2015).
Jolles, S., "Hyaluronidase facilitated subcutaneous immunoglobulin in primary immunodeficiency," Immuno Targets and Therapy, vol. 2; 125-133 (2013).
Kang, W. et al., "Inference of synergy/antagonism between anti-cancer drugs from the pooled analysis of clinical trials," BMC Medical Research Methodology, vol. 13; No. 77; 8 pages (2013).
Khagi, Y. and Mark, T., "Potential role of daratumumab in the treatment of multiple myeloma," Onco Targets and Therapy, 1095-1100 (2014).
Khan, T. and Salunke, D.M., "Adjustable Locks and Flexible Keys: Plasticity of Epitope-Paratope Interactions in Germline Antibodies," The Journal of Immunology, vol. 192; 5398-5405 (2014).
Kim, H. et al., "Overview of methods for comparing the efficacies of drugs in the absence of head-to-head clinical trial data," Br. J. Clin. Pharmacol., vol. 77; No. 1; 116-121 (2013).
Knowles, S.P. et al., "Safety of recombinant human hyaluronidase PH20 for subcutaneous drug delivery," Expert Opinion on Drug Delivery, vol. 18; No. 11; 1673-1685 (2021).
Kyle, R.A. and Rajkumar, S.V., "Criteria for diagnosis, staging, risk stratification and response assessment of multiple myeloma," Leukemia, vol. 23; 3-9 (2009).
Kyle, R.A. et al., "Clinical Course and Prognosis of Smoldering (Asymptomatic) Multiple Myeloma," The New England Journal of Medicine, vol. 356; 2582-2590 (2007).
Kyle, R.A. et al., "Review of 1027 Patients with Newly Diagnosed Multiple Myeloma," May Clinic Proc., vol. 78; 21-33 (2003).
Laubach, J.P. et al., "The challenge of cross-trial comparisons using limited data," haematologica, vol. 99; e145; 2 pages (2014).
Lefranc, M. et al., "IMGT unique numbering for immunoglobulin and T cell receptor variable domains and Ig superfamily V-like domains," Developmental & Comparative Immunology, vol. 27; 55-77 (2003).
Lokhorst, H.M. et al., "Targeting CD38 with Daratumumab Monotherapy in Multiple Myeloma," The New England Journal of Medicine, vol. 373; 1207-1219 (2015).
Lokhorst, H.M. et al., "Targeting CD38 with Daratumumab Monotherapy in Multiple Myeloma," The New England Journal of Medicine, vol. 373; 1207-1219 (2015); Supplemental Appendix.
Lonial, S. et al., "Phase II study of daratumumab (DARA) monotherapy in patients with greater than or equal to 3 lines of prior therapy or double refractory multiple myeloma (MM): 54767414MMY2002 (Sirius)," Journal of Clinical Oncology, vol. 33; No. 18 Suppl (2015).
Lonial, S. et al., "Monoclonal antibodies in the treatment of multiple myeloma: current status and future perspectives," Leukemia, vol. 30; 526-535 (2016).
Mahajan, S. et al., "The evolution of stem-cell transplantation in multiple myeloma," Therapeutic Advances in Hematology, vol. 9; No. 5; 123-133 (2018).
Mariuzza, R.A. eet al., "The Structural Basis of Antigen-Antibody Recognition," Ann. Rev. Biophys. Biophys. Chem., vol. 16; 139-159 (1987).
Matcos, M. et al., "Daratumumab plus Bortezomib, Melphalan, and Prednisone for Untreated Myeloma," N England J Med, vol. 378; 518-528 (2018).
Maury, M. et al., "Spray-drying of proteins: effects of sorbitol and trehalose on aggregation and FT-IR amide I spectrum of an immunoglobulin G," European Journal of Pharmaceutics and Biopharmaceutics, vol. 59; 251-261 (2005).
McCudden, C. et al., "Monitoring multiple myeloma patients treated with daratumumab: teasing out monoclonal antibody interference," Clin Chem Lab Med, vol. 54; No. 6; 1095-1104 (2016).
Moreau, P. et al., "Rituximab in CD20 positive multiple myeloma," Leukemia, vol. 21; 835-836 (2007).
Moreau, P. et al., "Practical Considerations for the Use of Daratumumab, a Novel CD38 Monoclonal Antibody, in Myeloma," Drugs, vol. 76; 853-867 (2016).
Nahi, H. et al., "An open-label, dose escalation phase 1b study of subcutaneous daratumumab with recombinant human hyaluronidase in patients with relapsed or refractory multiple myeloma (PAVO)," Journal of Clinical Oncology, vol. 34; No. 15; 4 pages (2016).
Negrin, R., Patient education: Hematopoietic transplantation (bone marrow transplantation) (Beyond the Basics), Retrieved from Internet URL: https://www.uptodate.com/contents/hematopoietic-cell-transplantation-bone-marrow-transplantation-beyond-the-basics, 15 pages; Retrieved on Oct. 27, 2022.
Ocio, E.M. et al., "New drugs and novel mechanisms of action in multiple myeloma in 2013: a report from the International Myeloma Working Group (IMWG)," Leukemia, vol. 28; 525-542 (2014).
Ohaegbulam K C et al.: "Human cancer immunotherapy with antibodies to the PD-1 and PD-L1 pathway", Trends in Molecular Medicine, Jan. 2015; 21 (1): 24-33.
Ortolani, C., "CD38: Antigen: Flow Cytometry of Hematological Malignancies," Blackwell Publishing, 1st Edition, 68-70 (2011).
Palumbo, A. et al., "International Myeloma Working Group guidelines for the management of multiple myeloma patients ineligible for standard high-dose chemotherapy with autologous stem cell transplantation," Leukemia, vol. 23; 1716-1730 (2009).
Palumbo, A. and Anderson, K., "Multiple Myeloma," The New England Journal of Medicine, vol. 364; 1046-1060 (2011).
Patent Assignment Cover Sheet for U.S. Appl. No. 16/380,994, 6 pages; filed Sep. 11, 2019.
Phase 3 COLUMBIA study Investigating a Subcutaneous Formulation of DARZALEX (daratumumab) Showed Non-Inferiority to Intravenous Administration in Patients with Relapsed/Refractory Multiple Myeloma, Chicago, 7 pages (2019).
Phipps, C., et al., "Daratumumab and its potential in the treatment of multiple myeloma: overview of the preclinical and clinical development," Ther. Adv. Hematol., vol. 6; No. 3; 120-127 (2015).
Pivot, X. et al., "Patients' preferences for subcutaneous trastuzumab versus conventional intravenous infusion for the adjuvant treatment of HER2-positive early breast cancer: final analysis of 488 patients in the international, randomized, two-cohort PrefHer study," Annals of Oncology, vol. 25; 1979-1987 (2014).
Poosarla, V.G. et al., "Computational De Novo Design of Antibodies Binding to a Peptide With High Affinity," Biotechnology & Bioengineering, vol. 114; No. 6; 1331-1342 (2017).
Pre-Grant Notice of Opposition filed in Indian Application No. 201617029109, by Indian Pharmaceutical Alliance, dated Feb. 24, 2022 (30 pages).
Preliminary Opinion of the Opposition Division, as cited in EP Opposition against EP Patent No. 3370770; 13 pages; dated Aug. 8, 2022.
Rader, C. et al., "A phage display approach for rapid antibody humanization: Designed combinatorial V gene libraries," Proc. Natl. Acad. Sci, vol. 95; 8910-8915 (1998).
Raj, T.A. et al., "Vincristine sulfate liposomal injection for acute lymphoblastic leukemia," International Journal of Nanomedicine, vol. 8; 4361-4369 (2013).
Rajkumar, S.V. et al., "Consensus recommendations for the uniform reporting of clinical trials: Report of the International Myeloma Workshop Consensus Panel 1," Blood, vol. 117; No. 18; 4691-4695 (2011).
Rituxan (tituximab), Highlights of prescribing information. Rituxan (IV administered Rituximab; 35 pages (1997).
Rosengren, S. et al., Clinical Immunogenicity of rHuPH20, a Hyaluronidase Enabling Subcutaneous Drug Administration, The AAPS Journal, vol. 17; No. 5; 1144-1156 (2015).
Ruberg, E-M. and Frieβ, W., "Sensibel und stressanfällig," Pharmazeutische Zeitung, 156 JG, AUSG. 50; 15 pages (2011). concise explanation met by submission of the enclosed Notice of Opposition filed by Dr. Markus Breuer, cited as Other Document 128).
Rudikoff, S. et al., "Single amino acid substitution altering antigen-binding specificity," Proc. Natl. Acad., col. 79; 1979-1983 (1982).
Ryan, et al., "Potentiation of Anti-Myeloma Activity of Daratumumab with Combination of Cyclophosphamide, Lenalidomide or Bortezomib

(56) References Cited

OTHER PUBLICATIONS via a Tumor Secretory Response That Greatly Augments Macrophage-Induced ADCP," Annual Meeting at the Haematology Association of Ireland, Oct. 15, 2016; 20 pages.
San-Miguel, J., et al., "Subcutaneous Daratumumab in Patients with Relapsed or Refractory Multiple Myeloma: Part 2 Update of the Open-label, Multicenter, Dose Escalation Phase 1b Study (PAVO)", Poster Presented at the 23rd European Hematology Association (EHA) Annual Congress; Jun. 14-17, 2018; Stockholm, Sweden.
Solal-Deligny, P., "Rituximab by subcutaneous route," Expert Rev. Hematol., vol. 8; No. 2; 147-153 (2015).
Sondergeld, P. et al., "Monclonal Antibodies in Myeloma," Clinical Advances in Hematology & Oncology, vol. 13; Issue 9; 599-609 (2015).
Statement on a Nonproprietary Name Adopted by the USAN Council, Hyaluronidase, CAS Registry No. 757971-58-7; 1 page; No date provided.
Strickley, R.G. and Lambert, W.J., "A review of formulations of commercially available antibodies," Journal of Pharmaceutical Sciences, vol. 110; 2590-2608 (2021).
Taussig, D.C. et al., "Anti-CD38 antibody-mediated clearance of human repopulating cells masks the heterogeneity of leukemia-initiating cells," Blood, vol. 112; No. 3; 568-575 (2008).
Usmani, S.Z. et al., "Final analysis of the phase III non-inferiority COLUMBA study of subcutaneous versus intravenous daratumumab in patients with relapsed or refractory multiple myeloma," Haematologica, vol. 107; 2408-2417 (2022).
Wang, W. et al., "Antibody Structure, Instability, and Formulation," Journal of Pharmaceutical Sciences, vol. 96; 1-26 (2007).
Warne, N.W., "Development of high concentration protein biopharmaceuticals: The use of platform approaches in formulation development," European Journal of Pharmaceutics and Biopharmaceutics, vol. 78; 208-212 (2011).
Wasserman, R.L., "Progress in Gammaglobulin Therapy for Immunodeficiency: From Subcutaneous to Intravenous Infusions and Back Again," J. Clin. Immunol., vol. 32 ;1153-1164 (2012).
Wasserman, R.L., "Overview of recombinant human hyaluronidase-facilitated subcutaneous infusion of IgG in primary immunodeficiencies," Immunotherapy, vol. 6; No. 5; 553-567 (2014).
WHO Drug Information, International Nonproprietary Names for Pharmaceutical Substances (INN), Proposed INN: List 101, vol. 23; No. 2; 64 pages (2009).
WHO Drug Information, International Nonproprietary Names for Pharmaceutical Substances (INN), Recommended INN: List 63, 40 pages (2010).
Wu, et al., An Analysis of the Sequences of the Variable Regions of Bence Jones Proteins and Myeloma Light Chains and Their Implications for Antibody Complementarity, Journal of Experimental Medicine, 132: 211-250 (1970).
Wunderlich, M. et al., "AML cells are differentially sensitive to chemotherapy treatment in a human xenograft model," eBlood, vol. 121; No. 12; e90-e97 (2013).
Yamamoto, H. et al., "A mammalian homolog of the zebrafish transmembrane protein 2 (TMEM2) is the long-sought-after cell-surface hyaluronidase," J. Biol. Chem., vol. 292; No. 18; 7304-7313 (2017).
Zadnikova, P. et al., "The Degradation of Hyaluronan in the skin," Biomolecules, vol. 12; 251, 17 pages (2022).
Zagouri, F. et al., "Emerging antibodies for the treatment of multiple myeloma," Expert Opinion on Emerging Drugs, vol. 21; No. 2; 225-237 (2016).
Zojer, N. et al., "Rituximab treatment provides no clinical benefit in patients with pretreated advanced multiple myeloma," Leukemia & Lymphoma, vol. 47; No. 6; 1103-1109 (2006).
International Preliminary Report on Patentability dated Apr. 29, 2021 for International Application No. PCT/US2019/056838, entitled "Method of Providing Subcutaneous Administration of Anti-CD38 Antibodies".
International Preliminary Report on Patentability for International Application No. PCT/IB2020/051484, dated Sep. 2, 2021.

International Search Report and Written Opinion for International Application No. PCT/IB2020/051484, dated Jul. 2, 2020.
Declaration of Professor Paul Anthony Dalby, in Opposition Proceedings against European Patent No. 3370770, 20 pages (Dated May 2022).
Declaration of Professor Christian Jackisch, in Opposition Proceedings against European Patent No. 3370770, 8 pages (Dated May 10, 2022).
Declaration of Professor Adrian Llewellyn Harris, in Opposition Proceedings against European Patent No. 3370770, 109 pages (Dated Dec. 20, 2022).
Declaration of Dr. Richard Senderoff, in Opposition Proceedings against European Patent No. 3370770, 28 pages (Dated Dec. 20, 2022).
Declaration of Professor Dr. Andreas Zimmer, in Opposition Proceedings against European Patent No. 3370770, 5 pages (Dated Jan. 9, 2023).
Second Declaration of Professor Christian Jackisch, in Opposition Proceedings against European Patent No. 3370770, 8 pages (Dated Jan. 6, 2023).
Notice of Opposition Dated Oct. 20, 2021 by Opponent König Szynka Tilmann von Renesse, filed in European Patent No. 3 370 770 B1.
Notice of Opposition Dated Oct. 19, 2021 by Opponent Patent Boutique LLP, filed in European Patent No. 3 370 770 B1.
Notice of Opposition Dated Oct. 20, 2021 by Opponent Dr. Markus Breuer, filed in European Patent No. 3 370 770 B1.
Notice of Opposition Dated Dec. 22, 2022 by Opponent Dr. Hans Ulrich Dorries, filed in European Patent No. 3 827 845 B1; 44 Pages.
Notice of Opposition Dated Dec. 27, 2022 by Opponent Konig Szynka Tilmann von Renesse, filed in European Patent No. 3 827 845 B1; 49 Pages.
Notice of Opposition Dated Dec. 28, 2022 by Opponent Michalski Huttermann & Partner, filed in European Patent No. 3 827 845 B1; 44 Pages.
Notice of Opposition Dated Dec. 29, 2022 by Opponent Patent Boutique LLP, filed in European Patent No. 3 827 845 B1; 49 Pages.
Notice of Opposition Dated Dec. 21, 2022 by Opponent Xbrane Biopharma AB, filed in European Patent No. 3 827 845 B1; 68 Pages.
Opponent's submission by Dr. Markus Breuer dated Oct. 4, 2022 filed in European Patent No. 3 370 770 B1.
Opponent's submission by Konig Szynka Tilmann von Renesse dated Jan. 11, 2023, filed in European Patent No. 3 370 770 B1; 27 Pages.
Opponent's submission by Dr. Markus Breuer dated Jan. 13, 2023, filed in European Patent No. 3 370 770 B1; 11 Pages.
Opponent's submission by Patent Boutique LLP dated Jan. 12, 2023, filed in European Patent No. 3 370 770 B1; 56 Pages.
Reply to Notice of Opposition, filed in European Patent No. 3 370 770 B1, entitled: "Subcutaneous Formulations Of Anti-CD38 Antibodies And Their Uses," 416 pages, dated May 12, 2022.
Reply to Notice of Opposition, filed in European Patent No. 3 370 770 B1, entitled: "Subcutaneous Formulations Of Anti-CD38 Antibodies And Their Uses," 19 pages, dated Jan. 13, 2023.
Non Final Office Action for U.S. Appl. No. 16/840,153 dated Aug. 16, 2022.
Applicant Initiated Interview Summary for U.S. Appl. No. 16/840,153 dated Jun. 8, 2022.
Non Final Office Action for U.S. Appl. No. 16/840,153 dated Mar. 22, 2022.
Applicant Initiated Interview Summary for U.S. Appl. No. 16/840,153 dated Apr. 6, 2022.
Notice of Allowance for U.S. Appl. No. 16/840,153 dated Dec. 21, 2022.
Non Final Office Action for U.S. Appl. No. 16/927,947 dated Mar. 7, 2023.
Non Final Office Action for U.S. Appl. No. 17/116,822 dated Mar. 8, 2023.
Non Final Office Action for U.S. Appl. No. 17/116,835 dated Mar. 8, 2023.

(56) References Cited

OTHER PUBLICATIONS

Non Final Office Action for U.S. Appl. No. 16/986,214 dated Feb. 28, 2023.
Non-Final Office Action for U.S. Appl. No. 17/005,039 dated Dec. 9, 2022.
Notice of Allowance for U.S. Appl. No. 16/162,355 dated Apr. 9, 2021.
Non Final Office Action for U.S. Appl. No. 16/741,542 dated Jul. 12, 2022.
Notice of Allowance for U.S. Appl. No. 16/741,542 dated Nov. 2, 2022.
Non Final Office Action for U.S. Appl. No. 16/741,542 dated Mar. 17, 2023.
Non-Final Office Action for U.S. Appl. No. 16/312,133 dated Oct. 28, 2021.
Notice of Allowance for U.S. Appl. No. 16/312,133 dated Sep. 2, 2022.
Final Office Action for U.S. Appl. No. 16/312,133 dated May 12, 2022.
Final Office Action for U.S. Appl. No. 15/798,670 dated Aug. 10, 2021.
Non-Final Office Action for U.S. Appl. No. 15/798,670 dated Apr. 2, 2021.
Final Office Action for U.S. Appl. No. 15/798,670 dated Dec. 16, 2020.
Non-Final Office Action for U.S. Appl. No. 15/798,670 dated Feb. 4, 2022.
Non-Final Office Action for U.S. Appl. No. 16/177,239 dated Sep. 21, 2021.
Final Office Action for U.S. Appl. No. 16/177,239 dated Feb. 10, 2021.
Notice of Allowance for U.S. Appl. No. 16/177,239, dated Oct. 13, 2022.
Final Office Action for U.S. Appl. No. 16/177,239 dated Mar. 4, 2022.
Notice of Allowance for U.S. Appl. No. 16/177,239 dated Feb. 3, 2023.
Notice of Allowability for U.S. Appl. No. 16/177,239, dated Feb. 27, 2023.
Non-Final Office Action for U.S. Appl. No. 16/656,569 dated Aug. 26, 2021.
Notice of Allowance for U.S. Appl. No. 15/445,225 dated Mar. 25, 2020.
Notice of Allowance for U.S. Appl. No. 15/445,225 dated Jul. 15, 2020.
Notice of Allowance for U.S. Appl. No. 15/445,225 dated Dec. 4, 2019.
Notice of Allowance for U.S. Appl. No. 15/445,225 dated Jul. 29, 2019.
Non Final Office Action for U.S. Appl. No. 16/797,301 dated Jul. 28, 2022.
Final Office Action for U.S. Appl. No. 16/797,301 dated Feb. 17, 2023.
Non Final Office Action for U.S. Appl. No. 17/475,975 dated Mar. 10, 2023.
Non Final Office Action for U.S. Appl. No. 16/830,585 dated Mar. 17, 2022.
Final Office Action for U.S. Appl. No. 16/830,585 dated Oct. 26, 2022.
Non Final Office Action for U.S. Appl. No. 16/830,763 dated Mar. 17, 2022.
Final Office Action for U.S. Appl. No. 16/830,763 dated Oct. 24, 2022.
Non Final Office Action for U.S. Appl. No. 16/830,810 dated Mar. 15, 2022.
Final Office Action for U.S. Appl. No. 16/830,810 dated Oct. 25, 2022.
Non Final Office Action for U.S. Appl. No. 16/830,909 dated Mar. 17, 2022.
Final Office Action for U.S. Appl. No. 16/830,909 dated Oct. 26, 2022.
AstraZeneca 206162 Clinical Pharmacology Review 2014, (https://www.accessdata.fda.gov/drugsatfda_docs/nda/2014/206162Orig1s000ClinPharmR.pdf; Application No. 206162Orig1s000; 117 pages.
Child, J.A. et al., "High-Dose Chemotherapy with Hematopoietic Stem-Cell Rescue for Multiple Myeloma," N Engl J Med, vol. 348; 1875-1883 (2003).
City of Hope, "What's the Difference? Biosimilar and generic drug," City of Hope, retrieved from: https://www.cancercenter.com/community/blog/2018/12/whats-the-difference-biosimilar-and-generic-drugs; 3 Pages (Year: 2018).
Clinicaltrials.gov, "A Study to Evaluate Daratumumab in Transplant Eligible Participants with Previously Untreated Multiple Myeloma (Cassiopeia)," Identifier: NCT02541383; First Posted: Sep. 4, 2015 (29 pages).
Darzalex, Highlights and Prescribing Information, FDA Label, 11 pages (2017).
Demarest, T.G. et al., "NAD+ Metabolism in Aging and Cancer," Annual Rev. Cancer Biol., vol. 3; 105-130 (2019).
Gariani, K. et al., "Inhibiting poly ADP-ribosylation increases fatty acid oxidation and protects against fatty liver disease," Journal of Hepatology, vol. 66; 132-141 (2017).
Kaufman, J.L. et al., "Bortezomib, Thalidomide, and Dexamethasone as Induction Therapy for Patients with Symptomatic Multiple Myeloma," Cancer, vol. 116; 3143-3151 (2010).
King, T. et al., "Best Practice for the Administration of Daratumumab in Multiple Myeloma: Australian Myeloma Nurse Expert Opinion," Asia Pac J Oncol Nurs, vol. 5; 270-284 (2018).
Moreau, P. et al., "Multiple Myeloma: ESMO Clinical Practice Guidelines for dianosis, treatment and follow up," Annals of Oncology, vol. 28; Suppl 4; iv52-iv61 (2017).
Multiple Myeloma Treatment Regiments (MMTR), Multiple Myeloma Treatment Regiments (Part 1 of 9), Haymarket Media, Inc., 9 Pages (2017).
Myeloma Australia, "Steroids," Treatment Fact Sheet, Myeloma Australia, retrieved from: https://myeloma.org.au/wp-content/uploads/2018/09/Steroid-FS-Sep18.pdf 2 Pages (2018).
Decision Revoking the European Patent issued in EP Patent No. 3370770, mailed Apr. 20, 2023; 22 Pages.
Provision of the Minutes in Accordance with Rule 124(4) EPC regarding EP Patent No. 3370770, mailed Apr. 20, 2023, 14 pages.
Applicant Initiated Interview Summary for U.S. Appl. No. 16/927,947 dated Apr. 19, 2023.
Notice of Allowance for U.S. Appl. No. 16/927,947 dated Jun. 22, 2023.
Applicant Initiated Interview Summary for U.S. Appl. No. 17/116,822 dated Apr. 19, 2023.
Notice of Allowance for U.S. Appl. No. 17/116,822 dated May 12, 2023.
Applicant Initiated Interview Summary for U.S. Appl. No. 17/116,835 dated Apr. 19, 2023.
Notice of Allowance for U.S. Appl. No. 17/116,835 dated May 11, 2023.
Final Office Action for U.S. Appl. No. 17/005,039 dated Apr. 28, 2023.
Notice of Allowance for U.S. Appl. No. 16/741,542 dated Apr. 10, 2023.
Non-Final Office Action for U.S. Appl. No. 16/312,133 dated Dec. 8, 2022.
Non Final Office Action for U.S. Appl. No. 17/002,860 dated Jun. 27, 2023.
Non Final Office Action for U.S. Appl. No. 17/674,397 dated Apr. 24, 2023.
Clinicaltrials.gov, "Safety and Efficacy Study of Eculizumab in Patients with Refractory Generalized Myasthenia Gravis," Identifier: NCT00727194; Latest version: Sep. 13, 2019 (6 pages).
Davies, A. et al., "Pharmacokinetics and safety of subcutaneous rituximab in follicular lymphoma (SABRINA): stage 1 analysis of a randomised phase 3 study," The Lancet, vol. 15; 343-352 (2014); Supplemental Appendix (8 Pages).

Final Office Action for U.S. Appl. No. 16/830,909 dated Oct. 26, 2022.

(56) References Cited

OTHER PUBLICATIONS

Davis, T.A. et al., "Rituximab Anti-CD20 Monoclonal Antibody Therapy in Non-Hodgkin's Lymphoma: Safety and Efficacy of Re-Treatment," Journal of Clinical Oncology, vol. 18; No. 17; 3135-3143 (2000).

Freeley et al., "The 'Ins and Outs' of complement-driven immune responses", Immunol Rev., 274(1), pp. 16-32, Nov. 2016.

Karakasheva et al., "CD38-Expressing Myeloid-Derived Suppressor Cells Promote Tumor Growth in a Murine Model of Esophageal Cancer", Microenvironment and Immunol., 75(19), pp. 4074-4085, Oct. 1, 2015.

Kwan et al., "Complement regulation of T cell immunity", Immunol Res, 54(0), pp. 247-253, Dec. 2012.

Matsuda, M. et al., "Phenotypic analysis of plasma cells in bone marrow using flow cytometry in AL amyloidosis," Amyloid, 10(2), 110-116 (2003).

McLaughlin, P. et al., "Pituximab Chimeric Anti-CD20 Monoclonal Antibody Therapy for Relapsed Indolent Lymphoma: Half of Patients Respond to a Four-Dose Treatment Program," Journal of Clinical Oncology, vol. 16; No. 8; 2825-2833 (1998).

Piro, L.D. et al., "Extended Rituximab )anti-CD20 monoclonal antibody) therapy for relapsed or refractory low-grade or follicular non-Hodgkins lymphoma," Annals of Oncology, vol. 10; 655-661 (1999).

Rituxan (tituximab), Highlights of prescribing information. Rituxan (IV administered Rituximab; 44 pages (1997); Revised 2014.

van Beurden-Tan et al., "Systemic Literature Review and Network Meta-Analysis of Treatment Outcomes in Relapsed and/or Refractory Multiple Myeloma," Journal of Clinical Oncology, vol. 35; No. 12; 1312-1319 (2017).

Whatcott ct al., "Targeting the tumor microenvironment in cancer: why hyaluronidase deserves a second look", Cancer Discov., 1(4), pp. 291-296, Sep. 2011.

Declaration of Professor Paul Anthony Dalby, in Opposition Proceedings against European Patent No. 3827845, 20 pages (Dated Jul. 19, 2023).

Declaration of Peter Hellemans, in Opposition Proceedings against European Patent No. 3827845, 5 pages (Dated Jul. 21, 2023).

Declaration of Tara Masterson, in Opposition Proceedings against European Patent No. 3827845, 4 pages (Dated Jul. 2023).

Declaration of Professor Christian Jackisch, in Opposition Proceedings against European Patent No. 3827845, 11 pages (Dated Jul. 19, 2023).

Reply of the Patentee to the Notices of Opposition in European Patent No. 3 827 845 B1, Jul. 23, 2023 (203 pages).

Final Office Action for U.S. Appl. No. 16/986,214 dated Aug. 23, 2023.

Applicant Initiated Interview for U.S. Appl. No. 16/986,214 dated Oct. 17, 2023.

Non-Final Office Action for U.S. Appl. No. 17/005,039 dated Sep. 1, 2023.

Non Final Office Action for U.S. Appl. No. 17/691,050 dated Oct. 3, 2023.

Final Office Action for U.S. Appl. No. 17/674,397 dated Oct. 18, 2023.

Non Final Office Action for U.S. Appl. No. 16/797,301 dated Sep. 22, 2023.

BC Cancer Agency Cancer drug Manual, Oct. 1, 2013, "Hydroxyurea". http://www.bccancer.bc.ca/drug-database-site/Drug%20Index/Hydroxyurea_monograph_1Oct2013.pdf; Retrieved on Nov. 20, 2023; 7 pages (No Author given).

CHMP Assessment Report for HyQvia, 68 pages (2013).

Consolidated list of references from Opposition in patent EP No. 3827845, 6 pages; Jul. 24, 2023.

Consolidated list of references from Opposition in patent EP No. 3370770, 4 pages; 2023.

Dakhil, S. et al., "Phase III safety study of rituximab administered as a 90-minute infusion in patients with previously untreated diffuse large B-cell and follicular lymphoma," Leukemia & Lymphoma, vol. 55; No. 10; 2335-2340 (2014).

Genmab, "Genmab Announces Positive Topline Results in Phase III Cassiopeia Study of Daratumumab in Front Line Multiple Myeloma," Genmab News, 4 Pages (2018).

Leukemia—Acute Myeloid—AML—Treatment Options. Cancer. Net, Nov. 19, 2013. archived by the Wayback Machine at https://web.archive.org/web/20131120003806/http://www.cancer.net/print/19072; Retrieved on Nov. 20, 2023; 6 pages (No Author Listed).

Lokhorst, H.M., "Dose-Dependent efficacy of daratumumab (DARA) as monotherapy in patients with relapsed or refractory multiple myeloma (RR MM)," Journal of Clinical Oncology, vol. 32; No. 15; 4 pages (2014).

Morcos, P.N. et al., "Pharmacokinetics and pharmacodynamics of single subcutaneous doses of tocilizumab administered with or without rHuPH20," International Journal of Clinical Pharmacology and Therapeutics, vol. 15, No. 7/2013; 537-548 (2013).

Quartino, A.L. et al., "Population pharmacokinetic and exposure-response analysis for trastuzumab administered using a subcutaneous "manual syringe" injection or intravenously in women with HER2-positive early breast cancer," Cancer Chemother Pharmacol, vol. 77; 77-88 (2016).

Rituxan (tituximab), Highlights of prescribing information. Rituxan (IV administered Rituximab; 53 pages (1997); Revised 2021.

Wasserman, R.L. et al., "Recombinant human hyaluronidase-facilitated subcutaneous infusion of human immunoglobulins for primary immunodeficiency," J Allergy Clin Immunol, vol. 130; 951-957 (2012).

Wynne, C. et al., "Comparison of Subcutaneous and Intravenous Administration of Trastuzumab: A Phase I/Ib Trial in Healthy Male Volunteers and Patients with HER2-Positive Breast Cancer," The Journal of Clinical Pharmcology, vol. 53; No. 2; 192-201 (2012).

Annex to Form 2300—Notice of Opposition, filed on behalf of Konig Szynka Tilmann von Renesse, filed in Opposition for EP Patent 3370770, 39 pages (2024).

Second Declaration of Professor Adrian Llewellyn Harris, in Opposition Proceedings against European Patent No. 3370770, 5 pages (Dated Jan. 3, 2024).

Declaration of Peter Hellemans, in Opposition Proceedings against European Patent No. 3370770, 5 pages (Dated Aug. 24, 2023).

Declaration of Tara Masterson, in Opposition Proceedings against European Patent No. 3370770, 4 pages (Dated Aug. 2023).

Opponent's submission by Dr. Markus Bruer dated Jan. 15, 2024, filed in European Patent No. 3 370 770 B1; 53 Pages.

Opponents Submission by Dr. Markus Bruer to Comments on Proprietor's Submission , filed in EP Opposition for EP Patent 3370770, 17 pages; dated Oct. 4, 2022.

Representation for Indian Pharmaceutical Alliance in Opposition of Patent for IN Application No. 201617029321, dated May 5, 2022 (29 pages).

Reply of the Patentee, Janssen Biotech, Inc., to the Notices of Opposition in European Patent No. 3370770, Aug. 2023 (63 pages).

Response to Patentee's Statement of Grounds of Appeal, filed by Patent Boutique LLP in European Patent No. 3370770 , dated Jan. 12, 2024 (74 pages).

Response to Patentee's Statement of Grounds of Appeal, filed on behalf of Konig Szynka Tilmann von Renesse in European Patent No. 3370770 , dated Jan. 15, 2024 (106 pages).

Response to Summons to Attend Oral Proceedings in Opposition against EP 3770770, filed on behalf of Dr. Markus Bruer, 11 pages; filed on Jan. 13, 2023.

Non Final Office Action for U.S. Appl. No. 16/986,214 date mailed Dec. 26, 2023.

Final Office Action for U.S. Appl. No. 17/005,039 date mailed Dec. 22, 2023.

Non-Final Office Action for U.S. Appl. No. 17/329,057 mailed Dec. 12, 2023.

Final Office Action for U.S. Appl. No. 17/002,860 date mailed Nov. 30, 2023.

Final Office Action for U.S. Appl. No. 16/797,301 date mailed Jan. 29, 2024.

* cited by examiner

SEQUENCE LISTING

```
<160> NUMBER OF SEQ ID NOS: 20

<210> SEQ ID NO 1
<211> LENGTH: 300
<212> TYPE: PRT
<213> ORGANISM: Homo sapiens

<400> SEQUENCE: 1

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Val Leu Ala Val Val Val Pro Arg Trp Arg Gln
        35                  40                  45

Gln Trp Ser Gly Pro Gly Thr Thr Lys Arg Phe Pro Glu Thr Val Leu
    50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95
```

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125

Lys Asp Leu Ala His Gln Phe Thr Gln Val Gln Arg Asp Met Phe Thr
130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205

Asn Gly Ser Arg Ser Lys Ile Phe Asp Lys Asn Ser Thr Phe Gly Ser
    210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
        275                 280                 285

Lys Asn Pro Glu Asp Ser Ser Cys Thr Ser Glu Ile
    290                 295                 300

<210> SEQ ID NO 2
<211> LENGTH: 14
<212> TYPE: PRT
<213> ORGANISM: Homo sapiens

<400> SEQUENCE: 2

Ser Lys Arg Asn Ile Gln Phe Ser Cys Lys Asn Ile Tyr Arg
1               5                   10

<210> SEQ ID NO 3
<211> LENGTH: 14
<212> TYPE: PRT
<213> ORGANISM: Homo sapiens

<400> SEQUENCE: 3

Glu Lys Val Gln Thr Leu Glu Ala Trp Val Ile His Gly Gly
1               5                   10

<210> SEQ ID NO 4
<211> LENGTH: 122
<212> TYPE: PRT
<213> ORGANISM: Artificial Sequence
<220> FEATURE:
<223> OTHER INFORMATION: 005 mAb VH

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

-continued

Ser Ala Ile Ser Gly Ser Gly Gly Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Phe Cys
                 85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser
            115                 120

<210> SEQ ID NO 5
<211> LENGTH: 107
<212> TYPE: PRT
<213> ORGANISM: Artificial Sequence
<220> FEATURE:
<223> OTHER INFORMATION: 005 mAb VL

<400> SEQUENCE: 5

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Thr Phe Gly Gln Gly Thr Lys Val Glu Ile Lys
            100                 105

<210> SEQ ID NO 6
<211> LENGTH: 5
<212> TYPE: PRT
<213> ORGANISM: Artificial Sequence
<220> FEATURE:
<223> OTHER INFORMATION: 005 mAb HCDR1

<400> SEQUENCE: 6

Ser Phe Ala Met Ser
 1               5

<210> SEQ ID NO 7
<211> LENGTH: 17
<212> TYPE: PRT
<213> ORGANISM: Artificial Sequence
<220> FEATURE:
<223> OTHER INFORMATION: 005 mAb HCDR2

<400> SEQUENCE: 7

Ala Ile Ser Gly Ser Gly Gly Gly Thr Tyr Tyr Ala Asp Ser Val Lys
 1               5                  10                  15

Gly

<210> SEQ ID NO 8
<211> LENGTH: 13
<212> TYPE: PRT

```
<213> ORGANISM: Artificial Sequence
<220> FEATURE:
<223> OTHER INFORMATION: 005 mAb HCDR3

<400> SEQUENCE: 8

Asp Lys Ile Leu Trp Phe Gly Glu Pro Val Phe Asp Tyr
1               5                   10

<210> SEQ ID NO 9
<211> LENGTH: 11
<212> TYPE: PRT
<213> ORGANISM: Artificial Sequence
<220> FEATURE:
<223> OTHER INFORMATION: 005 mAb LCDR1

<400> SEQUENCE: 9

Arg Ala Ser Gln Ser Val Ser Ser Tyr Leu Ala
1               5                   10

<210> SEQ ID NO 10
<211> LENGTH: 7
<212> TYPE: PRT
<213> ORGANISM: Artificial Sequence
<220> FEATURE:
<223> OTHER INFORMATION: 005 mAb LCDR2

<400> SEQUENCE: 10

Asp Ala Ser Asn Arg Ala Thr
1               5

<210> SEQ ID NO 11
<211> LENGTH: 10
<212> TYPE: PRT
<213> ORGANISM: Artificial Sequence
<220> FEATURE:
<223> OTHER INFORMATION: 005 mAb LCDR3

<400> SEQUENCE: 11

Gln Gln Arg Ser Asn Trp Pro Pro Thr Phe
1               5                   10

<210> SEQ ID NO 12
<211> LENGTH: 452
<212> TYPE: PRT
<213> ORGANISM: Artificial Sequence
<220> FEATURE:
<223> OTHER INFORMATION: 005 mAb heavy chain

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110
```

```
Gly Gln Gly Thr Leu Val Thr Val Ser Ser Ala Ser Thr Lys Gly Pro
            115                 120                 125
Ser Val Phe Pro Leu Ala Pro Ser Ser Lys Ser Thr Ser Gly Gly Thr
        130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
        195                 200                 205
His Lys Pro Ser Asn Thr Lys Val Asp Lys Arg Val Glu Pro Lys Ser
    210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Glu Glu Met Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro Gly Lys
    450

<210> SEQ ID NO 13
<211> LENGTH: 214
<212> TYPE: PRT
<213> ORGANISM: Artificial Sequence
<220> FEATURE:
<223> OTHER INFORMATION: 005 mAb light chain

<400> SEQUENCE: 13

Glu Ile Val Leu Thr Gln Ser Pro Ala Thr Leu Ser Leu Ser Pro Gly
1               5                   10                  15
```

```
Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 122
<212> TYPE: PRT
<213> ORGANISM: Artificial Sequence
<220> FEATURE:
<223> OTHER INFORMATION: 003 mAb VH

<400> SEQUENCE: 14

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Phe Ser Trp Val Arg Gln Ala Pro Gly Gln Gly Leu Glu Trp Met
        35                  40                  45

Gly Arg Val Ile Pro Phe Leu Gly Ile Ala Asn Ser Ala Gln Lys Phe
    50                  55                  60

Gln Gly Arg Val Thr Ile Thr Ala Asp Lys Ser Thr Ser Thr Ala Tyr
65                  70                  75                  80

Met Asp Leu Ser Ser Leu Arg Ser Glu Asp Thr Ala Val Tyr Tyr Cys
                85                  90                  95

Ala Arg Asp Asp Ile Ala Ala Leu Gly Pro Phe Asp Tyr Trp Gly Gln
            100                 105                 110

Gly Thr Leu Val Thr Val Ser Ser Ala Ser
        115                 120

<210> SEQ ID NO 15
<211> LENGTH: 107
<212> TYPE: PRT
<213> ORGANISM: Artificial Sequence
<220> FEATURE:
```

<223> OTHER INFORMATION: 003 mAb VL

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys
            100                 105

<210> SEQ ID NO 16
<211> LENGTH: 122
<212> TYPE: PRT
<213> ORGANISM: Artificial Sequence
<220> FEATURE:
<223> OTHER INFORMATION: 024 mAb VH

<400> SEQUENCE: 16

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg Gln Met Pro Gly Lys Gly Leu Glu Trp Met
        35                  40                  45

Gly Ile Ile Tyr Pro His Asp Ser Asp Ala Arg Tyr Ser Pro Ser Phe
50                  55                  60

Gln Gly Gln Val Thr Phe Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Val Gly Trp Gly Ser Arg Tyr Trp Tyr Phe Asp Leu Trp
            100                 105                 110

Gly Arg Gly Thr Leu Val Thr Val Ser Ser
        115                 120

<210> SEQ ID NO 17
<211> LENGTH: 107
<212> TYPE: PRT
<213> ORGANISM: Artificial Sequence
<220> FEATURE:
<223> OTHER INFORMATION: 024 mAb VL

<400> SEQUENCE: 17

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly

```
                50                  55                  60
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                     85                  90                  95

Thr Phe Gly Gln Gly Thr Lys Val Glu Ile Lys
                100                 105
```

<210> SEQ ID NO 18
<211> LENGTH: 120
<212> TYPE: PRT
<213> ORGANISM: Artificial Sequence
<220> FEATURE:
<223> OTHER INFORMATION: MOR202 VH

<400> SEQUENCE: 18

```
Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Tyr Met Asn Trp Val Arg Gln Ala Pro Gly Lys Gly Leu Glu Trp Val
             35                  40                  45

Ser Gly Ile Ser Gly Asp Pro Ser Asn Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg Asp Leu Pro Leu Val Tyr Thr Gly Phe Ala Tyr Trp Gly Gln
                100                 105                 110

Gly Thr Leu Val Thr Val Ser Ser
                115                 120
```

<210> SEQ ID NO 19
<211> LENGTH: 109
<212> TYPE: PRT
<213> ORGANISM: Artificial Sequence
<220> FEATURE:
<223> OTHER INFORMATION: MOR202 VL

<400> SEQUENCE: 19

```
Asp Ile Glu Leu Thr Gln Pro Pro Ser Val Ser Val Ala Pro Gly Gln
 1               5                  10                  15

Thr Ala Arg Ile Ser Cys Ser Gly Asp Asn Leu Arg His Tyr Tyr Val
                20                  25                  30

Tyr Trp Tyr Gln Gln Lys Pro Gly Gln Ala Pro Val Leu Val Ile Tyr
             35                  40                  45

Gly Asp Ser Lys Arg Pro Ser Gly Ile Pro Glu Arg Phe Ser Gly Ser
         50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Thr Tyr Thr Gly Gly Ala Ser Leu
                     85                  90                  95

Val Phe Gly Gly Gly Thr Lys Leu Thr Val Leu Gly Gln
                100                 105
```

<210> SEQ ID NO 20
<211> LENGTH: 4

```
<212> TYPE: PRT
<213> ORGANISM: Homo sapiens

<400> SEQUENCE: 20

Val Gln Leu Thr
1
```

COMBINATION THERAPIES WITH ANTI-CD38 ANTIBODIES

CROSS-REFERENCE TO RELATED APPLICATIONS

This application is a continuation of U.S. application Ser. No. 15/445,225, filed on Feb. 28, 2017, which is a continuation of U.S. application Ser. No. 14/629,941, filed on Feb. 24, 2015, issued as U.S. Pat. No. 9,603,927, which claims the benefit of U.S. Provisional Application No. 61/946,002, filed on Feb. 28, 2014 and U.S. Provisional Application No. 62/006,386, filed on Jun. 2, 2014. The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith:
  a) File name: 01482026005_SEQUENCELISTING.txt; created on Sep. 4, 2020, 19 KB in size.

FIELD OF THE INVENTION

The present invention relates to combination therapies with anti-CD38 antibodies.

BACKGROUND OF THE INVENTION

CD38 is a multifunctional protein having function in receptor-mediated adhesion and signaling as well as mediating calcium mobilization via its ecto-enzymatic activity, catalyzing formation of cyclic ADP-ribose (cADPR) and ADPR. CD38 mediates cytokine secretion and activation and proliferation of lymphocytes (Funaro et al., J Immunolog 145:2390-6, 1990; Terhorst et al., Cell 771-80, 1981; Guse et al., Nature 398:70-3, 1999). CD38, via its NAD glycohydrolase activity, also regulates extracellular $NAD^+$ levels, which have been implicated in modulating the regulatory T-cell compartment (Adriouch et al., 14:1284-92, 2012; Chiarugi et al., Nature Reviews 12:741-52, 2012). In addition to signaling via $Ca^{2+}$, CD38 signaling occurs via cross-talk with antigen-receptor complexes on T- and B-cells or other types of receptor complexes, e.g., MHC molecules, involving CD38 in several cellular responses, but also in switching and secretion of IgG1.

CD38 is a type II transmembrane glycoprotein expressed on hemopoietic cells such as medullary thymocytes, activated T- and B-cells, resting NK cells and monocytes, lymph node germinal center lymphoblasts, plasma B cells, intrafollicular cells and dendritic cells. A portion of normal bone marrow cells, particular precursor cells as well as unbilical cord cells are CD38-positive. In addition to lymphoid precursor cells, CD38 is expressed on erythrocytes and on platelets, and expression is also found in some solid tissues such as gut, brain, prostate, bone, and pancreas. Mature resting T- and B-cells express limited to no surface CD38.

CD38 is also expressed in a variety of malignant hematological diseases, including multiple myeloma, leukemias and lymphomas, such as B-cell chronic lymphocytic leukemia, T- and B-cell acute lymphocytic leukemia, Waldenstrom macroglobulinemia, primary systemic amyloidosis, mantle-cell lymphoma, pro-lymphocytic/myelocytic leukemia, acute myeloid leukemia, chronic myeloid leukemia, follicular lymphoma, Burkitt's lymphoma, large granular lymphocytic (LGL) leukemia, NK-cell leukemia and plasma-cell leukemia. Expression of CD38 has been described on epithelial/endothelial cells of different origin, including glandular epithelium in prostate, islet cells in pancreas, ductal epithelium in glands, including parotid gland, bronchial epithelial cells, cells in testis and ovary and tumor epithelium in colorectal adenocarcinoma. Other diseases, where CD38 expression may be involved, include, e.g., broncho-epithelial carcinomas of the lung, breast cancer (evolving from malignant proliferation of epithelial lining in ducts and lobules of the breast), pancreatic tumors evolving from the β-cells (insulinomas), tumors evolving from epithelium in the gut (e.g., adenocarcinoma and squamous cell carcinoma), carcinoma in the prostate gland, and seminomas in testis and ovarian cancers. In the central nervous system, neuroblastomas express CD38.

B-cell malignancies may arise in all lymphoid tissues where B-cells are normally being produced. Most patients with B-cell malignancies are initially diagnosed with disease involving bone marrow or lymph nodes. In the case of bone marrow involvement, the transformed B cells frequently circulate through the blood and become widely disseminated throughout peripheral lymphoid tissues. However, B-cell malignancies may also arise in some nonlymphoid tissues such as the thyroid, gastrointestinal tract, salivary glands and conjunctiva.

Well known B-cell malignancies include B-cell chronic lymphocytic leukemia, mantle cell lymphoma, Burkitt lymphoma, follicular lymphoma, diffuse large B-cell lymphoma, multiple myeloma, Hodgkin's lymphoma, hairy cell leukemia, primary effusion lymphoma and AIDS-related Non-Hodgkin's Lymphoma (NHL). B-cell malignancies comprise more than 85% of diagnosed lymphomas.

NHL is a broad classification of lymphomas originating from the lymphatic system when lymphocytes (B-cells or T-cells) become malignant and proliferate uncontrollably to form a tumor mass. In total, NHL encompasses around 30 different subtypes of lymphoma with a range of phenotypes and prognoses. It is projected that the incidence of NHL will reach over 140,000 in the major market countries by 2019.

Diffuse Large B-cell Lymphoma (DLBCL) is an aggressive most common subtype of NHL, accounting for 30-40% of lymphoid malignancy, and encompasses a biologically and clinically diverse set of diseases. Gene expression profiling studies suggest that DLBCL can be separated into two groups on the basis of gene expression profiles; these groups are known as germinal center B-cell like (GCB) and activated B-cell-like (ABC) lymphomas.

The standard of care for treatment of DLBCL is commonly called CHOP, a combination of cyclophosphamide, hydroxydaunorubicin (doxorubicin), vincristine and prednisone, or R-CHOP, a combination of anti-CD20 antibody rituximab and CHOP. In addition, following remission, hematopoietic stem cell transplantation may be considered.

Despite the current treatment options, the survival rates within high risk groups of aggressive NHL can be as low as 30% over 5 years. Therefore, there is a need for effective treatments and combination treatments for NHL and B-cell malignancies.

SUMMARY OF THE INVENTION

One embodiment of the invention is a method of treating a subject having a CD38-positive hematological malignancy, comprising administering to a patient in need thereof an anti-CD38 antibody in combination with cyclophosphamide, doxorubicin, vincristine and prednisone (CHOP), wherein the anti-CD38 antibody induces killing of CD38-expressing cells in vitro by antibody-dependent cell-mediated cytotoxicity (ADCC), antibody-dependent cellular phagocytosis (ADCP), complement dependent cytotoxicity (CDC), apoptosis, or modulation of CD38 enzymatic activity.

DETAILED DESCRIPTION OF THE INVENTION

Figure 1A:
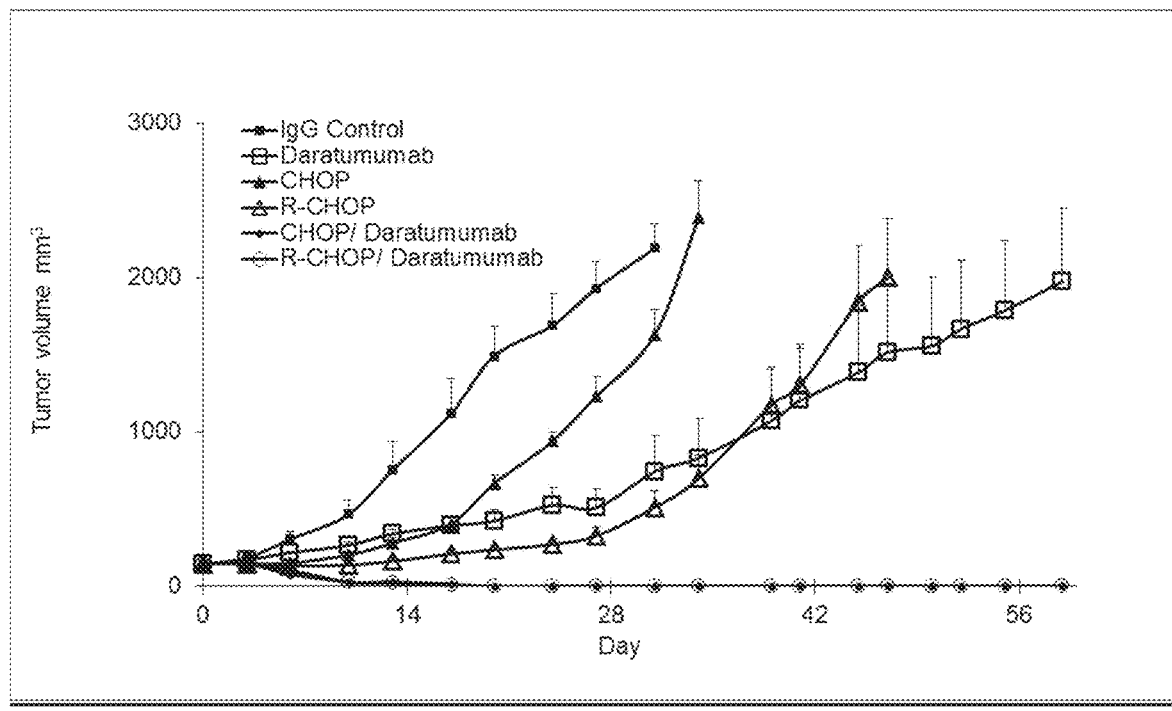
FIG. 1A shows efficacy of daratumumab in a patient-derived model of diffuse large B-cell lymphoma (DLBCL) alone or in combination of CHOP or R-CHOP. Resected DLBCL tumors were implanted in SCID/Beige mice. Treatments were initiated when the tumors reached approximately 125-250 mm$^3$. Daratumumab was administered at 20 mg/kg once a week for three weeks. CHOP and R-CHOP were administered once on day 0 except prednisone was administered on days 0-4 using the following regimens: CHOP: (cyclophosphoamide (CTX): 30 mg/kg i.v.; doxorubicin: 2.5 mg/kg i.v; vincristine: 0.4 mg/kg i.v); prednisone: 0.15 mg/kg p.o; R-CHOP: rituximab 20 mg/kg i.p. DAY 0. Tumor volume was measured every three days. The Y-axis represents tumor volume±SEM.

"CD38" refers to the human CD38 protein (synonyms: ADP-ribosyl cyclase 1, cADPr hydrolase 1, Cyclic ADP-ribose hydrolase 1). Human CD38 has an amino acid sequence shown in SEQ ID NO: 1.

The term "antibodies" as used herein is meant in a broad sense and includes immunoglobulin molecules including polyclonal antibodies, monoclonal antibodies including murine, human, human-adapted, humanized and chimeric monoclonal antibodies, antibody fragments, bispecific or multispecific antibodies, dimeric, tetrameric or multimeric antibodies, and single chain antibodies.

Immunoglobulins can be assigned to five major classes, namely IgA, IgD, IgE, IgG and IgM, depending on the heavy chain constant domain amino acid sequence. IgA and IgG are further sub-classified as the isotypes IgA$_1$, IgA$_2$, IgG$_1$, IgG$_2$, IgG$_3$ and IgG$_4$. Antibody light chains of any vertebrate species can be assigned to one of two clearly distinct types, namely kappa (κ) and lambda (λ), based on the amino acid sequences of their constant domains.

The term "antibody fragments" refers to a portion of an immunoglobulin molecule that retains the heavy chain and/or the light chain antigen binding site, such as heavy chain complementarity determining regions (HCDR) 1, 2 and 3, light chain complementarity determining regions (LCDR) 1, 2 and 3, a heavy chain variable region (VH), or a light chain variable region (VL). Antibody fragments include a Fab fragment, a monovalent fragment consisting of the VL, VH, CL and CHI domains; a F(ab)$_2$ fragment, a bivalent fragment comprising two Fab fragments linked by a disulfide bridge at the hinge region; a Fd fragment consisting of the VH and CHI domains; a Fv fragment consisting of the VL and VH domains of a single arm of an antibody; a domain antibody (dAb) fragment (Ward et al., Nature 341:544-546, 1989), which consists of a VH domain. VH and VL domains can be engineered and linked together via a synthetic linker to form various types of single chain antibody designs where the VH/VL domains pair intramolecularly, or intermolecularly in those cases when the VH and VL domains are expressed by separate single chain antibody constructs, to form a monovalent antigen binding site, such as single chain Fv (scFv) or diabody; described for example in Intl. Pat. Publ. Nos. WO1998/44001, WO1988/01649, WO1994/13804, and WO1992/01047. These antibody fragments are obtained using well known techniques known to those of skill in the art, and the fragments are screened for utility in the same manner as are full length antibodies.

The phrase "isolated antibody" refers to an antibody or antibody fragment that is substantially free of other antibodies having different antigenic specificities (e.g., an antibody that specifically binds CD38. An isolated antibody that specifically binds CD38, however, can have cross-reactivity to other antigens, such as orthologs of human CD38 such as Macaca fascicularis (cynomolgus) CD38. Moreover, an isolated antibody may be substantially free of other cellular material and/or chemicals.

An antibody variable region consists of a "framework" region interrupted by three "antigen binding sites". The antigen binding sites are defined using various terms such as Complementarity Determining Regions (CDRs), three in the VH (HCDR1, HCDR2, HCDR3), and three in the VL (LCDR1, LCDR2, LCDR3), are based on sequence variability (Wu and Kabat J Exp Med 132:211-50, 1970; Kabat et al Sequences of Proteins of Immunological Interest, 5th Ed. Public Health Service, National Institutes of Health, Bethesda, Md., 1991) or "Hypervariable regions", "HVR", or "HV", three in the VH (H1, H2, H3) and three in the VL (L1, L2, L3), refer to the regions of an antibody variable domains which are hypervariable in structure as defined by Chothia and Lesk (Chothia and Lesk Mol Biol 196:901-17, 1987). Other terms include "IMGT®-CDRs" (Lefranc et al., Dev Comparat Immunol 27:55-77, 2003) and "Specificity Determining Residue Usage" (SDRU) (Almagro, Mol Recognit 17:132-43, 2004). The International ImMunoGeneTics (IMGT®) database (www_imgt_org) provides a standardized numbering and definition of antigen-binding sites. The correspondence between CDRs, HVs and IMGT delineations is described in Lefranc et al., Dev Comparat Immunol 27:55-77, 2003.

"Chothia residues" as used herein are the antibody VL and VH residues numbered according to Al-Lazikani (Al-Lazikani et al., J Mol Biol 273:927-48, 1997).

"Framework" or "framework sequences" are the remaining sequences of a variable region other than those defined to be antigen binding sites. Because the antigen binding sites can be defined by various terms as described above, the exact amino acid sequence of a framework depends on how the antigen-binding site was defined.

"Humanized antibody" refers to an antibody in which the antigen binding sites are derived from non-human species and the variable region frameworks are derived from human immunoglobulin sequences. Humanized antibodies may include substitutions in the framework regions so that the framework may not be an exact copy of expressed human immunoglobulin or germline gene sequences.

"Human-adapted" antibodies or "human framework adapted (HFA)" antibodies refers to humanized antibodies adapted according to methods described in U.S. Pat. Publ. No. US2009/0118127. Human-adapted antibodies are humanized by selecting the acceptor human frameworks based on the maximum CDR and FR similarities, length compatibilities and sequence similarities of CDR1 and CDR2 loops and a portion of light chain CDR3 loops.

"Human antibody" refers to an antibody having heavy and light chain variable regions in which both the framework and the antigen binding sites are derived from sequences of human origin. If the antibody contains a constant region, the constant region also is derived from sequences of human origin.

A human antibody comprises heavy or light chain variable regions that are "derived from" sequences of human origin where the variable regions of the antibody are obtained from a system that uses human germline immunoglobulin or rearranged immunoglobulin genes. Such systems include human immunoglobulin gene libraries displayed on phage, and transgenic non-human animals such as mice carrying human immunoglobulin loci as described herein. A human antibody may contain amino acid differences when compared to the human germline or rearranged immunoglobulin sequences due to for example naturally occurring somatic mutations or intentional introduction of substitutions in the framework or antigen binding sites. Typically, a human antibody is at least about 80%, 81%, 82%, 83%, 84%, 85%, 86%, 87%, 88%, 89%, 90%, 91%, 92%, 93%, 94%, 95%, 96%, 97%, 98%, 99% or 100% identical in amino acid sequence to an amino acid sequence encoded by a human germline or rearranged immunoglobulin gene. In some cases, a human antibody may contain consensus framework sequences derived from human framework sequence analyses, for example as described in Knappik et al., J Mol Biol 296:57-86, 2000), or synthetic HCDR3 incorporated into human immunoglobulin gene libraries displayed on phage, for example as described in Shi et al., J Mol Biol 397:385-96, 2010 and Intl. Pat. Publ. No. WO2009/085462). Antibodies in which antigen binding sites are derived from a non-human species are not included in the definition of human antibody.

Isolated humanized antibodies may be synthetic. Human antibodies, while derived from human immunoglobulin sequences, may be generated using systems such as phage display incorporating synthetic CDRs and/or synthetic frameworks, or can be subjected to in vitro mutagenesis to improve antibody properties, resulting in antibodies that do not naturally exist within the human antibody germline repertoire in vivo.

The term "recombinant antibody" as used herein, includes all antibodies that are prepared, expressed, created or isolated by recombinant means, such as antibodies isolated from an animal (e.g., a mouse) that is transgenic or transchromosomal for human immunoglobulin genes or a hybridoma prepared therefrom (described further below), antibodies isolated from a host cell transformed to express the antibody, antibodies isolated from a recombinant combinatorial antibody library, and antibodies prepared, expressed, created or isolated by any other means that involve splicing of human immunoglobulin gene sequences to other DNA sequences, or antibodies that are generated in vitro using Fab arm exchange such as bispecific antibodies.

The term "monoclonal antibody" as used herein refers to a preparation of antibody molecules of single molecular composition. A monoclonal antibody composition displays a single binding specificity and affinity for a particular epitope, or in a case of a bispecific monoclonal antibody, a dual binding specificity to two distinct epitopes.

The term "epitope" as used herein means a portion of an antigen to which an antibody specifically binds. Epitopes usually consist of chemically active (such as polar, non-polar or hydrophobic) surface groupings of moieties such as amino acids or polysaccharide side chains and can have specific three-dimensional structural characteristics, as well as specific charge characteristics. An epitope can be composed of contiguous and/or discontiguous amino acids that form a conformational spatial unit. For a discontiguous epitope, amino acids from differing portions of the linear sequence of the antigen come in close proximity in 3-dimensional space through the folding of the protein molecule.

"Variant" as used herein refers to a polypeptide or a polynucleotide that differs from a reference polypeptide or a reference polynucleotide by one or more modifications for example, substitutions, insertions or deletions.

"Synergy", "synergism" or "synergistic" mean more than the expected additive effect of a combination.

The term "in combination with" as used herein means that two or more therapeutics can be administered to a subject together in a mixture, concurrently as single agents or sequentially as single agents in any order.

The terms "treat" or "treatment" refers to both therapeutic treatment and prophylactic or preventative measures, wherein the object is to prevent or slow down (lessen) an undesired physiological change or disorder, such as the development or spread of tumor or tumor cells. Beneficial or desired clinical results include alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if a subject was not receiving treatment. Those in need of treatment include those already with the condition or disorder as well as those prone to have the condition or disorder or those in which the condition or disorder is to be prevented.

"Inhibits growth" (e.g., referring to cells, such as tumor cells) refers to a measurable decrease in the cell growth in vitro or in vivo when contacted with a therapeutic or a combination of therapeutics or drugs when compared to the growth of the same cells grown in appropriate control conditions well known to the skilled in the art. Inhibition of growth of a cell in vitro or in vivo may be at least about 10%, 20%, 30%, 40%, 50%, 60%, 70%, 80%, 90%, 99%, or 100%. Inhibition of cell growth can occur by a variety of mechanisms, for example by antibody-dependent cell-mediated toxicity (ADCC), antibody dependent cellular phagocytosis (ADCP), complement dependent cytotoxicity (CDC), apoptosis, necrosis, or inhibition of cell proliferation.

A "therapeutically effective amount" refers to an amount effective, at dosages and for periods of time necessary, to achieve a desired therapeutic result. A therapeutically effective amount may vary according to factors such as the disease state, age, sex, and weight of the individual, and the ability of a therapeutic or a combination of therapeutics to elicit a desired response in the individual. Exemplary indicators of an effective therapeutic or combination of therapeutics that include, for example, improved well-being of the patient, reduction of a tumor burden, arrested or slowed growth of a tumor, and/or absence of metastasis of cancer cells to other locations in the body.

The invention provides methods for treating patients having CD38-positive hematological malignancy. The invention is based on the discovery that an anti-CD38 antibody administered in combination with CHOP or R-CHOP provides a synergistically potent therapeutic efficacy in vivo in relevant tumor models of hematological malignancy.

One embodiment of the invention disclosed herein, including in the numbered embodiments listed below, is a method of treating a subject having a CD38-positive hematological malignancy, comprising administering to a patient in need thereof an anti-CD38 antibody in combination with cyclophosphamide, doxorubicin, vincristine and prednisone (CHOP), wherein the anti-CD38 antibody induces killing of CD38-expressing cells in vitro by antibody-dependent cell-mediated cytotoxicity (ADCC), antibody dependent cellular phagocytosis (ADCP), complement dependent cytotoxicity (CDC), apoptosis, or modulation of CD38 enzymatic activity.

In some embodiments of the invention disclosed herein, including in the numbered embodiments listed below, the anti-CD38 antibody induces in vitro killing of the CD38-expressing cells by ADCC or CDC.

"CD38-positive hematological malignancy" refers to a hematological malignancy characterized by the presence of tumor cells expressing CD38 including leukemias, lymphomas and myeloma. Examples of such CD38-positive hematological malignancies include precursor B-cell lymphoblastic leukemia/lymphoma and B-cell non-Hodgkin's lymphoma; acute promyelocytic leukemia, acute lymphoblastic leukemia and mature B-cell neoplasms, such as B-cell chronic lymphocytic leukemia (CLL)/small lymphocytic lymphoma (SLL), B-cell acute lymphocytic leukemia, B-cell prolymphocytic leukemia, lymphoplasmacytic lymphoma, mantle cell lymphoma (MCL), follicular lymphoma (FL), including low-grade, intermediate-grade and high-grade FL, cutaneous follicle center lymphoma, marginal zone B-cell lymphoma (MALT type, nodal and splenic type), hairy cell leukemia, diffuse large B-cell lymphoma (DLBCL), Burkitt's lymphoma (BL), plasmacytoma, multiple myeloma, plasma cell leukemia, post-transplant lymphoproliferative disorder, Waldenstrom's macroglobulinemia, plasma cell leukemias and anaplastic large-cell lymphoma (ALCL).

In one embodiment of the invention disclosed herein, including in the numbered embodiments listed below, the CD-38 positive hematological malignancy is multiple myeloma.

In one embodiment of the invention disclosed herein, including in the numbered embodiments listed below, the CD-38 positive hematological malignancy is diffuse large B-cell lymphoma (DLBCL).

In one embodiment of the invention disclosed herein, including in the numbered embodiments listed below, the CD-38 positive hematological malignancy is non-Hodgkin's lymphoma.

In one embodiment of the invention disclosed herein, including in the numbered embodiments listed below, the CD-38 positive hematological malignancy is acute lymphoblastic leukemia (ALL).

In one embodiment of the invention disclosed herein, including in the numbered embodiments listed below, the CD-38 positive hematological malignancy is follicular lymphoma (FL).

In one embodiment of the invention disclosed herein, including in the numbered embodiments listed below, the CD-38 positive hematological malignancy is Burkitt's lymphoma (BL).

In one embodiment of the invention disclosed herein, including in the numbered embodiments listed below, the CD-38 positive hematological malignancy is mantle cell lymphoma (MCL).

In one embodiment of the invention disclosed herein, including in the numbered embodiments listed below, the CD38-positive hematological malignancy is multiple myeloma, acute lymphoblastic leukemia (ALL), non-Hodgkin's lymphoma, diffuse large B-cell lymphoma (DLBCL), Burkitt's lymphoma (BL), follicular lymphoma (FL) or mantle-cell lymphoma (MCL).

Examples of B-cell non-Hodgkin's lymphomas are lymphomatoid granulomatosis, primary effusion lymphoma, intravascular large B-cell lymphoma, mediastinal large B-cell lymphoma, heavy chain diseases (including γ, μ, and a disease), lymphomas induced by therapy with immunosuppressive agents, such as cyclosporine-induced lymphoma, and methotrexate-induced lymphoma.

In one embodiment of the present invention, including in the numbered embodiments listed below the disorder involving cells expressing CD38 is Hodgkin's lymphoma.

Other examples of disorders involving cells expressing CD38 include malignancies derived from T and NK cells including: mature T cell and NK cell neoplasms including T-cell prolymphocytic leukemia, T-cell large granular lymphocytic leukemia, aggressive NK cell leukemia, adult T-cell leukemia/lymphoma, extranodal NK/T cell lymphoma, nasal type, 78 enteropathy-type T-cell lymphoma, hepatosplenic T-cell lymphoma, subcutaneous panniculitis-like T-cell lymphoma, blastic NK cell lymphoma, Mycosis Fungoides/Sezary Syndrome, primary cutaneous CD30 positive T-cell lymphoproliferative disorders (primary cutaneous anaplastic large cell lymphoma C-ALCL, lymphomatoid papulosis, borderline lesions), angioimmunoblastic T-cell lymphoma, peripheral T-cell lymphoma unspecified, and anaplastic large cell lymphoma.

Examples of malignancies derived from myeloid cells include acute myeloid leukemia, including acute promyelocytic leukemia, and chronic myeloproliferative diseases, including chronic myeloid leukemia.

Any anti-CD38 antibody may be used in the methods of the invention as disclosed herein, including in the numbered embodiments listed below, provided that the anti-CD38 antibody induces in vitro killing of CD38-expressing cells by antibody-dependent cell-mediated cytotoxicity (ADCC), antibody-dependent cellular phagocytosis (ADCP), complement dependent cytotoxicity (CDC), apoptosis, or modulation of CD38 enzymatic activity. The variable regions of the anti-CD38 antibodies may be obtained from existing anti-CD38 antibodies, and cloned as full length antibodies using standard methods. Exemplary variable regions binding CD38 that may be used are described, e.g., in Intl. Pat. Publ. Nos. WO05/103083, WO06/125640, WO07/042309, WO08/047242, WO12/092612, WO06/099875 and WO11/154453A1.

An exemplary anti-CD38 antibody that may be used is daratumumab. Daratumumab comprises heavy chain variable region (VH) and a light chain variable region (VL) amino acid sequences shown in SEQ ID NO: 4 and 5, respectively, heavy chain CDRs HCDR1, HCDR2 and HCDR3 of SEQ ID NOs: 6, 7 and 8, respectively, and light chain CDRs LCDR1, LCDR2 and LCDR3 of SEQ ID NOs: 9, 10 and 11, respectively, and is of IgG1/κ subtype. Daratumumab heavy chain amino acid sequence is shown in SEQ ID NO: 12 and light chain amino acid sequence shown in SEQ ID NO: 13.

SEQ ID NO: 1
MANCEFSPVSGDKPCCRLSRRAQLCLGVSILVLILVVVLAVVVPRWRQQW
SGPGTTKRFPETVLARCVKYTEIHPEIVIRHVDCQSVWDAFKGAFISKHP
CNITEEDYQPLMKLGTQTVPCNKILLWSRIKDLAHQFTQVQRDMFTLEDT
LLGYLADDLTWCGEFNTSKINYQSCPDWRKDCSNNPVSVFWKTVSRRFAE
AACDVVHVMLNGSRSKIFDKNSTFGSVEVHNLQPEKVQTLEAWVIHGGRE
DSRDLCQDPTIKELESIISKRNIQFSCKNIYRPDKFLQCVKNPEDSSCTS
EI

SEQ ID NO: 2
SKRNIQFSCKNIYR

SEQ ID NO: 3
EKVQTLEAWVIHGG

SEQ ID NO: 4
EVQLLESGGGLVQPGGSLRLSCAVSGFTFNSFAMSWVRQAPGKGLEWVSA
ISGSGGGTYYADSVKGRFTISRDNSKNTLYLQMNSLRAEDTAVYFCAKDK
ILWFGEPVFDYWGQGTLVTVSS

SEQ ID NO: 5
EIVLTQSPATLSLSPGERATLSCRASQSVSSYLAWYQQKPGQAPRLLIYD
ASNRATGIPARFSGSGSGTDFTLTISSLEPEDFAVYYCQQRSNWPPTFGQ
GTKVEIK

SEQ ID NO: 6
SFAMS

SEQ ID NO: 7
AISGSGGGTYYADSVKG

SEQ ID NO: 8
DKILWFGEPVFDY

SEQ ID NO: 9
RASQSVSSYLA

SEQ ID NO: 10
DASNRAT

SEQ ID NO: 11
QQRSNWPPTF

SEQ ID NO: 12
EVQLLESGGGLVQPGGSLRLSCAVSGFTFNSFAMSWVRQAPGKGLEWVS
AISGSGGGTYYADSVKGRFTISRDNSKNTLYLQMNSLRAEDTAVYFCAK
DKILWFGEPVFDYWGQGTLVTVSSASTKGPSVFPLAPSSKSTSGGTAAL
GCLVKDYFPEPVTVSWNSGALTSGVHTFPAVLQSSGLYSLSSVVTVPSS
SLGTQTYICNVNHKPSNTKVDKRVEPKSCDKTHTCPPCPAPELLGGPSV
FLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQP
ENNYKTTPPVLDSDGSFFLYSKLTVDKSRWQQGNVFSCSVMHEALHNHY
TQKSLSLSPGK

SEQ ID NO: 13
EIVLTQSPATLSLSPGERATLSCRASQSVSSYLAWYQQKPGQAPRLLIY
DASNRATGIPARFSGSGSGTDFTLTISSLEPEDFAVYYCQQRSNWPPTF
GQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC

Another exemplary anti-CD38 antibody that may be used is mAb003 comprising the VH and VL sequences of SEQ ID NOs: 14 and 15, respectively and described in U.S. Pat. No. 7,829,693.

SEQ ID NO: 14
QVQLVQSGAEVKKPGSSVKVSCKASGGTFSSYAFSWVRQAPGQGLEWMGR
VIPFLGIANSAQKFQGRVTITADKSTSTAY
MDLSSLRSEDTAVYYCARDDIAALGPFDYWGQGTLVTVSSAS

SEQ ID NO: 15
DIQMTQSPSSLSASVGDRVTITCRASQGISSWLAWYQQKPEKAPKSLIYA
ASSLQSGVPSRFSGSGSGTDFTLTISSLQP
EDFATYYCQQYNSYPRTFGQGTKVEIK

Another exemplary anti-CD38 antibody that may be used is mAb024 comprising the VH and VL sequences of SEQ ID NOs: 16 and 17, respectively, described in U.S. Pat. No. 7,829,693.

SEQ ID NO: 16
EVQLVQSGAEVKKPGESLKISCKGSGYSFSNYWIGWVRQMPGKGLEWMGI

IYPHDSDARYSPSFQGQVTFSADKSISTAY

LQWSSLKASDTAMYYCARHVGWGSRYWYFDLWGRGTLVTVSS

SEQ ID NO: 17
EIVLTQSPATLSLSPGERATLSCRASQSVSSYLAWYQQKPGQAPRLLIYD

ASNRATGIPARFSGSGSGTDFTLTISSLEP

EDFAVYYCQQRSNWPPTFGQGTKVEIK

Another exemplary anti-CD38 antibody that may be used is MOR-202 (MOR-03087) comprising the VH and VL sequences of SEQ ID NOs: 18 and 19, respectively, described in U.S. Pat. No. 8,088,896.

SEQ ID NO: 18
QVQLVESGGGLVQPGGSLRLSCAASGFTFSSYYMNWVRQAPGKGLEWVSG

ISGDPSNTYYADSVKGRFTISRDNSKNTLY

LQMNSLRAEDTAVYYCARDLPLVYTGFAYWGQGTLVTVSS

SEQ ID NO: 19
DIELTQPPSVSVAPGQTARISCSGDNLRHYYVYWYQQKPGQAPVLVIYGD

SKRPSGIPERFSGSNSGNTATLTISGTQAE

DEADYYCQTYTGGASLVFGGGTKLTVLGQ

Anti-CD38 antibodies used in the methods of the invention disclosed herein, including in the numbered embodiments listed below, may also be selected de novo from, e.g., a phage display library, where the phage is engineered to express human immunoglobulins or portions thereof such as Fabs, single chain antibodies (scFv), or unpaired or paired antibody variable regions (Knappik et al., J Mol Biol 296: 57-86, 2000; Krebs et al., J Immunol Meth 254:67-84, 2001; Vaughan et al., Nature Biotechnology 14:309-314, 1996; Sheets et al., PITAS (USA) 95:6157-6162, 1998; Hoogenboom and Winter, J Mol Biol 227:381, 1991; Marks et al., J Mol Biol 222:581, 1991). CD38 binding variable domains may be isolated from e.g., phage display libraries expressing antibody heavy and light chain variable regions as fusion proteins with bacteriophage pIX coat protein as described in Shi et al., J. Mol. Biol. 397:385-96, 2010 and PCT Intl. Publ. No. WO09/085462). The antibody libraries can be screened for binding to human CD38 extracellular domain, obtained positive clones further characterized, Fabs isolated from the clone lysates, and subsequentely cloned as full length antibodies. Such phage display methods for isolating human antibodies are established in the art. See for example: U.S. Pat. Nos. 5,223,409; 5,403,484; and 5,571,698, 5,427,908, 5,580,717, 5,969,108, 6,172,197, 5,885,793; 6,521,404; 6,544,731; 6,555,313; 6,582,915; and 6,593,081.

The Fc portion of the antibody may mediate antibody effector functions such as antibody-dependent cell-mediated cytotoxicity (ADCC), antibody-dependent cellular phagocytosis (ADCP) or complement dependent cytotoxicity (CDC). Such functions may be mediated by binding of an Fc effector domain(s) to an Fc receptor on an immune cell with phagocytic or lytic activity or by binding of an Fc effector domain(s) to components of the complement system. Typically, the effect(s) mediated by the Fc-binding cells or complement components result in inhibition and/or depletion of target cells, e.g., CD38-expressing cells. Human IgG isotypes IgG1, IgG2, IgG3 and IgG4 exhibit differential capacity for effector functions. ADCC may be mediated by IgG1 and IgG3, ADCP may be mediated by IgG1, IgG2, IgG3 and IgG4, and CDC may be mediated by IgG1 and IgG3.

In the methods described herein, and in some embodiments of each and every one of the numbered embodiments listed below, the anti-CD38 antibody is of IgG1, IgG2, IgG3 or IgG4 isotype.

In the methods described herein, and in some embodiments of each and every one of the numbered embodiments listed below, the anti-CD38 antibody induces in vitro killing of CD38-expressing cells by ADCC.

In the methods described herein, and in some embodiments of each and every one of the numbered embodiments listed below, the anti-CD38 antibody induces in vitro killing of CD38-expressing cells by CDC.

In the methods described herein, and in some embodiments of each and every one of the numbered embodiments listed below, the anti-CD38 antibody induces killing of CD38-expressing cells by ADCP in vitro.

In the methods described herein, and in some embodiments of each and every one of the numbered embodiments listed below, the anti-CD38 antibody induces killing of CD38-expressing cells by apoptosis in vitro.

In the methods described herein, and in some embodiments of each and every one of the numbered embodiments listed below, the anti-CD38 antibody induces killing of CD38-expressing cells by ADCC and CDC in vitro.

While not wishing to be bound to any particular theory on mechanism of action, it is expected that the anti-CD38 antibody of the invention will induce in vivo killing of CD38-expressing cells by ADCC, CDC, ADCP, apoptosis or in vivo modulation of CD38 enzymatic activity.

"Antibody-dependent cellular cytotoxicity," or "antibody-dependent cell-mediated cytotoxicity" or "ADCC" is a mechanism for inducing cell death that depends upon the interaction of antibody-coated target cells with effector cells possessing lytic activity, such as natural killer cells, monocytes, macrophages and neutrophils via Fc gamma receptors (FcγR) expressed on effector cells. For example, NK cells express FcγRIIIa, whereas monocytes express FcγRI, FcγRII and FcvRIIIa. Death of the antibody-coated target cell, such as CD38-expressing cells, occurs as a result of effector cell activity through the secretion of membrane pore-forming proteins and proteases. To assess ADCC activity of an anti-CD38 antibody in vitro, the antibody may be added to CD38-expressing cells in combination with immune effector cells, which may be activated by the antigen antibody complexes resulting in cytolysis of the target cell. Cytolysis is generally detected by the release of label (e.g., radioactive substrates, fluorescent dyes or natural intracellular proteins) from the lysed cells. Exemplary effector cells for such assays include peripheral blood mononuclear cells (PBMC) and NK cells. Exemplary target cells include Daudi cells (ATCC® CCL-213™) or B cell leukemia or lymphoma tumor cells expressing CD38. In an exemplary assay, target cells are labeled with 20 µCi of $^{51}Cr$ for 2 hours and washed extensively. Cell concentration of the target cells can be adjusted to $1\times10^6$ cells/ml, and anti-CD38 antibodies at various concentrations are added. Assays are started by adding Daudi cells at an effector:target cell ratio of 40:1. After incubation for 3 hr at 37° C. assays are stopped by centrifugation, and $^{51}Cr$ release from lysed cells are measured in a scintillation counter. Percentage of cellular cytotoxicity may be calculated as % maximal lysis which may be induced by adding 3% perchloric acid to target cells. Anti-CD38 antibodies used in the methods of the invention may induce ADCC by about 20%, 25%, 30%, 35%, 40%, 45%, 50%, 55%, 60%, 65%, 70%, 75%, 80%, 85%, 90%, 95% or 100% of control (cell lysis induced by 3% perchloric acid).

"Antibody-dependent cellular phagocytosis" ("ADCP") refers to a mechanism of elimination of antibody-coated target cells by internalization by phagocytic cells, such as macrophages or dentricit cells. In vitro ADCP may be evaluated by using monocyte-derived macrophages as effector cells and Daudi cells (ATCC® CCL-213™) or B cell leukemia or lymphoma tumor cells expressing CD38 as target cells engineered to express GFP or other labeled molecule. Effctor:target cell ratio may be for example 4:1. Effector cells may be incubated with target cells for 4 hours with or without anti-CD38 antibody. After incubation, cells may be detached using accutase. Macrophages can be identified with anti-CD11b and anti-CD14 antibodies coupled to a fluorescent label, and percent phagocytosis can be determined based on % GFP fluorescent in the CD11$^+$CD14$^+$ macrophages using standard methods. Anti-CD38 antibodies used in the methods of the invention may induce ADCP by about 20%, 25%, 30%, 35%, 40%, 45%, 50%, 55%, 60%, 65%, 70%, 75%, 80%, 85%, 90%, 95% or 100%.

"Complement-dependent cytotoxicity", or "CDC", refers to a mechanism for inducing cell death in which an Fc effector domain of a target-bound antibody binds and activates complement component C1q which in turn activates the complement cascade leading to target cell death. Activation of complement may also result in deposition of complement components on the target cell surface that facilitate ADCC by binding complement receptors (e.g., CR3) on leukocytes. CDC of CD38-expressing cells can be measured in vitro for example by plating Daudi cells at $1 \times 10^5$ cells/well (50 µl/well) in RPMI-B (RPMI supplemented with 1% BSA), adding 50 µl anti-CD38 antibodies to the wells at final concentration between 0-100 µg/ml, incubating the reaction for 15 min at room temperature, adding 11 µl of pooled human serum to the wells, and incubation the reacton for 45 min at 37° C. Percentage (%) lysed cells may be detected as % propidium iodide stained cells in FACS assay using standard methods. Anti-CD38 antibodies used in the methods of the invention may induce CDC by about 20%, 25%, 30%, 35%, 40%, 45%, 50%, 55%, 60%, 65%, 70%, 75%, 80%, 85%, 90%, 95% or 100%

The ability of monoclonal antibodies to induce ADCC can be enhanced by engineering their oligosaccharide component. Human IgG1 or IgG3 are N-glycosylated at Asn297 with the majority of the glycans in the well known biantennary G0, G0F, G1, G1F, G2 or G2F forms. Antibodies produced by non-engineered CHO cells typically have a glycan fucose content of about at least 85%. The removal of the core fucose from the biantennary complex-type oligosaccharides attached to the Fc regions enhances the ADCC of antibodies via improved FcγRIIIa binding without altering antigen binding or CDC activity. Such antibodies can be achieved using different methods reported to lead to the expression of relatively high defucosylated antibodies bearing the biantennary complex-type of Fc oligosaccharides such as control of culture osmolality (Konno et al., Cytotechnology 64:249-65, 2012), application of a variant CHO line Lec13 as the host cell line (Shields et al., J Biol Chem 277:26733-40, 2002), application of a variant CHO line EB66 as the host cell line (Olivier et al., MAbs; 2(4), 2010; Epub ahead of print; PMID:20562582), application of a rat hybridoma cell line YB2/0 as the host cell line (Shinkawa et al., J Biol Chem 278:3466-3473, 2003), introduction of small interfering RNA specifically against the α 1,6-fucosyltrasferase (FUT8) gene (Mori et al., Biotechnol Bioeng88:901-908, 2004), or co-expression of β-1,4-N-acetylglucosaminyltransferase III and Golgi α-mannosidase II or a potent alpha-mannosidase I inhibitor, kifunensine (Ferrara et al., J Biol Chem281:5032-5036, 2006, Ferrara et al., Biotechnol Bioeng 93:851-861, 2006; Xhou et al., Biotechnol Bioeng 99:652-65, 2008). ADCC elicited by anti-CD38 antibodies used in the methods of the invention, and in some embodiments of each and every one of the numbered embodiments listed below, may also be enhanced by certain substitutions in the antibody Fc. Exemplary substitutions are, for example, substitutions at amino acid positions 256, 290, 298, 312, 356, 330, 333, 334, 360, 378 or 430 (residue numbering according to the EU index) as described in U.S. Pat. No. 6,737,056.

In some methods described herein, and in some embodiments of each and every one of the numbered embodiments listed below, the anti-CD38 antibodies comprise a substitution in the antibody Fc.

In some methods described herein, and in some embodiments of each and every one of the numbered embodiments listed below, the anti-CD38 antibodies comprise a substitution in the antibody Fc at amino acid positions 256, 290, 298, 312, 356, 330, 333, 334, 360, 378 or 430 (residue numbering according to the EU index).

Another embodiment of the invention, including in the numbered embodiments listed below, is a method of treating a subject having a CD38-positive hematological malignancy, comprising administering to a patient in need thereof an anti-CD38 antibody in combination with cyclophosphamide, doxorubicin, vincristine and prednisone (CHOP), wherein the anti-CD38 antibody induces in vitro killing of CD38-expressing cells by antibody-dependent cell-mediated cytotoxicity (ADCC), antibody-dependent cellular phagocytosis (ADCP), complement dependent cytotoxicity (CDC), apoptosis, or in vitro modulation of CD38 enzymatic activity, wherein the anti-CD38 antibody competes for binding to CD38 with an antibody comprising a heavy chain variable region (VH) of SEQ ID NO: 4 and a light chain variable region (VL) of SEQ ID NO: 5 (daratumumab).

Antibodies can be evaluated for their competition with daratumumab having VH of SEQ ID NO: 4 and VL of SEQ ID NO: 5 for binding to CD38 using well known in vitro methods. In an exemplary method, CHO cells recombinantly expressing CD38 may be incubated with unlabeled daratumumab for 15 min at 4° C., followed by incubation with an excess of fluorescently labeled test antibody for 45 min at 4° C. After washing in PBS/BSA, fluorescence may be measured by flow cytometry using standard methods. In another exemplary method, extracellular portion of human CD38 may be coated on the surface of an ELISA plate. Excess of unlabelled daratumumab may be added for about 15 minutes and subsequently biotinylated test antibodies may be added. After washes in PBS/Tween, binding of the test biotinylated antibodies may be detected using horseradish peroxidase (HRP)-conjugated streptavidine and the signal detected using standard methods. It is readily apparent that in the competition assays, daratumumab may be labelled and the test antibody unlabeled. The test antibody competes with daratumumab when daratumumab inhibits binding of the test antibody, or the test antibody inhibits binding of daratumumab by 20%, 30%, 40%, 50%, 60%, 70%, 80%, 85%, 90%, 95% or 100%. The epitope of the test antibody can further be defined, for example, by peptide mapping or hydrogen/deuterium protection assays using known methods.

Another embodiment of the invention disclosed herein, including in the numbered embodiments listed below, is a method of treating a subject having a CD38-positive hematological malignancy, comprising administering to a patient in need thereof an anti-CD38 antibody that binds to the region SKRNIQFSCKNIYR (SEQ ID NO: 2) and the region EKVQTLEAWVIHGG (SEQ ID NO: 3) of human CD38 (SEQ ID NO: 1) in combination with cyclophosphamide, doxorubicin, vincristine and prednisone (CHOP), wherein the anti-CD38 antibody induces in vitro killing of CD38-expressing cells by antibody-dependent cell-mediated cytotoxicity (ADCC), antibody-dependent cellular phagocytosis (ADCP), complement dependent cytotoxicity (CDC), apoptosis, or in vitro modulation of CD38 enzymatic activity. The epitope of the antibody includes some or all of the residues in these regions having the sequences shown in SEQ ID NO: 2 or SEQ ID NO: 3. In some embodiments disclosed herein, including in the numbered embodiments listed below, the antibody epitope comprises at least one amino acid in the region SKRNIQFSCKNIYR (SEQ ID NO: 2) and at least one amino acid in the region EKVQTLEAWVIHGG (SEQ ID NO: 3) of human CD38 (SEQ ID NO: 1). In some embodiments disclosed herein, including in the numbered embodiments listed below, the antibody epitope comprises at least two amino acids in the region SKRNIQFSCKNIYR (SEQ ID NO: 2) and at least two amino acids in the region EKVQTLEAWVIHGG (SEQ ID NO: 3) of human CD38 (SEQ ID NO: 1). In some embodiments disclosed herein, including in the numbered embodiments listed below, the antibody epitope comprises at least three amino acids in the region SKRNIQFSCKNIYR (SEQ ID NO: 2) and at least three amino acids in the region EKVQTLEAWVIHGG (SEQ ID NO: 3) of human CD38 (SEQ ID NO: 1). In some embodiments disclosed herein, including in the numbered embodiments listed below, the anti-CD38 antibody binds to an epitope comprising at least KRN in the region SKRNIQFSCKNIYR (SEQ ID NO: 2) and comprising at least VQLT (SEQ ID NO: 20) in the region EKVQTLEAWVIHGG (SEQ ID NO: 3) of human CD38 (SEQ ID NO: 1).

In some embodiments of the invention described herein, and in some embodiments of each and every one of the numbered embodiments listed below, the anti-CD38 antibody binds to an epitope comprising at least KRN in the region SKRNIQFSCKNIYR (SEQ ID NO: 2) and comprising at least VQLT (SEQ ID NO: 20) in the region EKVQTLEAWVIHGG (SEQ ID NO: 3) of human CD38 (SEQ ID NO: 1).

An exemplary antibody that binds to the region SKRNIQFSCKNIYR (SEQ ID NO: 2) and the region EKVQTLEAWVIHGG (SEQ ID NO: 3) of human CD38 (SEQ ID NO: 1) or minimally to residues KRN and VQLT (SEQ ID NO: 20) as shown above is daratumumab having certain VH, VL and CDR sequences as described above. Antibodies that bind to the region SKRNIQFSCKNIYR (SEQ ID NO: 2) and the region EKVQTLEAWVIHGG (SEQ ID NO: 3) of human CD38 (SEQ ID NO: 1) can be generated, for example, by immunizing mice with peptides having the amino acid sequences shown in SEQ ID NOs: 2 and 3 using standard methods and as described herein. Antibodies can be further evaluated, for example, by assaying competition between daratumumab and a test antibody for binding to CD38 as described above.

In the methods described herein, and in some embodiments of each and every one of the numbered embodiments listed below, the anti-CD38 antibody can bind human CD38 with a range of affinities ($K_D$). In one embodiment according to the invention, and in some embodiments of each and every one of the numbered embodiments listed below, the anti-CD38 antibody binds to CD38 with high affinity, for example, with a $K_D$ equal to or less than about $10^{-}$M, such as but not limited to, 1-9.9 (or any range or value therein, such as 1, 2, 3, 4, 5, 6, 7, 8, or 9)$\times 10^{-8}$, $10^{-9}$, $10^{-10}$, $10^{-11}$, $10^{-12}$, $10^{-13}$, $10^{14}$, $10^{-15}$ or any range or value therein, as determined by surface plasmon resonance or the KINEXA® method, as practiced by those of skill in the art. One exemplary affinity is equal to or less than $1\times 10^{-8}$ M. Another exemplary affinity is equal to or less than $1\times 10^{-9}$ M.

In some methods described herein, and in some embodiments of each and every one of the numbered embodiments listed below, the anti-CD38 antibody has a a biantennary glycan structure with fucose content of about between 0% to about 15%, for example 15%, 14%, 13%, 12%, 11% 10%, 9%, 8%, 7%, 6%, 5%, 4%, 3%, 2%, 1% or 0%.

In some methods described herein, and in some embodiments of each and every one of the numbered embodiments listed below, the anti-CD38 antibody has a a biantennary glycan structure with fucose content of about 50%, 40%, 45%, 40%, 35%, 30%, 25%, 20%, 15%, 14%, 13%, 12%, 11% 10%, 9%, 8%, 7%, 6%, 5%, 4%, 3%, 2%, 1% or 0%

Substitutions in the Fc and reduced fucose content may enhance the ADCC activity of the anti-CD38 antibody.

"Fucose content" means the amount of the fucose monosaccharide within the sugar chain at Asn297. The relative amount of fucose is the percentage of fucose-containing structures related to all glycostructures. These may be characterized and quantified by multiple methods, for example: 1) using MALDI-TOF of N-glycosidase F treated sample (e.g. complex, hybrid and oligo- and high-mannose structures) as described in Int Pat. Publ. No. WO2008/077546; 2) by enzymatic release of the Asn297 glycans with subsequent derivatization and detection/quantitation by HPLC (UPLC) with fluorescence detection and/or HPLC-MS (UPLC-MS); 3) intact protein analysis of the native or reduced mAb, with or without treatment of the Asn297 glycans with Endo S or other enzyme that cleaves between the first and the second GlcNAc monosaccharides, leaving the fucose attached to the first GlcNAc; 4) digestion of the mAb to constituent peptides by enzymatic digestion (e.g., trypsin or endopeptidase Lys-C), and subsequent separation, detection and quantitation by HPLC-MS (UPLC-MS); or 5) separation of the mAb oligosaccharides from the mAb protein by specific enzymatic deglycosylation with PNGase F at Asn 297. The oligosaccharides released may be labeled with a fluorophore, separated and identified by various complementary techniques which allow fine characterization of the glycan structures by matrix-assisted laser desorption ionization (MALDI) mass spectrometry by comparison of the experimental masses with the theoretical masses, determination of the degree of sialylation by ion exchange HPLC (GlycoSep C), separation and quantification of the oligosacharride forms according to hydrophilicity criteria by normal-phase HPLC (GlycoSep N), and separation and quantification of the oligosaccharides by high performance capillary electrophoresis-laser induced fluorescence (HPCE-LIF).

"Low fucose" or "low fucose content" as used in the application refers to antibodies with fucose content of about 0%-15%.

"Normal fucose" or 'normal fucose content" as used herein refers to antibodies with fucose content of about over 50%, typically about over 60%, 70%, 80% or over 85%.

The anti-CD38 antibodies used in the methods, and in some embodiments of each and every one of the numbered embodiments listed below, may induce CD38-positive cell killing in vitro by apoptosis. Methods for evaluating apoptosis are well known, and include for example annexin IV staining using standard methods. The anti-CD38 antibodies used in the methods of the invention may induce apoptosis in about 20%, 25%, 30%, 35%, 40%, 45%, 50%, 55%, 60%, 65%, 70%, 75%, 80%, 85%, 90%, 95% or 100% of cells.

The anti-CD38 antibodies used in the methods, and in some embodiments of each and every one of the numbered embodiments listed below, may induce CD38-positive cell killing by modulation of CD38 enzymatic activity. CD38 is a multifunctional ectoenzme with ADP-ribosyl cyclase 1 activity catalyzing the formation of cyclic ADP-ribose (cADPR) and ADPR from $NAD^+$, and also functions to hydrolyze $NAD^+$ and cADPR to ADPR. CD38 also catalyzes the exchange of the nicotinamide group of $NADP^+$ with nicotinic acid under acidic conditions, to yield $NAADP^+$ (nicotinic acid-adenine dinucleotide phosphate). Modulation of the enzymatic activity of human CD38 with anti-CD38 antibodies used in the methods of the invention may be measured in an assay described in Graeff et al., J. Biol. Chem. 269, 30260-30267 (1994). For example, substrate $NGD^+$ may be incubated with CD38, and the modulation of the production of cyclic GDP-ribose (cGDPR) may be monitored spectrophotometrically at excitation at 340 nM and emission at 410 nM at different time points after addition of the antibody at various concentrations. Inhibition of the synthesis of cADPR may be determined according to the HPLC method described in Munshi et al., J. Biol. Chem. 275, 21566-21571 (2000). The anti-CD38 antibodies used in the methods of the invention may inhibit CD38 enzymatic activity by at least about 20%, 25%, 30%, 35%, 40%, 45%, 50%, 55%, 60%, 65%, 70%, 75%, 80%, 85%, 90%, 95% or 100%.

In some methods of the invention described herein, and in some embodiments of each and every one of the numbered embodiments listed below, the the anti-CD38 antibody comprises the heavy chain complementarity determining regions (HCDR) 1 (HCDR1), 2 (HCDR2) and 3 (HCDR3) sequences of SEQ ID NOs: 6, 7 and 8, respectively.

In some methods of the invention described herein, and in some embodiments of each and every one of the numbered embodiments listed below, the anti-CD38 antibody comprises the light chain complementarity determining regions (LCDR) 1 (LCDR1), 2 (LCDR2) and 3 (LCDR3) sequences of SEQ ID NOs: 9, 10 and 11, respectively.

In some methods of the invention described herein, and in some embodiments of each and every one of the numbered embodiments listed below, the anti-CD38 antibody comprises the heavy chain variable region (VH) of SEQ ID NO: 4 and the light chain variable region (VL) of SEQ ID NO: 5.

In some methods of the invention described herein, and in some embodiments of each and every one of the numbered embodiments listed below, the anti-CD38 antibody comprises a heavy chain of SEQ ID NO: 12 and a light chain of SEQ ID NO: 13.

In some methods of the invention described herein, and in some embodiments of each and every one of the numbered embodiments listed below, the anti-CD38 antibody comprises a heavy chain comprising an amino acid sequence that is 95%, 96%, 97%, 98% or 99% identical to that of SEQ ID NO: 12 and a light chain comprising an amino acid sequence that is 95%, 96%, 97%, 98% or 99% identical to that of SEQ ID NO: 13.

Antibodies that are substantially identical to the antibody comprising the heavy chain of SEQ ID NO: 12 and the light chain of SEQ ID NO: 13 may be used in the methods of the invention, and in some embodiments of each and every one of the numbered embodiments listed below. The term "substantially identical" as used herein means that the two antibody heavy chain or light chain amino acid sequences being compared are identical or have "insubstantial differences." Insubstantial differences are substitutions of 1, 2, 3, 4, 5, 6, 7, 8, 9, 10, 11, 12, 13, 14, or 15 amino acids in an antibody heavy chain or light chain that do not adversely affect antibody properties. Percent identity can be determined for example by pairwise alignment using the default settings of the AlignX module of Vector NTI v.9.0.0 (Invitrogen, Carlsbad, Calif.). The protein sequences of the present invention can be used as a query sequence to perform a search against public or patent databases to, for example, identify related sequences. Exemplary programs used to perform such searches are the XBLAST or BLASTP programs (www_ncbi_nlm/nih_gov), or the GENOMEQUEST® (GenomeQuest, Westborough, Mass.) suite using the default settings. Exemplary substitutions that can be made to the anti-CD38 antibodies used in the methods of the invention are for example conservative substitutions with an amino acid having similar charge, hydrophobic, or stereochemical characteristics. Conservative substitutions may also be made to improve antibody properties, for example stability or affinity, or to improve antibody effector functions. 1, 2, 3, 4, 5, 6, 7, 8, 9, 10, 11, 12, 13, 14, or 15 amino acid substitutions may be made for example to the heavy or the light chain of the anti-CD38 antibody. Furthermore, any native residue in the heavy or light chain may also be substituted with alanine, as has been previously described for alanine scanning mutagenesis (MacLennan et al., Acta Physiol Scand Suppl 643:55-67, 1998; Sasaki et al., Adv Biophys 35:1-24, 1998). Desired amino acid substitutions may be determined by those skilled in the art at the time such substitutions are desired. Amino acid substitutions may be done for example by PCR mutagenesis (U.S. Pat. No. 4,683,195). Libraries of variants may be generated using well known methods, for example using random (NNK) or non-random codons, for example DVK codons, which encode 11 amino acids (Ala, Cys, Asp, Glu, Gly, Lys, Asn, Arg, Ser, Tyr, Trp) and screening the libraries for variants with desired properties. The generated variants may be tested for their binding to CD38, their ability to induce ADCC, ADCP or apoptosis in vitro using methods described herein.

In some embodiments, and in some embodiments of each and every one of the numbered embodiments listed below, the anti-CD38 antibody is a bispecific antibody. The VL and/or the VH regions of the existing anti-CD38 antibodies or the VL and VH regions identified de novo as described above may be engineered into bispecific full length antibodies. Such bispecific antibodies may be made by modulating the CH3 interactions between the two monospecific antibody heavy chains to form bispecific antibodies using technologies such as those described in U.S. Pat. No. 7,695,936; Int. Pat. Publ. No. WO04/111233; U.S. Pat. Publ. No. U52010/0015133; U.S. Pat. Publ. No. US2007/0287170; Int. Pat. Publ. No. WO2008/119353; U.S. Pat. Publ. No. US2009/0182127; U.S. Pat. Publ. No. U52010/0286374; U.S. Pat. Publ. No. US2011/0123532; Int. Pat. Publ. No. WO2011/131746; Int. Pat. Publ. No. WO2011/143545; or U.S. Pat. Publ. No. US2012/0149876. Additional bispecific structures into which the VL and/or the VH regions of the antibodies of the invention can be incorporated are for example Dual Variable Domain Immunoglobulins (Int. Pat. Publ. No. WO2009/134776), or structures that include various dimerization domains to connect the two antibody arms with different specificity, such as leucine zipper or collagen dimerization domains (Int. Pat. Publ. No. WO2012/022811, U.S. Pat. Nos. 5,932,448; 6,833,441).

Another embodiment of the invention is a method of treating a subject having a CD38-positive hematological malignancy, comprising administering to a patient in need thereof an anti-CD38 antibody in combination with cyclophosphamide, doxorubicin, vincristine and prednisone (CHOP), wherein the anti-CD38 antibody induces in vitro antibody-dependent cell-mediated cytotoxicity (ADCC), antibody-dependent cellular phagocytosis (ADCP), complement dependent cytotoxicity (CDC), apoptosis, or in vitro modulation of CD38 enzymatic activity, wherein the CD38-positive hematological malignancy is multiple myeloma, acute lymphoblastic leukemia (ALL), non-Hodgkin's lymphoma, diffuse large B-cell lymphoma (DLBCL), Burkitt's lymphoma (BL), follicular lymphoma (FL) or mantle-cell lymphoma (MCL).

A therapeutic regimen of the anti-CD38 antibody in combination with cyclophosphamide, doxorubicin, vincristine and prednisone (CHOP) can provide a synergistic efficacy in in vivo tumor killing when compared to the standard of care CHOP or R-CHOP, and therefore can provide a benefit in a patient population when compared to CHOP or R-CHOP used alone.

The invention also provides for a method of treating a subject having a CD38-positive hematological malignancy, comprising administering to a patient in need thereof an anti-CD38 antibody in combination with cyclophosphamide, doxorubicin, vincristine and prednisone (CHOP), wherein the anti-CD38 antibody induces in vitro killing of CD38-expressing cells by antibody-dependent cell-mediated cytotoxicity (ADCC), antibody-dependent cellular phagocytosis (ADCP), complement dependent cytotoxicity (CDC), apoptosis, or in vitro modulation of CD38 enzymatic activity, wherein the subject is resistant to or has acquired resistance to treatment with at least one chemotherapeutic agent or a combination of at least one chemotherapeutic agent and an anti-CD20 antibody.

The invention also provides for a method of treating a subject having a CD38-positive hematological malignancy, comprising administering to a patient in need thereof an anti-CD38 antibody in combination with cyclophosphamide, doxorubicin, vincristine and prednisone (CHOP), wherein the anti-CD38 antibody induces in vitro killing of CD38-expressing cells by antibody-dependent cell-mediated cytotoxicity (ADCC), antibody-dependent cellular phagocytosis (ADCP), complement dependent cytotoxicity (CDC), apoptosis, or in vitro modulation of CD38 enzymatic activity, wherein the subject has discontinued treatment with at least one chemotherapeutic agent or a combination of at least one chemotherapeutic agent and an anti-CD20 antibody due to side-effects.

In some embodiments of the invention described herein, and in some embodiments of each and every one of the numbered embodiments listed below, the subject is resistant to or has acquired resistance to treatment with at least one chemotherapeutic agent, wherein the at least one chemotherapeutic agent is cyclophosphamide, doxorubicin, vincristine, prednisone, ifosfamide, carboplatin or etoposide.

In some embodiments of the invention described herein, and in some embodiments of each and every one of the numbered embodiments listed below, the subject is resistant to or has acquired resistance to treatment with at least one chemotherapeutic agent, wherein the at least one chemotherapeutic agent is a combination of cyclophosphamide, doxorubicin, vincristine and prednisone (CHOP).

In some embodiments of the invention described herein, and in some embodiments of each and every one of the numbered embodiments listed below, the subject is resistant to or has acquired resistance to treatment with at least one chemotherapeutic agent, wherein the at least one chemotherapeutic agent is a combination of ifosfamide, carboplatin and etoposide (ICE).

In some embodiments of the invention described herein, and in some embodiments of each and every one of the numbered embodiments listed below, the subject is resistant to or has acquired resistance to treatment with a combination of at least one chemotherapeutic agent and an anti-CD20 antibody, wherein the anti-CD 20 antibody is rituximab (RITUXAN®), ofatumumab (ARZERRA®), veltuzumab, ocrelizumab, obinutuzumab (GA-101), PRO13192 or ocratuzumab (AME-133v).

In some embodiments of the invention described herein, and in some embodiments of each and every one of the numbered embodiments listed below, the subject is resistant to or has acquired resistance to treatment with a combination of at least one chemotherapeutic agent and an anti-CD20 antibody, wherein the anti-CD 20 antibody is rituximab.

In some embodiments of the invention described herein, and in some embodiments of each and every one of the numbered embodiments listed below, the subject is resistant to or has acquired resistance to treatment with a combination of at least one chemotherapeutic agent and an anti-CD20 antibody, wherein the at least one chemotherapeutic agent is a combination of cyclophosphamide, doxorubicin, vincristine and prednisone (CHOP), and the anti-CD 20 antibody is rituximab (RITUXAN®), ofatumumab (ARZERRA®), veltuzumab, ocrelizumab, obinutuzumab (GA-101), PRO13192 or ocratuzumab (AME-133v).

In some embodiments of the invention described herein, and in some embodiments of each and every one of the numbered embodiments listed below, the subject is resistant to or has acquired resistance to treatment with a combination of at least one chemotherapeutic agent and an anti-CD20 antibody, wherein the at least one chemotherapeutic agent is a combination of ifosfamide, carboplatin and etoposide (ICE), and the anti-CD 20 antibody is rituximab (RITUXAN®), ofatumumab (ARZERRA®), veltuzumab, ocrelizumab, obinutuzumab (GA-101), PRO13192 or ocratuzumab (AME-133v).

In some embodiments of the invention described herein, and in some embodiments of each and every one of the numbered embodiments listed below, the subject is resistant to or has acquired resistance to treatment with a combination of at least one chemotherapeutic agent and an anti-CD20 antibody, wherein the at least one chemotherapeutic agent is a combination of cyclophosphamide, doxorubicin, vincristine and prednisone (CHOP) and the anti-CD20 antibody is rituximab.

In some embodiments of the invention described herein, and in some embodiments of each and every one of the numbered embodiments listed below, the subject is resistant to or has acquired resistance to treatment with a combination of at least one chemotherapeutic agent and an anti-CD20 antibody, wherein the at least one chemotherapeutic agent is a combination of ifosfamide, carboplatin and etoposide (ICE), and the anti-CD20 antibody is rituximab.

Various qualitative and/or quantitative methods may be used to determine if a subject is resistant, has developed or is susceptible to developing a resistance to treatment with at least one chemotherapeutic agent or a combination of at least one chemotherapeutic agent and an anti-CD20 antibody. Symptoms that may be associated with resistance include, for example, a decline or plateau of the well-being of the patient, an increase in the size of a tumor, increase in the numbe of cancer cells, arrested or slowed decline in growth of a tumor or tumor cells, and/or the spread of cancerous cells in the body from one location to other organs, tissues or cells. Re-establishment or worsening of various symptoms associated with tumor may also be an indication that a subject has developed or is susceptible to developing resistance to at least one chemotherapeutic agent and an anti-CD20 antibody. The symptoms associated with cancer may vary according to the type of cancer. For example, symptoms associated with B-cell malignanices may include swollen lymp nodes in neck, groin or armpits, fever, night sweats, coughing, chest pain, unexplained weight loss, abdominal swelling or pain, or a feeling of fullness. Remission in malignant lymphomas is standardized using the Cheson criteria (Cheson et al., J Clin Oncology 25:579-586, 2007), which guidelines can be used to determine if a subject has developed a resistance to at least one chemotherapeutic agent or a combination of at least one chemotherapeutic agent and an anti-CD20 antibody.

The heavy and light chain amino acid sequences of the antibodies identified by their United States Adopted Names (USAN) are typically available via the American Medical Association at www_ama-assn_org or via the CAS registry, or at International Nonproprietary Names (INN) at _www_drugs_com/inn_html.

In some embodiments of the invention described herein, and in some embodiments of each and every one of the numbered embodiments listed below, the subject having a CD38-positive hematological malignancy is homozygous for phenylalanine at position 158 of CD16 (FcγRIIIa-158F/F genotype) or heterozygous for valine and pheynylalanine at position 158 of CD16 (FcγRIIIa-158F/V genotype). CD16 is also known as the Fc gamma receptor Ma (FcγRIIIa) or the low affinity immunoglobulin gamma Fc region receptor III-A isoform. Valine/phenylalanine (V/F) polymorphism at FcγRIIIa protein residue position 158 has been shown to affect FcγRIIIa affinity to human IgG. Receptor with FcγRIIIa-158F/F or FcγRIIIa-158F/V polymorphisms demonstrates reduced Fc engagement and therefore reduced ADCC when compared to the FcγRIIIa-158V/V. The lack of or low amount of fucose on human N-linked oligosaccharides improves the ability of the antibodies to induce ADCC due to improved binding of the antibodies to human FcγRIIIa (CD16) (Shields et al., J Biol Chem 277:26733-40, 2002). Patients can be analyzed for their FcγRIIIa polymorphism using routine methods.

The invention also provides for the method of treating a subject having a CD38-positive hematological malignancy, comprising administering to a patient in need thereof an anti-CD38 antibody in combination with cyclophosphamide, doxorubicin, vincristine and prednisone (CHOP), wherein the anti-CD38 antibody induces in vitro killing of CD38-expressing cells by antibody-dependent cell-mediated cytotoxicity (ADCC), antibody-dependent cellular phagocytosis (ADCP), complement dependent cytotoxicity (CDC), apoptosis, or in vitro modulation of CD38 enzymatic activity, wherein the subject is homozygous for phenylalanine at position 158 of CD16 or heterozygous for valine and pheynylalanine at position 158 of CD16.

Administration/Pharmaceutical Compositions

In the methods of the invention, and in some embodiments of each and every one of the numbered embodiments listed below, the anti-CD38 antibodies may be provided in suitable pharmaceutical compositions comprising the anti-CD38 antibody and a pharmaceutically acceptable carrier. The carrier may be diluent, adjuvant, excipient, or vehicle with which the anti-CD38 antibody is administered. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine may be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the molecules or antibodies of the invention in such pharmaceutical formulation may vary widely, i.e., from less than about 0.5%, usually to at least about 1% to as much as 15 or 20% by weight and will be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, $21^{st}$ Edition, Troy, D. B. ed., Lipincott Williams and Wilkins, Philadelphia, Pa. 2006, Part 5, Pharmaceutical Manufacturing pp 691-1092, see especially pp. 958-989.

The mode of administration of the anti-CD38 antibody in the methods of the invention may be any suitable route such as parenteral administration, e.g., intradermal, intramuscular, intraperitoneal, intravenous or subcutaneous, pulmonary, transmucosal (oral, intranasal, intravaginal, rectal) or other means appreciated by the skilled artisan, as well known in the art.

The anti-CD38 antibody in the methods of the invention, and in some embodiments of each and every one of the numbered embodiments listed below, may be administered to a patient by any suitable route, for example parentally by intravenous (i.v.) infusion or bolus injection, intramuscularly or subcutaneously or intraperitoneally. i.v. infusion may be given over for, example, 15, 30, 60, 90, 120, 180, or 240 minutes, or from 1, 2, 3, 4, 5, 6, 7, 8, 9, 10, 11 or 12 hours.

The dose given to a patient having a CD38-positive hematological malignancy is sufficient to alleviate or at least partially arrest the disease being treated ("therapeutically effective amount") and may be sometimes 0.005 mg/kg to about 100 mg/kg, e.g. about 0.05 mg/kg to about 30 mg/kg or about 5 mg to about 25 mg/kg, or about 4 mg/kg, about 8 mg/kg, about 16 mg/kg or about 24 mg/kg, or, e.g., about 1, 2, 3, 4, 5, 6, 7, 8, 9 or 10 mg/kg, but may even higher, for example about 15, 16, 17, 18, 19, 20, 21, 22, 23, 24, 25, 30, 40, 50, 60, 70, 80, 90 or 100 mg/kg.

A fixed unit dose may also be given, for example, 50, 100, 200, 500 or 1000 mg, or the dose may be based on the patient's surface area, e.g., 500, 400, 300, 250, 200, or 100 mg/m$^2$. Usually between 1 and 8 doses, (e.g., 1, 2, 3, 4, 5, 6, 7 or 8) may be administered to treat a CD38-positive B-cell malignancy, but 9, 10, 11, 12, 13, 14, 15, 16, 17, 18, 19, 20 or more doses may be given.

The administration of the anti-CD38 antibody in the methods of the invention and in some embodiments of each and every one of the numbered embodiments listed below, may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose. For example, the anti-CD38 antibody in the methods of the invention may be administered at 8 mg/kg or at 16 mg/kg at weekly interval for 8 weeks, followed by administration at 8 mg/kg or at 16 mg/kg every two weeks for an additional 16 weeks, followed by administration at 8 mg/kg or at 16 mg/kg every four weeks by intravenous infusion.

The anti-CD38 antibodies may be administered in the methods of the invention and in some embodiments of each and every one of the numbered embodiments listed below, by maintenance therapy, such as, e.g., once a week for a period of 6 months or more.

For example, anti-CD38 antibodies in the methods of the invention and in some embodiments of each and every one of the numbered embodiments listed below, may be provided as a daily dosage in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

Anti-CD38 antibodies in the methods of the invention and in some embodiments of each and every one of the numbered embodiments listed below, may also be administered prophylactically in order to reduce the risk of developing cancer, delay the onset of the occurrence of an event in cancer progression, and/or reduce the risk of recurrence when a cancer is in remission. This may be especially useful in patients wherein it is difficult to locate a tumor that is known to be present due to other biological factors.

The anti-CD38 antibody in the methods of the invention and in some embodiments of each and every one of the numbered embodiments listed below, may be lyophilized for storage and reconstituted in a suitable carrier prior to use. This technique has been shown to be effective with conventional protein preparations and well known lyophilization and reconstitution techniques can be employed.

The anti-CD38 antibody in the methods of the invention and in some embodiments of each and every one of the numbered embodiments listed below, may be administered in combination with cyclophosphamide, doxorubicin, vincristine and prednisone (CHOP).

For example, CHOP and the individual constituents thereof, can be administered as described, in Moharhmad et al., Gun. Cancer Res 25:4950, 2000; McKelvey et al., Cancer 1484-1493; 1976; Armitage et al., J. Clin. Oncol. 2:898-902, 1984; Skeel, R. T., Handbook of Cancer Gliemotherapy, 3rd Edition, Little, Brown& Co., 1991:343. Typical routes of administration are intraperitoneal (i.p)., intravenous (i.v.) or oral (p.o.). Regimens may be either daily, every other day or every fourth day. Typical doses of the CHOP components are as follows: cyclophosphamide, up to 30 mg/kg single dose i.v. or i.p., or 20 mg/kg daily for eight days i.v. or i.p.; doxorubicin, up to 6 mg/kg single does i.v. or i.p.; vincristine, 0.2 to 0.5 mg/kg single dose i.p. or i.v.; prednisone, up to 10 mg/kg/day as a single agent, p.o.

For example CHOP may be administered at doses: cyclophosphamide 30 mg/kg, doxorubicin 2.5 mg/kg, vincristine 0.4 mg/kg prednisone 0.15 mg/kg. CHOP may be given every 21 days for different number of cycles. Cyclopshophamide, doxorubicin and vincristine may be given as i.v. infusion. Prednisone may be given as a tablet, taken daily by mouth for five days at the beginning of each cycle.

In the methods of the invention and in some embodiments of each and every one of the numbered embodiments listed below, the combination of the anti-CD38 antibody and CHOP may be administered over any convenient timeframe. For example, the anti-CD38 antibody and CHOP may be administered to a patient on the same day, and even in the same intravenous infusion, except for prednisone. However, the anti-CD38 antibody and CHOP may also be administered on alternating days or alternating weeks or months, and so on. In some methods, the anti-CD38 antibody and CHOP may be administered with sufficient proximity in time that they are simultaneously present (e.g., in the serum) at detectable levels in the patient being treated. In some methods, an entire course of treatment with the anti-CD38 antibody consisting of a number of doses over a time period is followed or preceded by a course of treatment with CHOP, consisting of a number of doses. A recovery period of 1, 2 or several days or weeks may be used between administration of the anti-CD38 antibody and CHOP.

The anti-CD38 antibody in the methods of the invention and in some embodiments of each and every one of the numbered embodiments listed below, may be administered in combination with cyclophosphamide, doxorubicin, vincristine and prednisone (CHOP).

The anti-CD38 antibody in the methods of the invention and in some embodiments of each and every one of the numbered embodiments listed below, may be administered in combination with cyclophosphamide, doxorubicin, vincristine, prednisone and an anti-CD20 antibody rituximab (R-CHOP).

Rituximab may be given as an intravenous infusion at a dose of 375 mg/m$^2$ and may be administered once weekly for 4 or 8 doses.

The combination of anti-CD38 antibody and CHOP may be administered together with any form of radiotherapy including external beam radiation, intensity modulated radiation therapy (IMIRT) and any form of radiosurgery including Gamma Knife, Cyberknife, Linac, and interstitial radiation (e.g. implanted radioactive seeds, GliaSite balloon), and/or with surgery. Radiotherapy may be used in patients having bulky disease (tumor size over about 10 cm) or in a palliative setting for patients who are not candidates for chemotherapy.

While having described the invention in general terms, the embodiments of the invention will be further disclosed in the following examples that should not be construed as limiting the scope of the claims.

FURTHER EMBODIMENTS OF THE INVENTION

Set out below are certain further embodiments of the invention according to the disclosures elsewhere herein. Features from embodiments of the invention set out above described as relating to the invention disclosed herein also relate to each and every one of these further numbered embodiments.

1. An anti-CD38 antibody for use in treating a subject having a CD38-positive hematological malignancy, in combination with cyclophosphamide, doxorubicin, vincristine and prednisone (CHOP).

2. Cyclophosphamide, doxorubicin, vincristine and prednisone (CHOP) for use in treating a subject having a CD38-positive hematological malignancy, in combination with an anti-CD38 antibody.

3. The combination of an anti-CD38 antibody, cyclophosphamide, doxorubicin, vincristine and prednisone (CHOP) for use in treating a subject having a CD38-positive hematological malignancy.

4. The anti-CD38 antibody for use according to embodiment 1, the CHOP for use according to embodiment 2, or the combination according to embodiment 3, wherein the anti-CD38 antibody induces in vitro killing of CD38-expressing cells by antibody-dependent cell-mediated cytotoxicity (ADCC), antibody-dependent cellular phagocytosis (ADCP), complement dependent cytotoxicity (CDC), apoptosis, or in vitro modulation of CD38 enzymatic activity, preferably wherein the anti-CD38 antibody induces killing of the CD38-expressing cells by ADCC or CDC in vitro.

5. The anti-CD38 antibody for use according to embodiment 1 or 4, the CHOP for use according to embodiment 2 or 4, or the combination for use according to embodiment 3 or 4, wherein the anti-CD38 antibody competes for binding to CD38 with an antibody comprising the heavy chain variable region (VH) of SEQ ID NO: 4 and the light chain variable region (VL) of SEQ ID NO: 5.

6. The anti-CD38 antibody for use according to embodiment 1, 4 or 5, the CHOP for use according to embodiment 2, 4 or 5, or the combination for use according to embodiment 3, 4 or 5, wherein the anti-CD38 antibody competes for binding to CD38 with an antibody comprising the heavy chain variable region (VH) of SEQ ID NO: 4 and the light chain variable region (VL) of SEQ ID NO: 5.

7. The anti-CD38 antibody for use according to any one of embodiments 1 or 4-6, the CHOP for use according to any one of embodiments 2 or 4-6, or the combination for use according to any one of embodiments 3-6, wherein the anti-CD38 antibody binds to an epitope comprising at least one amino acid in the region SKRNIQFSCKNIYR (SEQ ID NO: 2) and comprising at least one amino acid in the region EKVQTLEAWVIHGG (SEQ ID NO: 3) of human CD38 (SEQ ID NO: 1).

8. The anti-CD38 antibody, CHOP or combination for use according to embodiment 7, wherein the anti-CD38 antibody binds to an epitope comprising at least KRN in the region SKRNIQFSCKNIYR (SEQ ID NO: 2) and comprising at least VQLT (SEQ ID NO: 20) in the region EKVQTLEAWVIHGG (SEQ ID NO: 3) of human CD38 (SEQ ID NO: 1).

9. The anti-CD38 antibody for use according to any one of embodiments 1, or 4-8, the CHOP for use according to any one of embodiments 2, or 4-8, or the combination for use according to any one of embodiments 3-8, wherein the anti-CD38 antibody:
  (i) is of IgG1, IgG2, IgG3 or IgG4 isotype;
  (ii) has a biantennary glycan structure with fucose content of about 50%, 40%, 45%, 40%, 35%, 30%, 25%, 20%, 15%, 14%, 13%, 12%, 11% 10%, 9%, 8%, 7%, 6%, 5%, 4%, 3%, 2%, 1% or 0%;
  (iii) comprises a substitution in the antibody Fc at amino acid position 256, 290, 298, 312, 356, 330, 333, 334, 360, 378 or 430, when residue numbering according to the EU index; and/or
  (iv) binds to CD38 with an affinity of $1\times10^{-9}$ or less, $1\times10^{-10}$ or less, $1\times10^{-11}$ or less, or $1\times10^{-12}$ or less.

10. The anti-CD38 antibody for use according to any one of embodiments 1, or 4-9, the CHOP for use according to any one of embodiments 2, or 4-9, or the combination for use according to any one of embodiments 3-9, wherein the anti-CD38 antibody comprises:
  (i) the heavy chain complementarity determining regions (HCDR) 1 (HCDR1), 2 (HCDR2) and 3 (HCDR3) sequences of SEQ ID NOs: 6, 7 and 8, respectively;
  (ii) the light chain complementarity determining regions (LCDR) 1 (LCDR1), 2 (LCDR2) and 3 (LCDR3) sequences of SEQ ID NOs: 9, 10 and 11, respectively;
  (iii) comprises the heavy chain variable region (VH) of SEQ ID NO: 4 and the light chain variable region (VL) of SEQ ID NO: 5;
  (iv) comprises a heavy chain comprising an amino acid sequence that is 95%, 96%, 97%, 98% or 99% identical to that of SEQ ID NO: 12 and a light chain comprising an amino acid sequence that is 95%, 96%, 97%, 98% or 99% identical to that of SEQ ID NO: 13; or
  (v) comprises the heavy chain of SEQ ID NO: 12 and the light chain of SEQ ID NO: 13.

11. The anti-CD38 antibody for use according to any one of embodiments 1, or 4-10, the CHOP for use according to any one of embodiments 2, or 4-10, or the combination for use according to any one of embodiments 3-10, wherein the CD38-positive hematological malignancy is multiple myeloma, acute lymphoblastic leukemia (ALL), non-Hodgkin's lymphoma, diffuse large B-cell lymphoma (DLBCL), Burkitt's lymphoma (BL), follicular lymphoma (FL) or mantle-cell lymphoma (MCL), specifically wherein the CD38-positive hematological malignancy is DLBCL.

12. The anti-CD38 antibody for use according to any one of embodiments 1, or 4-11, the CHOP for use according to any one of embodiments 2, or 4-11, or the combination for use according to any one of embodiments 3-11, wherein:
  (i) the subject is resistant to or has acquired resistance to treatment with at least one chemotherapeutic agent or a combination of at least one chemotherapeutic agent and an anti-CD20 antibody; and/or
  (ii) the subject has discontinued treatment with at least one chemotherapeutic agent or a combination of at least one chemotherapeutic agent and an anti-CD20 antibody due to side-effects.

13. The anti-CD38 antibody, CHOP or combination for use according to embodiment 12, wherein the anti-CD20 antibody is rituximab (RITUXAN®), ofatumumab (ARZERRA®), veltuzumab, ocrelizumab, obinutuzumab (GA-101), PRO13192 or ocratuzumab (AME-133v), specifically wherein the anti-CD20 antibody is rituximab.

14. The anti-CD38 antibody, CHOP or combination for use according to embodiment 12 or 13, wherein the at least one chemotherapeutic agent is cyclophosphamide, doxorubicin, vincristine, prednisone, ifosfamide, carboplatin or etoposide, optionally wherein:
  (i) the at least one chemotherapeutic agent is a combination of cyclophosphamide, doxorubicin, vincristine and prednisone (CHOP); or
  (ii) the at least one chemotherapeutic agent is a combination of ifosfamide, carboplatin and etoposide (ICE).

15. The anti-CD38 antibody for use according to any one of embodiments 1, or 4-14, the CHOP for use according to any one of embodiments 2, or 4-14, or the combination for use according to any one of embodiments 3-14, wherein the anti-CD38 antibody, cyclophosphamide, doxorubicin, vincristine and prednisone are administered simultaneously, sequentially or separately.

16. The anti-CD38 antibody for use according to any one of embodiments 1, or 4-15, the CHOP for use according to any one of embodiments 2, or 4-15, or the combination for use according to any one of embodiments 3-15, wherein the subject is further treated with radiotherapy.

17. The anti-CD38 antibody for use according to any one of embodiments 1, or 4-16, the CHOP for use according to any one of embodiments 2, or 4-16, or the combination for use according to any one of embodiments 3-16, wherein:
   (i) the anti-CD38 antibody comprises the heavy chain variable region (VH) of SEQ ID NO: 4 and the light chain variable region (VL) of SEQ ID NO: 5;
   (ii) the anti-CD38 antibody is IgG1; and
   (iii) wherein the CD38-positive hematological malignancy is DLBCL.

18. The anti-CD38 antibody for use according to any one of embodiments 1, or 4-16, the CHOP for use according to any one of embodiments 2, or 4-16, or the combination for use according to any one of embodiments 3-16, wherein:
   (i) the anti-CD38 antibody comprises the heavy chain variable region (VH) of SEQ ID NO: 4 and the light chain variable region (VL) of SEQ ID NO: 5;
   (ii) the anti-CD38 antibody is IgG1; and
   (iii) wherein the CD38-positive hematological malignancy is Burkitt's lymphoma.

Example 1 Combination Therapy with Daratumumab and CHOP in Patient Derived Non-Hodkgin's Lymphoma (NHL) Models Methods ST1361 is a NHL-DLBCL (diffuse large B-cell lymphoma) PDX (patient derived xenograft) model originating from a fifty-eight year old Hispanic male chemo-naïve prior to metastatic sample collection. The patient had been treated with 8 cycles of R-CHOP prior to the resection, with subsequent treatments with R-ICE and R-GEMOX.

Tumors were implanted in immunocompromised mice between 5-8 weeks of age. When tumors reached approximately 125-250 mm$^3$ (day 0) animals were randomized into treatment and control groups and dosing was initiated on Day 0. Daratumumab was dosed at 20 mg/kg once a week for 3 weeks. CHOP and R-CHOP at the concentrations described below were dosed once on day 0. CHOP (cyclophosphoamide: 30 mg/kg; doxorubicin: 2.5 mg/kg; vincristine: 0.4 mg/kg)-IV DAY 0; prednisone: 0.15 mg/kg DAYS 0-4; R-CHOP: rituximab 20 mg/kg-IP DAY 0. Beginning Day 0, tumor volume was measured twice weekly by digital caliper and data including individual and mean estimated tumor volumes (Mean TV±SEM) recorded for each group. The study was used to measure tumor growth inhibition until the control group was terminated and then continued as a survival study to evaluate the duration of daratumumab efficacy.

For the study, beginning Day 0, tumor dimensions were measured twice weekly by digital caliper and data including individual and mean estimated tumor volumes (mean TV±SEM) recorded for each group. Tumor volume (TV) was calculated using the formula: TV=width$^2$×length×0.52. % tumor growth inhibition (% TGI) values were calculated for each treatment group (T) versus control (C) using initial (i) and final (f) tumor measurements by the formula: % TGI=1−T$_f$−T$_i$/C$_f$−C.

Results

Daratumumab in combination with CHOP or R-CHOP was highly effective in this patient-derived tumor model of DLBCL. On day 31, CHOP regimen by itself slowed the tumor growth by about 27% whereas daratumumab inhibited tumor growth by ~71%. R-CHOP was a more effective therapy with 82% tumor growth inhibition. Combination of daratumumab with CHOP or R-CHOP showed tumor regression and by the end of the study none of the animals had measurable tumors. Beyond day 31, 100% of the animals in Table 1.

TABLE 1

| Treatment | Mean tumor volume (mm$^3$) ± SEM | % TGI |
|---|---|---|
| Isotype control | 2192 ± 160 | |
| Daratumumab | 744 ± 236 | 71% |
| CHOP | 1634 ± 159 | 27% |
| R-CHOP | 513 ± 104 | 82% |
| Daratumumab/CHOP | 0 | 107% |
| Daratumumab/R-CHOP | 0 | 107% |

Figure 1B:
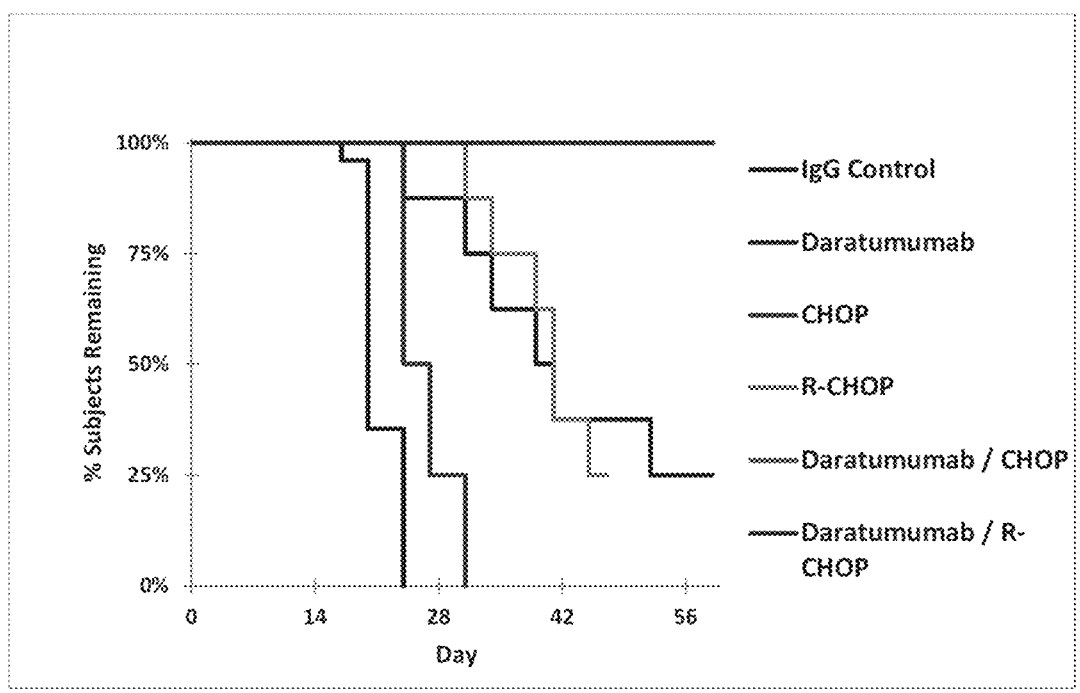
FIG. 1B shows the median survival time plotted against days after tumor inoculation of the study of FIG. 1A.

% TGI: percent tumor growth inhibition daratumumab+CHOP and daratumumab+R-CHOP survived, the other groups showed loss of animals due to tumor progression. FIG. 1A shows the tumor volume over time for each treatment group, and FIG. 1B shows the median % survival over time. Table 1 shows the % TGI up to day 31 of the study. At day zero, tumor volume for each group was 145-146 mm$^3$. Combination of daratumumab and CHOP resulted in 100% TGI even after 60 days of initiation of the study.

In this study, the efficacy of daratumumab was evaluated in a patient-derived DLBCL model. This patient was treated with R-CHOP and responded to R-CHOP initially but later died due to disease progression. The goal of this study was to determine if addition of daratumumab would offer greater benefit for DLBCL patients. Compared to monotherapy (daratumumab, CHOP or R-CHOP), addition of daratumumab to CHOP or R-CHOP resulted in tumor regression in all animals while the animals in all other groups succumbed to death as a result of disease burden. The combination of daratumumab with CHOP or R-CHOP showed greater than additive effect on tumor growth inhibition.

Example 2. Efficacy of Daratumumab in Combination with CHOP in Burkitt's Lymphoma As a model for Burkitt's lymphoma, NAMALWA cells were utilized to study the efficacy of daratumumab alone or in combination with CHOP.

Methods

Namalwa cells were maintained in vitro in RPMI 1640 medium supplemented with fetal bovine serum (10% v/v), and L-glutamine (2 mM) at 37° C. in an atmosphere of 5% CO2 in air. The cells were routinely subcultured twice weekly by trypsin-EDTA treatment. The cells growing in an exponential growth phase were harvested and counted for tumor inoculation. The mice were injected with 2×10$^5$ Namalwa cells in 0.1 ml of PBS with matrigel (1:1) subcutaneously and the treatments were started when the mean tumor size reached 189 mm$^3$. The date of tumor cell inoculation is denoted as day 0. The major endpoint was to see if the tumor growth can be delayed or tumor-bearing mice can be cured. Tumor sizes were measured twice weekly and % TGI values calculated as described in Example 1.

Results

Animals were divided in four treatment groups and were administered vehicle (isotype control), daratumumab, CHOP or daratumumab in combination with CHOP at dosages as described in Table 2.

TABLE 2

Figure 2:
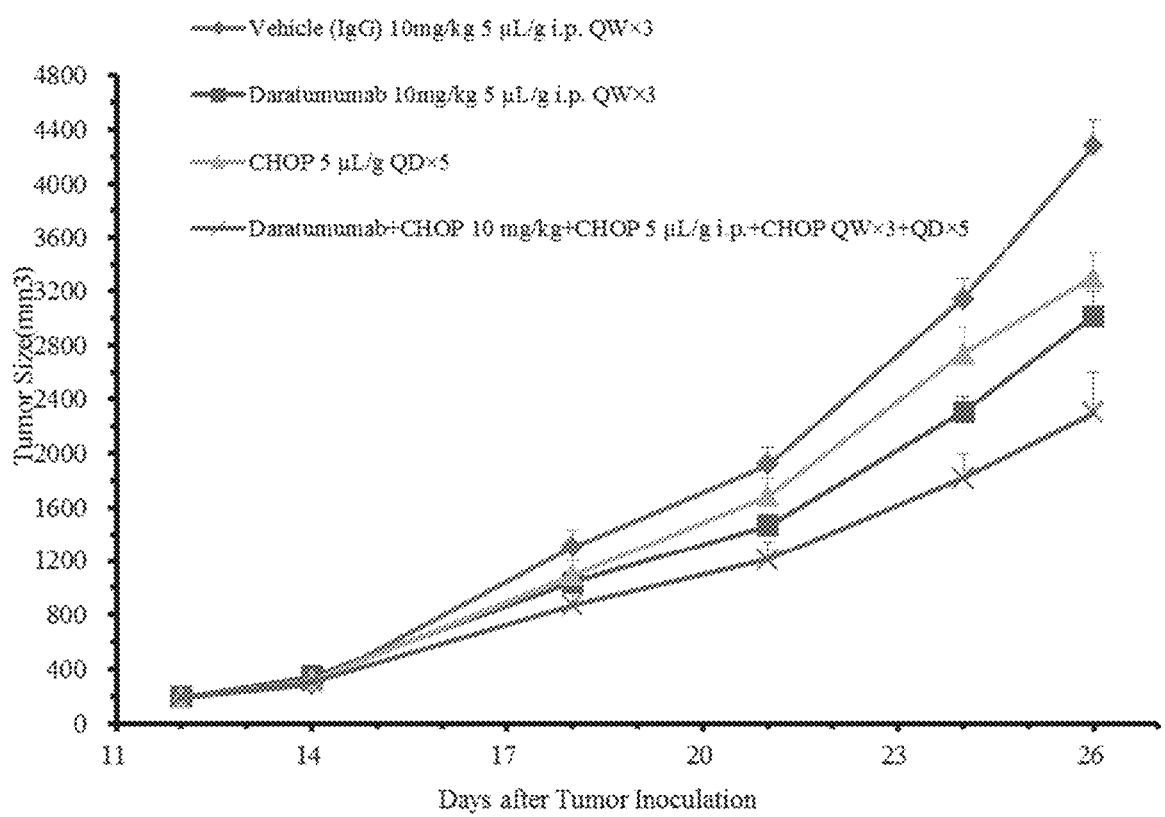
FIG. 2 shows efficacy of daratumumab in a preclinical model of non-Hodgkin's lymphoma alone or in combination with CHOP. $2 \times 10^5$ NAMALWA cells in matrigel were implanted into NOD SCID mice and treatment initiated when the main tumor size reached approximately 189 mm$^3$. Daratumumab was administered at 10 mg/kg once a week for three weeks. CHOP was administered daily on days 0-5 using following doses: cyclophosphoamide (CTX): 5 mg/kg i.v.; doxorubicin: 0.5 mg/kg i.v; vincristine: 0.08 mg/kg i.v., prednisone: 0.03 mg/kg p.o. Tumor volume was measured every three days. The Y-axis represents tumor volume±SEM

| Groups | n | Treatment | | Dose (mg/kg) | Dosing Route | Schedule |
|---|---|---|---|---|---|---|
| 1 | 10 | Vehicle (IgG) | | 10 | i.p. | QW × 3 |
| 2 | 10 | Daratumumab | | 10 | i.p. | QW × 3 |
| 3 | 10 | CHOP | CTX | 5 | i.v. | QD × 5 |
|   |    |      | Doxorubicin | 0.5 | i.v. |  |
|   |    |      | Vincristine | 0.08 | i.v. |  |
|   |    |      | Prednisone | 0.03 | p.o. |  |
| 4 | 10 |  | Daratumumab | 10 | i.p. | QW × 3 |
|   |    | CHOP | CTX | 5 | i.v. | QD × 5 |
|   |    |      | Doxorubicin | 0.5 | i.v. |  |
|   |    |      | Vincristine | 0.08 | i.v. |  |
|   |    |      | Prednisone | 0.03 | p.o. |  | n, animal number
i.p intraperitoneal injection
i.v. intravenous injection
p.o. oral administration
QD: daily dosing
QW: once a week
CTX: cyclophosphoamide FIG. 2 shows results of the efficacy of daratumumab alone or in combination with CHOP in NAMALWA model of Burkitt's lymphoma. The reduction in tumor sizes (measured as tumor volume) in different treatment groups at different time points after tumor inoculation are shown in FIG. 2. The mean tumor size of the vehicle group (Group1) reached 4,281 mm$^3$ at day 26 post tumor inoculation. Treatment with daratumumab at 10 mg/kg, CHOP and daratumumab at 10 mg/kg in combination with CHOP produced significant antitumor activity in tumor size at day 26 post tumor inoculation separately. The mean tumor sizes were 3,017 mm$^3$ (T/C value=70.46%, p value <0.001), 3,304 mm$^3$ (T/C value=77.17%, p value=0.003) and 2,303 mm$^3$ (T/C value=53.79%, p value <0.001) at the same time with tumor growth delay of 2, 1 and 4 day(s) respectively at tumor size of 2,303 mm$^3$.

Example 3. Efficacy of Daratumumab in Combination with CHOP in Non-Hodgkin's Lymphoma SU-DHL-6 cell line based NHL-DLBCL model was utilized to study the efficacy of daratumumab alone or in combination with CHOP.

Methods

The SU-DHL-6 cells were maintained separately in vitro in RPMI1640 medium supplemented with 20% fetal bovine serum (v/v) at 37° C. in an atmosphere of 5% CO2 in air. The cells were routinely subcultured twice weekly. The cells growing in an exponential growth phase were harvested and counted for tumor inoculation. NOD SCID mice were γ-irradiated (200 rads) at 24 h before injection. Each mouse was inoculated subcutaneously at the right flank with SU-DHL-6 tumor cells (5×10$^6$) in 0.1 ml of PBS with matrigel (1:1) for tumor development. The treatments were started when the tumor size reaches approximately 154 mm$^3$. The date of tumor cell inoculation is denoted as day 0. Tumor sizes were measured twice weekly and % TGI values calculated as described in Example 1.

Animals were divided in four treatment groups and were administered vehicle, daratumumab, CHOP or daratumumab in combination with CHOP at dosages as described in Table 3.

Figure 3:
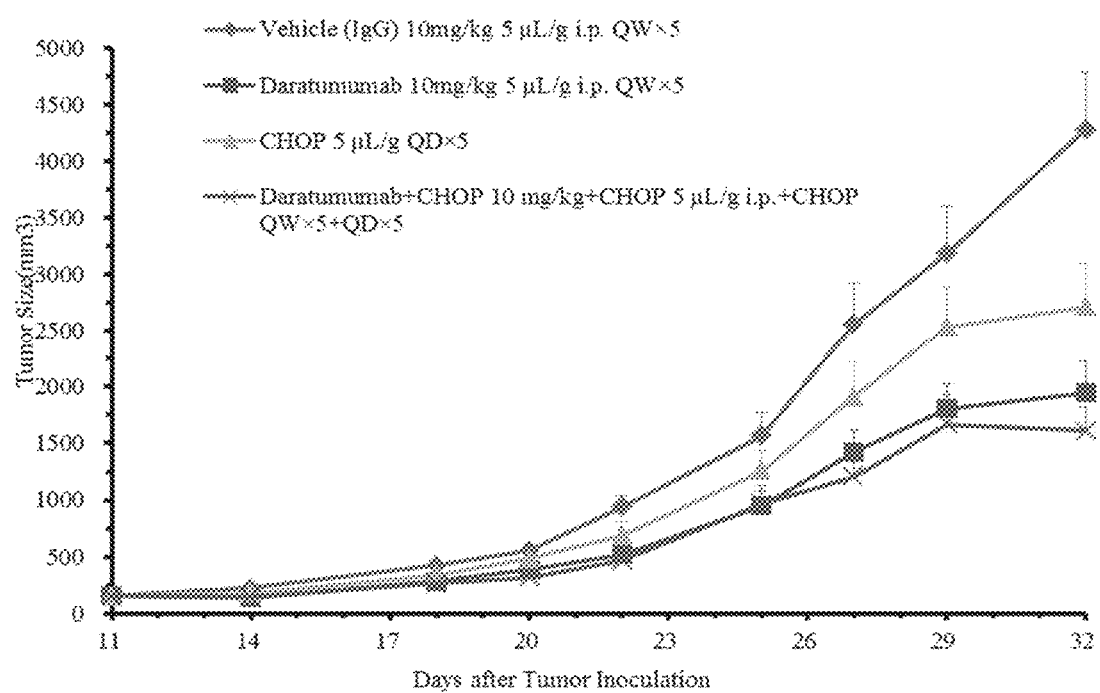
FIG. 3 shows efficacy of of daratumumab in a preclinical model of DLBCL alone or in combination with CHOP. $5 \times 10^6$ SU-DHL-6 cells were implanted into NOD SCID mice and treatment initiated when the main tumor size reached approximately 154 mm$^3$. Daratumumab was administered at 10 mg/kg once a week for four weeks. CHOP was administered daily on days 0-5 using following doses: cyclophosphoamide (CTX): 5 mg/kg i.v.; doxorubicin: 0.5 mg/kg i.v.; vincristine: 0.08 mg/kg i.v., prednisone: 0.03 mg/kg p.o. Tumor size was plotted as Mean±SEM.

The results of tumor sizes in different groups at different time points after tumor inoculation are shown in FIG. 3. The mean tumor size of the vehicle group (Group1) reached 4,281 mm$^3$ at day 32 post tumor inoculation. Treatment with daratumumab at 10 mg/kg and daratumumab at 10 mg/kg in combination with CHOP produced significant antitumor activity in tumor size at day 32 post tumor inoculation separately. The mean tumor sizes were 1,946 mm$^3$ (T/C value=45.45%, p value=0.006) and 1,611 mm$^3$ (T/C value=37.62%, p value=0.002) at the same time with tumor growth delay of 3 and 3.5 days respectively at tumor size of 1,500 mm$^3$. Treatment with CHOP could decrease tumor size when compared to vehicle group but the decrease didn't reach significant difference.

TABLE 3

| Groups | n[a] | Treatment | | Dose (mg/kg) | Dosing Route[b] | Schedule[c] |
|---|---|---|---|---|---|---|
| 1 | 10 | Vehicle (IgG) | | 10 | i.p. | QW × 4 |
| 2 | 10 | Daratumumab | | 10 | i.p. | QW × 4 |
| 3 | 10 | CHOP | CTX | 5 | i.v. | QD × 5 |
|   |    |      | Doxorubicin | 0.5 | i.v. |  |
|   |    |      | Vincristine | 0.08 | i.v. |  |
|   |    |      | Prednisone | 0.03 | p.o. |  |
| 4 | 10 |  | Daratumumab | 10 | i.p. | QW × 4 |
|   |    | CHOP | CTX | 5 | i.v. | QD × 5 |
|   |    |      | Doxorubicin | 0.5 | i.v. |  |
|   |    |      | Vincristine | 0.08 | i.v. |  |
|   |    |      | Prednisone | 0.03 | p.o. |  | n, animal number
i.p. intraperitoneal injection
i.v. intravenous injection
p.o. oral administration
QD: daily dosing
QW: once a week
CTX: cyclophosphoamide Example 4. Sequential or Simultaneous Therapy with Daratumumab in Combination with CHOP or R-CHOP Provides Efficacy in Patient Derived Non-Hodgkin's Lymphoma (NHL) Models Efficacy of daratumumab alone or in combination with CHOP or R-CHOP was assssed using simultaneous or sequential dosing in the patient derived DLBCL tumor model ST1361 and according to methods described in Example 1.

Animals were divided into treatment groups and dosed as shown in Table 4. Daratumumab and R-CHOP were dosed simultaneously at day 0 or at 7 day interval.

TABLE 4

| Group | n | Treatment | | Dose (mg/kg) | Dosing Route | Schedule |
|---|---|---|---|---|---|---|
| 1 | 10 | Vehicle (IgG) | | 10 | i.p. | QW × 3 |
| 2 | 10 | Daratumumab | | 20 | i.p. | QW × 3 |
|   |    | CHOP | CTX | 5 | i.v. | D 0 |
|   |    |      | Doxorubicin | 0.5 | i.v. | D 0 |
|   |    |      | Vincristine | 0.08 | i.v. | D 0 |
|   |    |      | Prednisone | 0.03 | p.o. | D 0-4 |
| 3 | 10 | Daratumumab | | 20 | i.p. | QW × 3 |
|   |    | R-CHOP | Rituximab | 20 | i.p. | QW × 3 |
|   |    |        | CTX | 5 | i.v. | D 0 |
|   |    |        | Doxorubicin | 0.5 | i.v. | D 0 |
|   |    |        | Vincristine | 0.08 | i.v. | D 0 |
|   |    |        | Prednisone | 0.03 | p.o. | D 0-4 |
| 4 | 10 | Daratumumab | | 20 | i.p. | D 7 |
|   |    | R-CHOP | Rituximab | 20 | i.p. | D 0 |
|   |    |        | CTX | 5 | i.v. | D 0 |
|   |    |        | Doxorubicin | 0.5 | i.v. | D 0 |
|   |    |        | Vincristine | 0.08 | i.v. | D 0 |
|   |    |        | Prednisone | 0.03 | p.o. | D 0-4 |
| 5 | 10 | Daratumumab | Daratumumab | 20 | i.p. | D 0 |
|   |    | R-CHOP | Rituximab | 20 | i.p. | D 7 |
|   |    |        | CTX | 5 | i.v. | D 0 |
|   |    |        | Doxorubicin | 0.5 | i.v. | D 0 |
|   |    |        | Vincristine | 0.08 | i.v. | D 0 |
|   |    |        | Prednisone | 0.03 | p.o. | D 0-4 | n, animal number
i.p intraperitoneal injection
i.v. intravenous injection
p.o. oral administration
QD: daily dosing
QW: once a week dosing
D 0 = day 0 dosing
D 0-4 = dosing once a day at days d 0-d 4

Results

Figure 4:
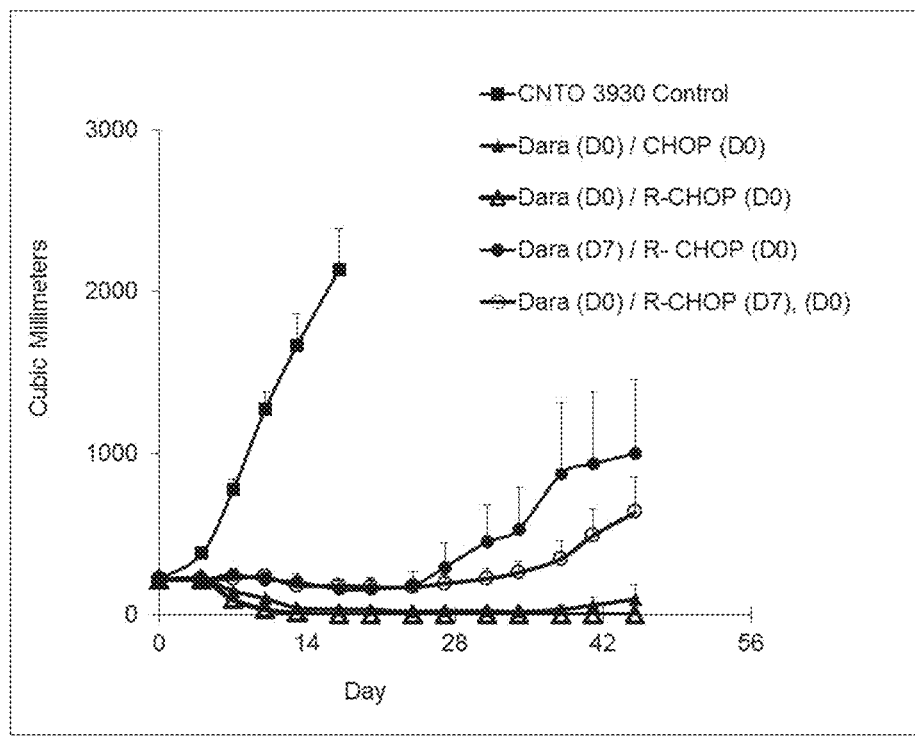
FIG. 4 shows efficacy of daratumumab in a patient-derived model of diffuse large B-cell lymphoma (DLBCL) in combination with CHOP or R-CHOP administered simultaneously or sequentially up to day 45 of the study. Daratumumab was administered at 20 mg/kg once a week for three weeks at day 0 or at day 7. CHOP was administered once on day 0 except prednisone was administered on days 0-4 using following regimens: CHOP: (cyclophosphoamide (CTX): 30 mg/kg i.v.; doxorubicin: 2.5 mg/kg i.v; vincristine: 0.4 mg/kg i.v); prednisone: 0.15 mg/kg p.o. Rituximab was administered at 20 mg/kg i.p. at either day 0 or day 7. Tumor size was plotted as Mean±SEM. CNTO3930: isotype control. Values in parenthesis indicate the day of dosing. The data represents results from an ongoing study at day 44.
Figure 5:
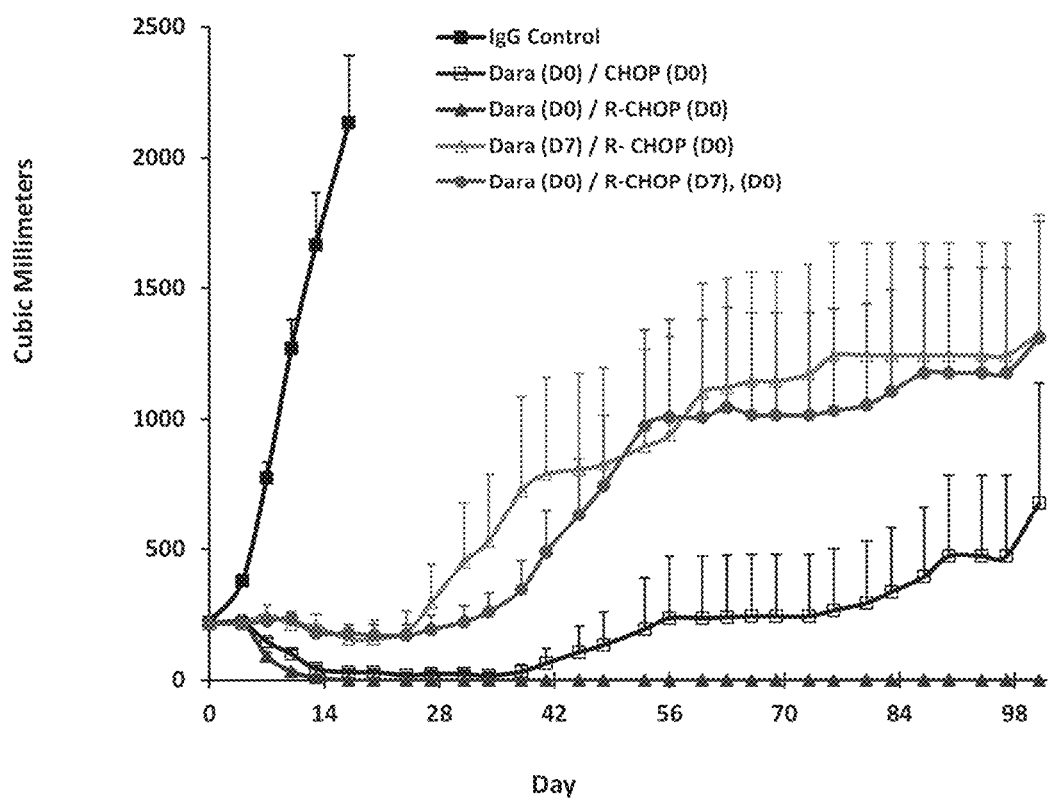
FIG. 5 shows efficacy of daratumumab in a patient-derived model of DLBCL in combination with CHOP or R-CHOP administered simultaneously or sequentially up to day 101 of the study. Dosing was as in FIG. 4. Tumor size was plotted as Mean±SEM. CNTO3930: isotype control. Values in parenthesis indicate the day of dosing. Statistical differences in tumor volume were determined using a two-tailed, one-way ANOVA followed by Dunnett's multiple comparisons test comparing treated single-agent groups with control and combinations with standard agent. *P<0.05 versus control, †P<0.05 versus CHOP, cyclophospharnide, doxorubicin, vincristine, and prednisone; DLBCL, diffuse large B-cell lymphoma. IHC, immunohistochemistry; i.v., intravenous; i.p., intraperitoneal.

FIG. 4 shows the results of tumor growth curves in response treatment up to 45 days of the study. Tumors in the vehicle control group reached a mean tumor volume of 2134 mm$^3$ by day 17. Tumors in the daratumumab+CHOP group regressed to a mean tumor volume of 96 mm$^3$ by day 45. Tumors in animals treated with daratumumab and R-CHOP simultaneously on day 0 (group 4), completely regressed by day 45. Tumors in animals treated with R-CHOP on day 0, followed by daratumumab on day 7 (group 5) showed mean tumor volume of 998 mm$^3$. Tumors that were treated with daratumumab on day 0, followed by R-CHOP on day 7 (group 6) showed mean tumor volume of 633 mm$^3$. The study was continued to up to 101 days. Animals treated with daratumumab and R-CHOP simultaneously on day 0 (group 4), completely regressed by day 101 also.

What is claimed is:

1. A method of treating non-Hodgkin's lymphoma (NHL) in a subject in need thereof, comprising administering to the subject an anti-CD38 antibody in combination with cyclophosphamide, doxorubicin, vincristine and prednisone (CHOP), wherein:
   a) the NHL is diffuse large B-cell lymphoma (DLBCL), Burkitt's lymphoma (BL), follicular lymphoma (FL) or mantle-cell lymphoma (MCL),
   b) the anti-CD38 antibody induces in vitro killing of CD38-expressing cells by antibody-dependent cell-mediated cytotoxicity (ADCC), antibody-dependent cellular phagocytosis (ADCP), complement dependent cytotoxicity (CDC), apoptosis, or in vitro modulation of CD38 enzymatic activity, and
   c) the anti-CD38 antibody comprises a heavy chain complementarity determining region 1 (HCDR1), a HCDR2 and a HCDR3 amino acid sequences of SEQ ID NOs: 6, 7 and 8, respectively, and a light chain complementarity determining region 1 (LCDR1), a LCDR2 and a LCDR3 amino acid sequences of SEQ ID NOs: 9, 10 and 11, respectively.

2. The method of claim 1, wherein the anti-CD38 antibody induces killing of the CD38-expressing cells by ADCC or CDC in vitro.

3. The method of claim 2, wherein the anti-CD38 antibody is of IgG1, IgG2, IgG3 or IgG4 isotype.

4. The method of claim 3, wherein the anti-CD38 antibody has a biantennary glycan structure with fucose content of about 50%, 45%, 40%, 35%, 30%, 25%, 20%, 15%, 14%, 13%, 12%, 11% 10%, 9%, 8%, 7%, 6%, 5%, 4%, 3%, 2%, 1% or 0%.

5. The method of claim 3, wherein the anti-CD38 antibody comprises a substitution in the antibody Fc at amino acid position 256, 290, 298, 312, 356, 330, 333, 334, 360, 378 or 430, wherein residue numbering is according to the EU index.

6. The method of claim 1, wherein the anti-CD38 antibody comprises a heavy chain variable region (VH) of SEQ ID NO: 4 and a light chain variable region (VL) of SEQ ID NO: 5.

7. The method of claim 1, wherein the anti-CD38 antibody comprises a heavy chain of SEQ ID NO: 12 and a light chain of SEQ ID NO: 13.

8. The method of claim 1, wherein the subject is resistant to or has acquired resistance to treatment with at least one chemotherapeutic agent or a combination of at least one chemotherapeutic agent and an anti-CD20 antibody.

9. The method of claim 1, wherein the subject has discontinued treatment with at least one chemotherapeutic agent or a combination of at least one chemotherapeutic agent and an anti-CD20 antibody due to side effects.

10. The method of claim 8 or 9, wherein the anti-CD20 antibody is rituximab, ofatumumab, veltuzumab, ocrelizumab, obinutuzumab (GA-101), PRO13192 or ocratuzumab (AME-133v).

11. The method of claim 10, wherein the anti-CD20 antibody is rituximab.

12. The method of claim 8 or 9, wherein the at least one chemotherapeutic agent is cyclophosphamide, doxorubicin, vincristine, prednisone, ifosfamide, carboplatin or etoposide.

13. The method of claim 12, wherein the at least one chemotherapeutic agent is a combination of cyclophosphamide, doxorubicin, vincristine and prednisone (CHOP).

14. The method of claim 12, wherein the at least one chemotherapeutic agent is a combination of ifosfamide, carboplatin and etoposide (ICE).

15. The method of claim 1, wherein the anti-CD38 antibody, cyclophosphamide, doxorubicin, vincristine and prednisone are administered simultaneously.

16. The method of claim 1, wherein the subject is further treated with radiotherapy.

17. The method of claim 1, wherein the anti-CD38 antibody, cyclophosphamide, doxorubicin, vincristine and prednisone are administered sequentially or separately.

18. The method of claim 1, wherein the NHL is BL.

19. The method of claim 1, wherein the NHL is FL.

20. The method of claim 1, wherein the NHL is MCL.

* * * * *